United States Patent
Zhang et al.

(10) Patent No.: US 11,414,686 B2
(45) Date of Patent: Aug. 16, 2022

(54) STOICHIOMETRIC NUCLEIC ACID PURIFICATION USING RANDOMER CAPTURE PROBE LIBRARIES

(71) Applicant: WILLIAM MARSH RICE UNIVERSITY, Houston, TX (US)

(72) Inventors: David Zhang, Houston, TX (US); Alessandro Pinto, Houston, TX (US)

(73) Assignee: William Marsh Rice University, Houston, TX (US)

( * ) Notice: Subject to any disclaimer, the term of this patent is extended or adjusted under 35 U.S.C. 154(b) by 576 days.

(21) Appl. No.: 16/099,359

(22) PCT Filed: May 5, 2017

(86) PCT No.: PCT/US2017/031346
§ 371 (c)(1),
(2) Date: Nov. 6, 2018

(87) PCT Pub. No.: WO2017/193025
PCT Pub. Date: Nov. 9, 2017

(65) Prior Publication Data
US 2019/0284596 A1    Sep. 19, 2019

Related U.S. Application Data

(60) Provisional application No. 62/332,778, filed on May 6, 2016.

(51) Int. Cl.
| | |
|---|---|
| *C12P 19/34* | (2006.01) |
| *C12N 15/10* | (2006.01) |
| *C40B 30/00* | (2006.01) |
| *C40B 40/08* | (2006.01) |
| *C12Q 1/68* | (2018.01) |
| *C12Q 1/6811* | (2018.01) |

(52) U.S. Cl.
CPC .......... *C12P 19/34* (2013.01); *C12N 15/1003* (2013.01); *C12Q 1/68* (2013.01); *C12Q 1/6811* (2013.01); *C40B 30/00* (2013.01); *C40B 40/08* (2013.01)

(58) Field of Classification Search
CPC ......... C12P 19/34; C12Q 1/68; C12Q 1/6811; C12N 15/1003; C40B 30/00; C40B 40/08
See application file for complete search history.

(56) References Cited

U.S. PATENT DOCUMENTS

| | | | |
|---|---|---|---|
| 5,891,625 A | 4/1999 | Buchardt et al. | |
| 2003/0096277 A1 | 5/2003 | Chen | |
| 2009/0053720 A1 | 2/2009 | Newton | |
| 2010/0009355 A1 | 1/2010 | Kolodney | |
| 2010/0285478 A1 | 11/2010 | Chen et al. | |
| 2011/0306758 A1 | 12/2011 | Zhang | |
| 2013/0071839 A1 | 3/2013 | Seelig et al. | |
| 2013/0149695 A1 | 6/2013 | Lee et al. | |
| 2013/0231253 A1 | 9/2013 | Amorese et al. | |
| 2013/0274135 A1 | 10/2013 | Zhang et al. | |
| 2014/0017685 A1 | 1/2014 | Fu | |
| 2016/0340727 A1 | 11/2016 | Zhang et al. | |
| 2017/0029875 A1 | 2/2017 | Zhang et al. | |
| 2017/0067090 A1 | 3/2017 | Zhang et al. | |

FOREIGN PATENT DOCUMENTS

| | | |
|---|---|---|
| WO | WO 2011/146403 A1 | 11/2011 |
| WO | WO 2012/058488 A1 | 5/2012 |
| WO | WO 2012/151560 A1 | 11/2012 |
| WO | WO 2013/097173 A1 | 7/2013 |
| WO | WO 2014/177540 A1 | 11/2014 |
| WO | WO 2015/010020 A1 | 1/2015 |
| WO | WO 2016/065192 A1 | 5/2015 |
| WO | WO 2015/094429 A1 | 6/2015 |
| WO | WO 2015/161173 A1 | 10/2015 |
| WO | WO 2015/179339 A1 | 11/2015 |
| WO | WO 2016/064856 A1 | 4/2016 |

OTHER PUBLICATIONS

Bonnet et al., "Nucleic acid hybridization: Robust sequence discrimination," *Nat. Chem.*, 4:155-157, 2012.
PCT International Preliminary Report on Patentability dated Nov. 15, 2018 issued in PCT/US2017/031346.
PCT International Search Report and Written Opinion dated Aug. 7, 2017 issued in PCT/US2017/031346.
Vestheim et al., "Blocking primer to enhance PCR amplification of rare sequences in mixed samples—a case study on prey DNA an Antarctic krill stomachs," *Front. Zool.*, 5:1-11, 2008.
Wang et al., "Simulation-guided DNA probe design for consistently ultraspecific hybridization," *Nat. Chem.*, 7:545-553, 2015.
Wu et al., "Continuously tunable nucleic acid hybridization probes," *Nat. Meth.*, 12:1191-1196, 2015.
Wu et al., "Multiplexed enrichment of rare DNA variants via sequence-selective and temperature-robust amplification," *Nat. Biomed. Eng.*, 1:714-723, 2017.
Zhang et al., "Optimizing the specificity of nucleic acid hybridization," *Nat. Chem.*, 4:208-214, 2012.

*Primary Examiner* — Robert H Havlin
(74) *Attorney, Agent, or Firm* — Parker Highlander PLLC

(57) ABSTRACT

This disclosure describes a method of purifying several full-length oligonucleotide targets from corresponding synthesis truncation products, in a way that ensures roughly stoichiometric equality among the targets.

20 Claims, 19 Drawing Sheets
Specification includes a Sequence Listing.

Precursor 1  GTGGATGATCAACGC ACACTCTC TCGCTTC...

5'-truncated sequence (undesired)  GATCAACGC ACACTCTC TCGCTTC... ⟹ Ⓐ

Precursor 2  GTGGATGATCAACGC ACTCAGTC TCAATCA...

5'-truncated sequence (undesired)  TCA...

+

Biotin—CACCTACTAGTTGCGT SWSWSWG
          2              1
Capture probe library

FIG. 2

Precursors for making 1x Target 1
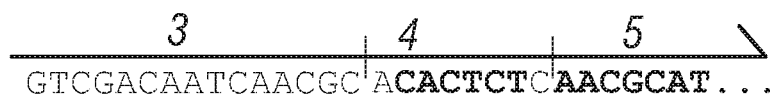
Precursors for making 2x Target 2
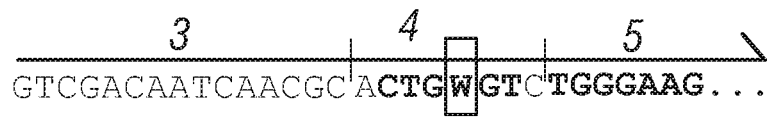
Precursors for making 6x Target 3
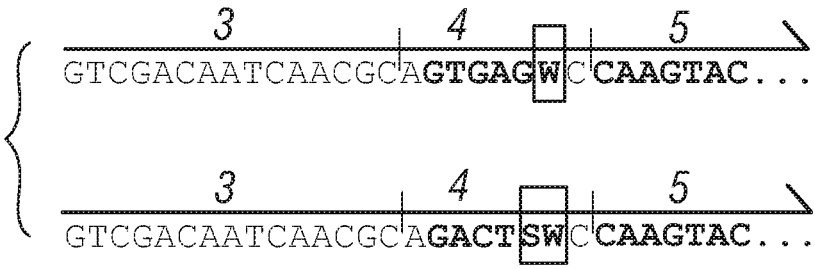
FIG. 5

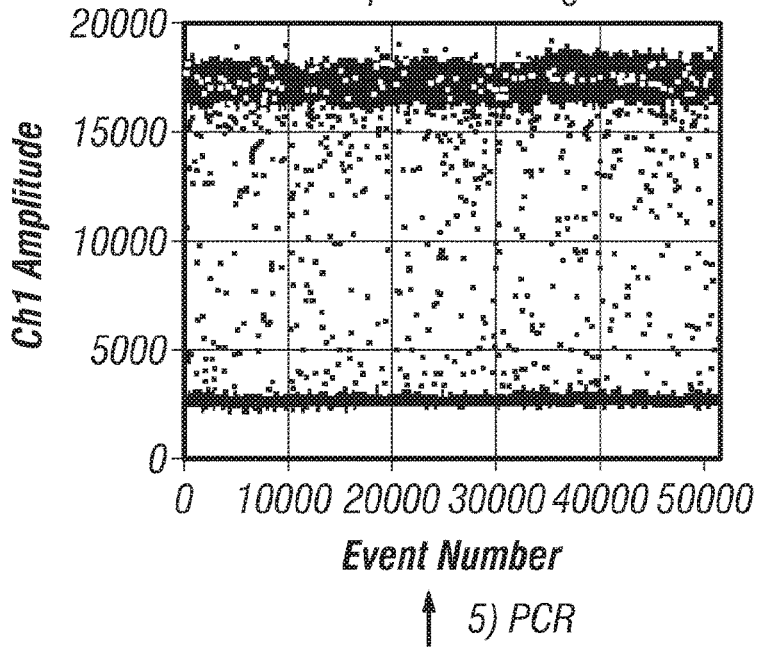
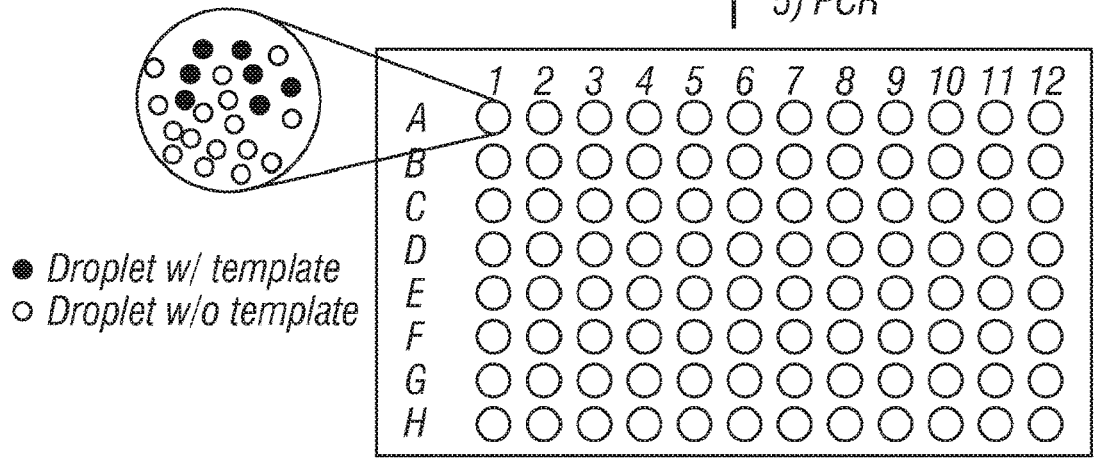
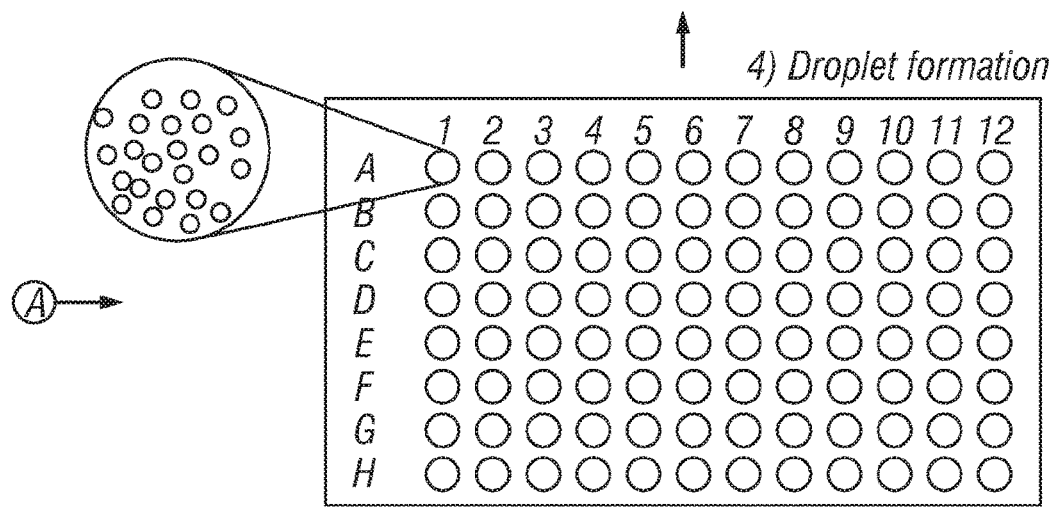
FIG. 15
(Cont'd)

and claims the benefit of U.S.
STOICHIOMETRIC NUCLEIC ACID PURIFICATION USING RANDOMER CAPTURE PROBE LIBRARIES This application is a national phase application under 35 U.S.C. § 371 of International Application No. PCT/US2017/031346 filed on May 5, 2017 and claims the benefit of U.S. Provisional Patent Application No. 62/332,778, filed May 6, 2016, the entirety of which is incorporated herein by reference.

Pursuant to 37 C.F.R. 1.821(c), a sequence listing is submitted herewith as an ASCII compliant text file named "RICEP0024US_ST25.txt", created on Mar. 12, 2019 and having a size of ~110 kilobytes. The content of the aforementioned file is hereby incorporated by reference in its entirety.

BACKGROUND

Technologies for writing (Gene Synthesis), editing (CRISPR/CAS) and reading (Next generation Sequencing-NGS) large collections of nucleic acids requires an enormous (>1000) number of oligonucleotides to be used as building blocks (writing), guides (editing) or hybridization probes and primers for doing highly multiplexed enrichment and sequencing (reading). It is not economical to synthesize, purify, and quantitate each oligonucleotide individually. Companies such as Agilent, NimbleGen, and Twist Biosciences have developed array-based synthesis platforms to allow highly multiplex DNA oligonucleotide synthesis, but the oligonucleotides synthesized by these platforms include truncation products. Because modern oligonucleotide synthesis occurs from 3' to 5', most impurity species are truncation oligonucleotide products lacking a number of nucleotides at the 5' end, followed by species with one or more internal deletions. In single-plex synthesis, these fraction of these impurity products can be reduced through post-synthesis high pressure liquid chromatography (HPLC) or polyacrylamide gel electrophoresis (PAGE) purification, but HPLC and PAGE cannot be used to purify a pool of many different oligonucleotides. Furthermore, HPLC and PAGE are time- and labor-intensive and cannot be easily automated to high throughput. Additionally, even single-plex HPLC and PAGE purification of oligonucleotides result only in below 90% purity of full-length oligonucleotide products.

The concentrations of different oligonucleotides in an array-synthesized pool will vary significantly based on oligonucleotide length, oligonucleotide sequence, and synthesis reagent age and purity. Consequently, oligonucleotides synthesis yields can vary by more than 16-fold from the same quantity of initial synthesis reagents. The variation in oligonucleotide concentrations can adversely affect downstream applications, e.g., in the production of long synthetic genes. In NGS, concentration variations in oligonucleotide pools used for hybrid-capture enrichment result in sequencing biases that cause significant wasted NGS reads.

SUMMARY

In accordance with the present disclosure, there is provided a method for generating a set of precursor nucleotide sequences comprising a target oligonucleotide molecule, wherein the precursor nucleotide sequence comprises a fifth region that comprises the nucleotide sequence of the target oligonucleotide molecule and a fourth region and a third region, wherein at least one of the fourth and third regions differs from any subsequence within the target oligonucleotide, the method comprising:

(i) calculating for the precursor nucleotide sequence the standard free energy of hybridization between the precursor nucleotide sequence and (a) a first oligonucleotide comprising a second region that is complementary to the third region of the precursor oligonucleotide sequence, and (b) a first region that is complementary to the fourth region of the precursor oligonucleotide sequence;

(ii) calculating the standard free energy of a capture reaction as the standard free energy of hybridization between the precursor nucleotide sequence and the first oligonucleotide and the standard free energy of hybridization between the first oligonucleotide and target oligonucleotide;

(iii) rejecting the precursor nucleotide sequence if the standard free energy of the capture reaction does not meet a certain criterion; and (iv) repeating steps (i) to (iii) until a set of precursor nucleotide sequences meets the criteria; and (v) producing the set of precursor nucleotide sequences. The criteria may be a negative free energy;

In another embodiment, there is provided a method for producing a set pf precursor nucleotide sequences comprising a plurality of barcode sequences, comprising:

(i) generating a set of precursor nucleotide sequences comprising each target oligonucleotide molecule, wherein each precursor nucleotide sequence comprises a third region that is conserved across all precursor nucleotide sequences, a fourth region that is unique for each target oligonucleotide molecule, and an fifth region that comprises the nucleotide sequence of a target oligonucleotide molecule;

(ii) calculating for each precursor nucleotide sequence the standard free energy of hybridization between the precursor nucleotide sequence and (a) a first oligonucleotide, comprising a second region that is complementary to the third region of the precursor oligonucleotide sequence, and (b) a first region that is complementary to the fourth region of the precursor oligonucleotide sequence;

(iii) calculating for each precursor nucleotide sequence the standard free energy of hybridization of folding;

(iv) calculating the standard free energy of a capture reaction as the standard free energy of hybridization between the precursor nucleotide sequence and the first oligonucleotide and the standard free energy of folding of the first oligonucleotide and the standard free energy of folding of the precursor oligonucleotide;

(v) rejecting the set of precursor nucleotide sequences if the standard free energy of the capture reaction for any precursor nucleotide sequence exceeds a certain criteria;

(vi) repeating steps (i) to (v) until a set of precursor nucleotide sequences meets the criteria; and (vii) producing said set of precursor nucleotide sequences.

The criteria may be a selected from the group consisting of a maximum range of standard free energies of capture, a standard deviation of standard free energies of capture, and a difference between two ranks in a sorted list. The criteria may be a maximum range of no more than 5 kcal/mol between a lowest standard free energy of capture and a highest standard free energy of capture for the set of precursor nucleotide sequences. The maximum range may be no more than 2 kcal/mol.

In yet another embodiment, there is provided a method for purifying one or multiple target nucleic acid molecules from a sample comprising one or a plurality of species of precursor molecules, wherein each species of precursor molecule comprises an fifth region comprising a target nucleic acid molecule sequence, a fourth region comprising a sequence unique to the species of precursor molecule in the plurality of species of precursor molecules, defined as a barcode sequence of length n, wherein 2ⁿ is greater than or equal to the number of unique target nucleic acid molecule sequences, a third region that is conserved across all precursor molecules, the method comprising:
  contacting the sample with a capture probe library at temperature and buffer conditions conducive to hybridization;
  wherein the capture probe library comprises a plurality of capture probe species, wherein each capture probe species comprises a first oligonucleotide comprising a first region comprising a nucleotide sequence of n nucleotides in length and a second region that is conserved across all capture probe species, wherein each nucleotide in the nucleotide sequence of n nucleotides in length is selected from two or more nucleotides and the first region is unique to each capture probe, and wherein the second region is complementary to the third region, and wherein the fourth region of each species of precursor molecule is complementary to the first region of a species of precursor molecule;
  separating the plurality of species of precursor molecules hybridized to the plurality of capture probe species from the species of precursor molecules not hybridized to the plurality of capture probe species;
  treating the plurality of species of precursor molecules hybridized to the plurality of capture probe species with a cleavage agent sufficient to site-specifically cleave the plurality;
  of species of precursor molecules at a site to separate the fifth regions from at least a portion of the third and fourth regions;
  recovering the fifth regions from the plurality of capture probe species and the at least a portion of the third and fourth regions, and thereby producing a purified target nucleic acid molecule or molecules.

Each capture probe species may further comprise a second oligonucleotide comprising a ninth region, wherein the ninth region is complementary to the second region. Each first oligonucleotide may further comprise a seventh region, each second oligonucleotide further comprises an eight region, and wherein the seventh region is complementary to the eight region. Each first oligonucleotide further may comprise a chemical moiety, and wherein the separating the plurality of species of precursor molecules hybridized to the plurality of capture probe species comprises surface capture of the chemical moiety. The chemical moiety may be selected from the group consisting of biotin, a thiol, an azide, an alkyne, a primary amine and a lipid. The first nucleotide hybridized with the precursor oligonucleotide may be the preferred ligand of an antibody or other receptor that mediate the surface capture of the complexes.

Recovering the fifth regions from the plurality of capture probe species and the at least a portion of the third and fourth regions may comprise a treatment selected from the group consisting of heating, introducing denaturants, washing with low salinity buffers, and introducing a nuclease. The site-specific cleavage may comprise a treatment selected from the group consisting of changing the temperature, changing the pH, and illuminating the plurality of species of precursor molecules hybridized to the plurality of capture probe species at a specific wavelength. The standard free energies of binding between each first oligonucleotide and a DNA sequence complementary to the entire sequence of the first oligonucleotide may be within 5 kcal/mol of each other. The two or more nucleotides at each nucleotide in the nucleotide sequence of n nucleotides in length maybe A or T, or may be G or C. The two or more nucleotides at each nucleotide in the nucleotide sequence of n nucleotides in length may be G or C for one or more nucleotides in the nucleotide sequence and A or T for one more nucleotides in the nucleotide sequence. The first region may comprise between 3 and 25 nucleotides. n may be between 3 and 60, 3 and 18, or 3 and 10 and not greater than the number of nucleotides in the first region. The first region may further comprise at least one nucleotide in addition to the nucleotide sequence of n nucleotides in length. The second region may further comprise between 8 and 200 nucleotides.

The barcode sequence of each species of precursor molecule is assigned based on a method comprising:
  generating a set of precursor nucleotide sequences comprising each target oligonucleotide molecule, wherein each precursor nucleotide sequence comprises a third region that is conserved across all precursor nucleotide sequences, a fourth region that is unique for each target oligonucleotide molecule, and an fifth region that comprises the nucleotide sequence of the target oligonucleotide molecule;
  calculating for each precursor nucleotide sequence the standard free energy of hybridization between the precursor nucleotide sequence and a first oligonucleotide, comprising a second region that is complementary to the third region of the precursor oligonucleotide sequence, and a first region that is complementary to the fourth region of the precursor oligonucleotide sequence;
  calculating for each precursor nucleotide sequence the standard free energy of hybridization of folding;
  calculating the standard free energy of a capture reaction as the standard free energy of hybridization between the precursor nucleotide sequence and the first oligonucleotide and the standard free energy of folding of the first oligonucleotide and the standard free energy of folding of the precursor oligonucleotide;
  rejecting the set of precursor nucleotide sequences if the standard free energy of the capture reaction for any precursor nucleotide sequence exceeds a certain criteria; and
  repeating the method until a set of precursor nucleotide sequences meets the criteria.

In still yet another embodiment, there is provided a capture probe library comprising: a plurality of oligonucleotides comprising a first plurality of oligonucleotides wherein each oligonucleotide of the first plurality of oligonucleotides comprises:
  a first region comprising a first nucleotide sequence comprising at least 3 variable positions, wherein each variable position comprises a nucleotide selected from at least two possible nucleotides,
  wherein the first nucleotide sequence comprising at least 3 variable positions is unique to each oligonucleotide, and
  a second region comprising a second nucleotide sequence, wherein the second nucleotide sequence of the second region is conserved across each oligonucleotide in the first plurality of oligonucleotides, A capture probe library comprising:
a plurality of oligonucleotides comprising a first plurality of oligonucleotides and a second plurality of oligonucleotides, wherein each oligonucleotide in the first plurality of species of oligonucleotides comprises
a first region comprising a nucleotide sequence comprising at least 3 variable positions, wherein each variable position comprises a nucleotide selected from at least two possible nucleotides,
wherein the nucleotide sequence comprising at least 3 variable positions is unique to each species of oligonucleotide, and
a second region comprising a nucleotide sequence, wherein the nucleotide sequence of the second region is conserved across each oligonucleotide in the first plurality of oligonucleotides,
wherein each oligonucleotide in the second plurality of oligonucleotides comprises a third region, wherein the third region is complementary to the second region.

The standard free energies of binding between each oligonucleotide in the first plurality of oligonucleotides and a DNA sequence complementary to the entire sequence of the respective oligonucleotide in the first plurality of oligonucleotides may be within 5 kcal/mol of each other. The at least two possible nucleotides at each nucleotide in may be A or T, or may be G or C. The at least two possible nucleotides at each nucleotide in may be G or C for one or more nucleotides in the nucleotide sequence and A or T for one more nucleotides in the nucleotide sequence. The concentration of a second oligonucleotide may be greater than a sum of the concentrations of each oligonucleotide of the first plurality of oligonucleotides. The first region may comprise between 3 and 25 nucleotides. The number of variable positions in the first region may be between 3 and 60, between 3 and 18, or between 3 and 10, and not greater than a total number of nucleotides in the first region. The first region further may comprise at least one nucleotide in addition to the at least 3 variable positions. The second region may comprise between 8 and 200 nucleotides. The at least three variable regions may be contiguous or non-contiguous.

A further embodiment comprise an oligonucleotide library for the multiplexed capture of a set of desired precursor nucleic acid molecules comprising:
a plurality of species of precursor molecules, wherein each species of precursor molecule comprises
a third region comprising a nucleotide sequence that is conserved across all species of precursor molecules,
a fourth region comprising a barcode sequence comprising 3-60 nucleotides, an fifth region comprising a target nucleic acid molecule sequence that is unique to the species of precursor molecule in the plurality of species of precursor molecules, wherein the barcode sequence of each species of precursor molecule is different and wherein 2n is greater than or equal to the number of unique target nucleic acid molecule sequences; and
a capture probe library comprising a plurality of capture probe species, wherein each capture probe species comprises an oligonucleotide comprising a first region comprising a nucleotide sequence of n nucleotides in length, a second region that is conserved across all capture probe species, wherein each nucleotide in the nucleotide sequence of n nucleotides in length is selected from two or more nucleotides and the first region is unique to each capture probe, and wherein the second region is complementary to the third region, and wherein the fourth region of each species of precursor molecule is complementary to the first region of a species of precursor molecule.

The standard free energies of binding between each species of first oligonucleotide in the plurality of capture probe species and a DNA sequence complementary to the entire sequence of the respective species of first oligonucleotide may be within 5 kcal/mol of each other. The two or more nucleotides at each nucleotide in the nucleotide sequence of n nucleotides in length may be A or T, or may be G or C. The two or more nucleotides at each nucleotide in the nucleotide sequence of n nucleotides in length may be G or C for one or more nucleotides in the nucleotide sequence and A or T for one more nucleotides in the nucleotide sequence.

The a concentration of a second oligonucleotide may be greater than a sum of the concentrations of each species of first oligonucleotide. The first region may comprise between 3 and 25 nucleotides. n may be between 3 and 60, 3 and 18, or 3 and 10, and not greater than the number of nucleotides in the first region. The first region may further comprise at least one nucleotide in addition to the nucleotide sequence of n nucleotides in length. The second region may comprise between 8 and 200 nucleotides. The barcode sequence of each species of precursor molecule may be selected based on the method as set forth above. The at least one species of precursor molecule may be chemically synthesized or produced enzymatically. The enzyme used to produce the at least one species of precursor molecule may be a ligase or a polymerase.

In an additional embodiment, there is provided a method for purifying multiple target nucleic acid molecules from a sample comprising a plurality of precursor molecules, wherein the method comprises the steps of:
providing a plurality of nucleic acid probes, wherein each probe has a sequence complementary to a region of one of the precursor molecules and a first moiety sufficient to allow isolation of the probe;
adding the plurality of nucleic acid probes to a sample comprising the plurality of precursor molecules under conditions sufficient to promote hybridization of each nucleic acid probe to the region of the precursor molecule complimentary to the sequence thereby forming a plurality of probe-precursor complexes, wherein each precursor molecule comprises a different target nucleic acid molecule, and wherein the region of each precursor molecule does not comprise the target nucleic acid molecule; and
isolating the plurality of probe-precursor complexes via interaction with the first separating the target nucleic acid molecules from the plurality of probe-precursor.

Another embodiment provides for a method for producing a plurality of distinct target oligonucleotides each having a specified sequence, the method comprising:
(1) synthesizing a precursor oligonucleotide for each distinct target oligonucleotide, wherein the precursor comprises a third sequence, a fourth sequence, and a fifth sequence, wherein the third sequence is identical for all precursors, the fourth sequence comprises a barcode and is distinct for all precursors, and a fifth sequence corresponds to the target sequence,
(2) synthesizing a capture probe library of distinct oligonucleotides comprising a first sequence and a second sequence, wherein the first sequence comprises degenerate randomer nucleotides and wherein at least one first sequence is complementary to each fourth sequence, and the second sequence is complementary to the third sequence, (3) mixing the precursors and the capture probe library in an aqueous hybridization buffer,
(4) removing precursor molecules not bound to the capture probes,
(5) enzymatically or chemically cleaving the fifth sequence from the remainder of the precursor molecules, and
(6) removing the capture probe library and the remainder of the precursor molecules.

The first sequence may comprise an S degenerate nucleotide at certain positions and/or a W degenerate nucleotide at certain positions, but may not comprise an N degenerate nucleotide at any position, such that any degenerate variant of the first sequence is complementary to one or more fourth sequences, wherein S is a strong base, W is a weak base, and N is any base. The capture probes may be functionalized with a moiety permitting for rapid binding to a ligand, such as a moiety selected from a biotin, a thiol, an azide, or an alkyne. In step (4), eliminating precursor molecules not bound to capture probes may comprise adding particles that specifically bind the capture probe, followed by removal of supernatant solution. The particles may be selected from streptavidin-coated magnetic beads or streptavidin-coated agarose beads. The precursors may further comprise a deoxyuracil nucleotide or an RNA nucleotide, and cleavage of the fifth sequence comprises introduction of a uracil DNA glycosylase or an RNAse enzyme. The precursors may further comprise a photolabile or heat-labile moiety, and the cleaving of the fifth sequence comprises exposure of the solution to light of the appropriate wavelength or heating to the appropriate temperature. The fourth sequence may further comprise the "S" degenerate nucleotide at certain positions and/or the "W" degenerate nucleotide at certain positions, but does not comprise the "N" degenerate nucleotide at any position. The length of the first sequence may be between 5 and 50 nucleotides, and wherein the number of degenerate nucleotides is between 1 and 30, between 1 and 20, between 1 and 10, between 2 and 8, between 2 and 6, or between 3 and 5. The length of the second sequence may be between 5 and 50 nucleotides, and/or wherein the length of each target oligonucleotide is between 5 and 500 nucleotides.

In an additional embodiment, there is provided an oligonucleotide capture probe library comprising a first sequence and a second sequence, wherein the first sequence comprises degenerate randomer nucleotides comprising an "S" degenerate nucleotide at one or more positions and/or a "W" degenerate nucleotide at one or more positions, but does not comprise an "N" degenerate nucleotide at any position, and wherein the length of the first sequence is between 5 and 50 nucleotides, the number of degenerate nucleotides is between 1 and 30, and the length of the second sequence is between 5 and 50 nucleotides. The second sequence may comprise an "S" degenerate nucleotide at certain positions and/or a "W" degenerate nucleotide at certain positions, but does not comprise a "N" degenerate nucleotide at any position. The oligonucleotide capture probe library may be functionalized with a chemical moiety for rapid binding, selected from a biotin, a thiol, an azide, or an alkyne. The one or more of the oligonucleotide capture probes may further comprise a deoxyuracil nucleotide or an RNA nucleotide. The one or more of the oligonucleotide capture probes may further comprise a photolabile or heat-labile moiety. The length of the first sequence may be between 5 and 50 nucleotides, and wherein the number of degenerate nucleotides may be between 1 and 30. The length of the second sequence may be between 5 and 50 nucleotides. The library may have at least 8, at least 32, or at least 256 members. The library may have between 8 and 32 members, between 8 and 256 members, between 32 and 256 members, between 8 and 1024 members, between 32 and 1024 members, or between 256 and 1024 members. The library may be found on one or more substrates.

In still an additional embodiment, there is provided an aqueous solution comprising an oligonucleotide capture probe library, a plurality of precursor oligonucleotides and a set of precursor oligonucleotides, wherein:
the capture probe library comprises a first sequence and a second sequence, wherein
the first sequence comprises degenerate randomer nucleotides comprising an "S" degenerate nucleotide at certain positions and/or an "W" degenerate nucleotide at certain positions, but does not comprise an "N" degenerate nucleotide at any position, and wherein the length of the first sequence is between 5 and 50 nucleotides, the number of degenerate nucleotides is between 1 and 30, and the length of the second sequence is between 5 and 50 nucleotides,
each of the plurality of precursor oligonucleotides comprises a third sequence, a fourth sequence, and a fifth sequence, wherein the third sequence is identical for all precursors, the fourth sequence comprises a barcode and is distinct for all precursors, the second sequence is complementary to the third sequence, and at least one instance of a first sequence is complementary to each fourth sequence.

The second sequence of the oligonucleotide capture probe library may comprise an "S" degenerate nucleotide at certain positions and/or a "W" degenerate nucleotide at certain positions, but may not comprise a "N" degenerate nucleotide at any position. The oligonucleotide capture probe library may be functionalized with a chemical moiety for rapid binding, selected from a biotin, a thiol, an azide, or an alkyne. The one or more of the oligonucleotide capture probes further may comprise a deoxyuracil nucleotide or an RNA nucleotide. The one or more of the oligonucleotide capture probes may further comprise a photolabile or heat-labile moiety. The length of the first sequence of the oligonucleotide capture probe library may be between 5 and 50 nucleotides, and the number of degenerate nucleotides may be between 1 and 30. The length of the second sequence of the oligonucleotide capture probe library may be between 5 and 50 nucleotides. The oligonucleotide capture probe library may have at least 8, at least 32, or at least 256 members. The oligonucleotide capture probe library may have between 8 and 32 members, between 8 and 256 members, between 32 and 256 members, between 8 and 1024 members, between 32 and 1024 members, or between 256 and 1024 members. The oligonucleotide capture probe library may be found on one or more substrates. The precursors may further comprise a deoxyuracil nucleotide or an RNA nucleotide, and cleavage of the fifth sequence comprises introduction of a uracil DNA glycosylase or an RNAse enzyme.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 5: Use of multiple barcodes for the same target sequence increases its concentration in the final purified mixture. Degenerate nucleotides (i.e., S=G or C and W=A or T) within the barcode region 4 facilitates the achievement of arbitrary desired stoichiometric ratios of targets by avoiding individual synthesis of a number numbers of precursor oligonucleotides. (SEQ ID NOS: 418-421)

(FIG. 7A) Next Generation Sequencing was used to characterize the purity of the 64 oligos, where the purity is operationally defined as the number of perfectly aligned reads divided by the number of reads aligned by Bowtie 2. The purity of the SNAP products are significantly higher than that of individually PAGE purified oligonucleotides (median 79% vs. 61%). (FIG. 7B) Digital droplet PCR was used to evaluate the stoichiometries of the 64 SNAP product oligonucleotides.

DETAILED DESCRIPTION

Figure 1:
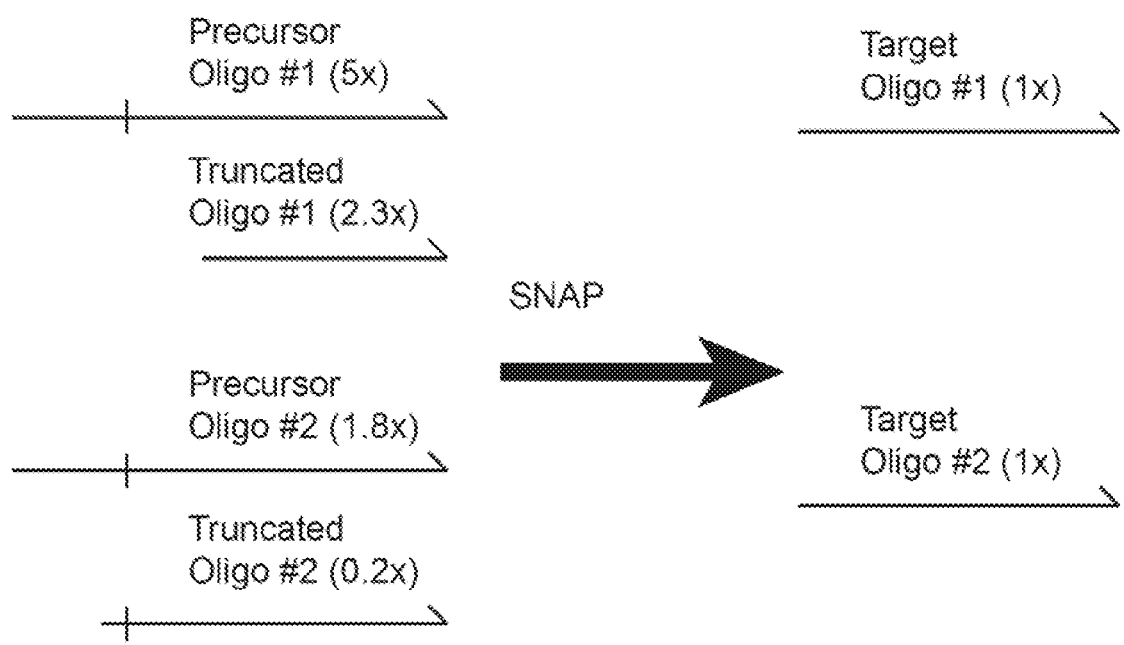
FIG. 1: Schematic overview of one embodiment of Stoichiometric Nucleic Acid Purification (SNAP). A sample mixture containing two precursors of oligonucleotide targets also contains a number of truncation synthesis products that are not desired. Through the course of the method described in this disclosure, full length target oligonucleotides are produced in roughly equal stoichiometry.

The goal of this disclosure is outlined shown in FIG. 1: different precursor oligonucleotides are synthesized with various yields and purities, and pooled together to form an input oligonucleotide pool. Through a process of SNAP purification, an output pool of target oligonucleotides is produced with no truncation products, and exhibiting a desired stoichiometric ratio (1:1 in FIG. 1).

In certain aspects of the present disclosure, toehold probes with a randomer toehold sequence are used to capture artificially designed 5' sequence of the target oligonucleotides. Because the probes are toehold probes which are selective to single nucleotide variations, even truncated synthesis products one nucleotide shorter than the full-length product will not be efficiently captures.

I. PRECURSOR OLIGONUCLEOTIDES

Figure 2:
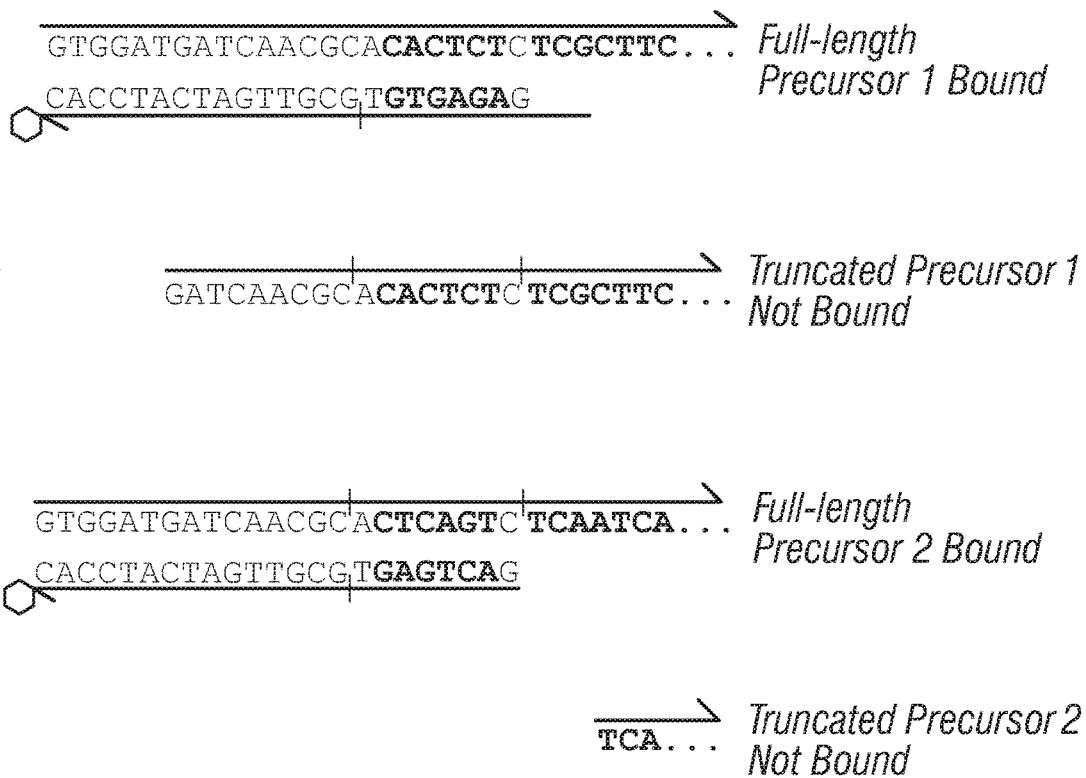
FIG. 2: Schematic of a capture probe library and corresponding set of target sequences. Within the targets libraries, region 3 is conserved while regions 4 and 5 are different for each target sequence. Similarly, within a library of capture probes region 2 is conserved, while region 1 contains variable positions with two or more nucleosides being possibly present at each variable position. (SEQ ID NOS: 404-409)

A full-length precursor oligonucleotide comprises three regions, labeled as 3, 4, and 5 in FIG. 2. Region 3 is also referred to as the validation region, and the sequence of region 3 is conserved across all precursor species. Region 4 is also referred to as the barcode, and the sequence of region 5 is unique to each precursor species. Region 5 is referred to as the target sequence, and is the only portion of the oligonucleotide that should remain after the purification process. Across different precursor species, some region 8's may be unique, while others may be redundant. In some embodiments, the nucleotide to the 5' of region 5 is a modified nucleotide (e.g., a deoxyuracil nucleotide, or an RNA nucleotide) that can be site-specifically cleaved.

Because DNA synthesis (both chemical and enzymatic) is imperfect, there will exist truncation products in which precursors lack one or more nucleotides at either the 5' end (chemical synthesis) or the 3' end (enzymatic synthesis).

II. CAPTURE PROBE LIBRARY

FIG. 2 shows one preferred embodiment of the capture probe library used to perform SNAP purification for chemically synthesized oligonucleotides with truncations at the 5' end. In this embodiment, the library comprises two types of oligonucleotides: the probe oligonucleotides (comprising regions 1 and 2). In certain aspects, the probe oligonucleotides are functionalized at the 3' end with a biotin, in order to allow capture by streptavidin-functionalized magnetic beads.

The sequence of region 1 is designed and synthesized as a randomer library, in which one or several positions contain a mixture of multiple nucleotides. The complement of every precursor species' barcode (region 4) should exist as an instance of the region 1 randomer library.

The sequence of region 2 is designed to be complementary to the sequence of region 3 on precursors.

III. SEQUENCE DESIGN OF RANDOMER REGION 1

The variable positions and allowable nucleotides at each variable position should be designed such that the standard free energy of hybridization of each instance region 1 to its perfect complement are similar. In some embodiments, the sequence of region 1 comprises S (strong, mixture of G and C) and W (weak, mixture of A and T) degenerate nucleotides.

As one example of an undesirable sequence construction, if region 4 is designed as a 7nt NNNNNNN region, then both GCGCGCG and TATATAT members will be present. The $\Delta Go$ of these two members pairing with their complements at 37° C. in 1M Na+ are −13.23 kcal/mol and −4.38 kcal/mol, respectively, according to SantaLucia Jr, J., & Hicks, D. (2004). The thermodynamics of DNA structural motifs. Annu. Rev. Biophys. Biomol. Struct., 33, 415-440. This 9 kcal/mol difference can result in the GCGCGCG member capturing its target with >99.9% yield while the TATATAT member capturing its target with <0.1% yield; such a large difference in capture yield would be clearly undesirable for achieving uniform or ratiometric product quantity/concentration distributions.

For this reason, the nucleosides present at variable positions are designed to be either S or W. That is to say, some variable positions contain either an A or T nucleoside but not G or C, while other variable positions contains G or C but not A or T. Based on published literature parameters, there is only a maximum difference of 0.17 kcal/mol per base stack for SW and for WS stacks, at 37° C. in 1M Na+.

IV. SEQUENCE-SPECIFIC CAPTURE

In those instances where the number of different probes is equal the number of the target sequences, and the total concentration of probes is lower than the total concentration of target, any instance of region 1 only hybridizes to its perfectly complement in region 4, as any other non-specific hybridization will be outcompeted.

Consequently, if the probe oligonucleotide library is synthesized such that all instance sequences are equally represented, and if the concentration of all precursors exceed that of their corresponding probe sequences, then the amount of precursor captured should be roughly stoichiometric, regardless of the initial stoichiometric ratio between the precursors. As a numerical example, if the sequence of region 1 is "GWSWSWST", then there are $2^6$=64 instance sequences. Assuming a total probe concentration of 6.4 µM, each sequence instance would have a concentration of approximately 100 nM. For an initial precursor pool in which the concentrations of each precursor species ranges between 200 nM and 10 µM, the amount of each precursor bound to the probe will be limited by probe instance sequence concentration to a maximum of 100 nM, except insofar as off-target hybridization between precursors and their non-cognate probe instance sequences hybridize.

As another mathematical example, a probe library with 12 variable position, and 2 possible nucleotides at each position is comprised of $2^{12}$=4096 members. Assuming a total amount of 4 nanomoles (nmol) of the library, each member is expected to be present at quantity of roughly 1 pmol. This library is suitable for purification of up to 4096 targets, each with quantity of ≥10 pmol. Array oligonucleotide synthesis providers often produce panels of oligonucleotides at either the 10 pmol or 100 pmol scale.

V. SEPARATION OF PRECURSORS BOUNDED TO PROBES

The precursor oligonucleotides bound to the probe oligonucleotides are separated from other precursors using the probes as marker for recovery, through the use of a solid support or enzymatic degradation of unbound molecules, for example, using an exonuclease (e.g., 5'-3') for single-strand digestion. In a particular embodiment, the probe oligonucleotides are biotin-functionalized at the 3' end, and streptavidin-functionalized magnetic beads are added to solution after the hybridization reaction between the precursors, protectors, and probes. Washing the magnetic bead suspension in the vicinity of a magnet removes unbound molecules.

VI. REMOVAL OF REGIONS 3 AND 4 FROM TARGETS

Figure 4:
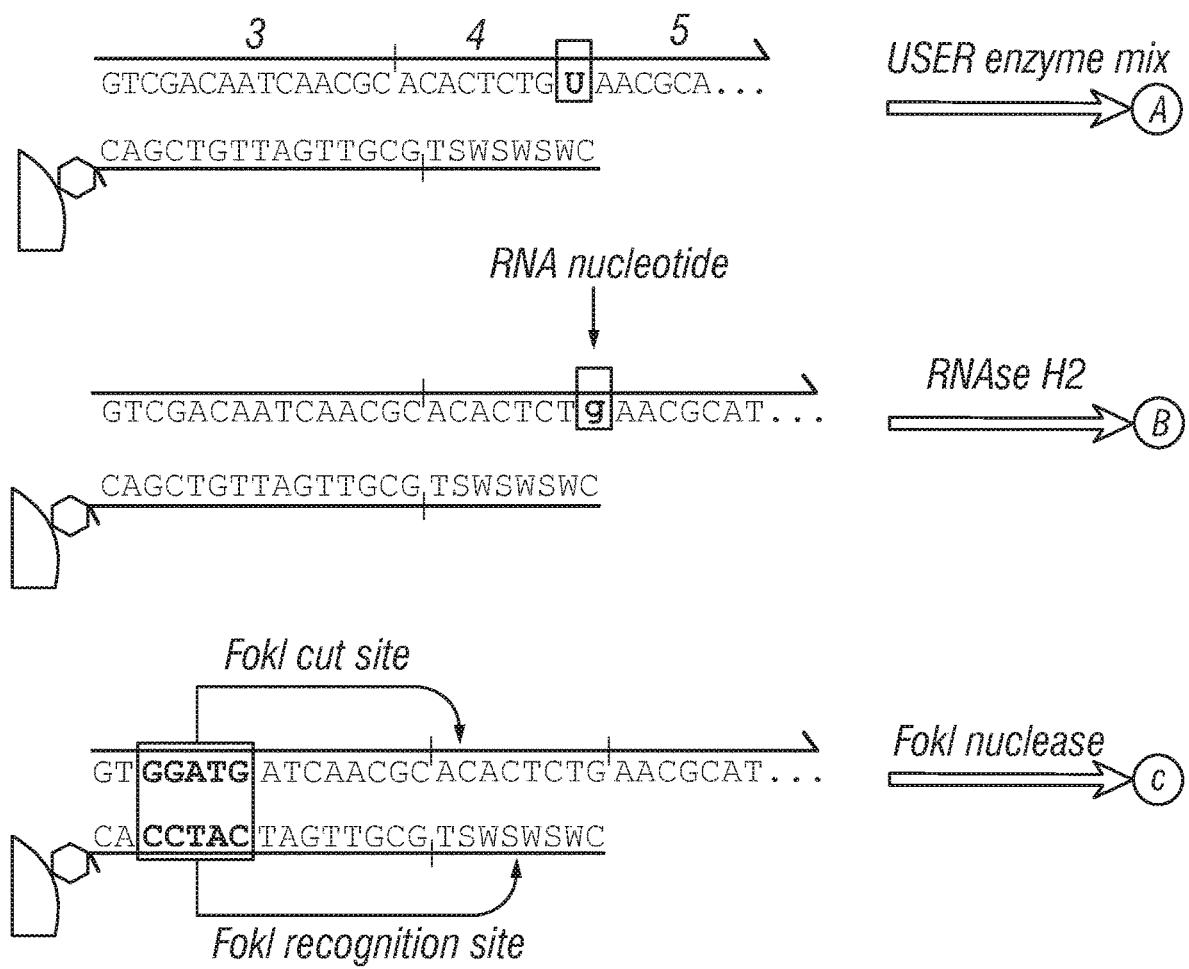
FIG. 4: Removal of regions 3 and 4 from target sequences using an enzyme. The desired region 5 can be enzymatically cleaved from the 5' regions 3 and 4 used for purification, for applications where such sequences are undesirable. Site-specific cleavage can be implemented through use of (a) uracil DNA glycosylase alone or in a formulation containing DNA glycosylase-lyase Endonuclease VIII—commercially known as USER, (b) RNAse, (c) FokI endonuclease, or other methods known to one of ordinary skill in the art. The sequence or chemical composition of regions 3 and 4 may be adapted to accommodate the anticipated enzymatic cleavage process. (SEQ ID NOS: 410-417 and 251)
Figure 4:
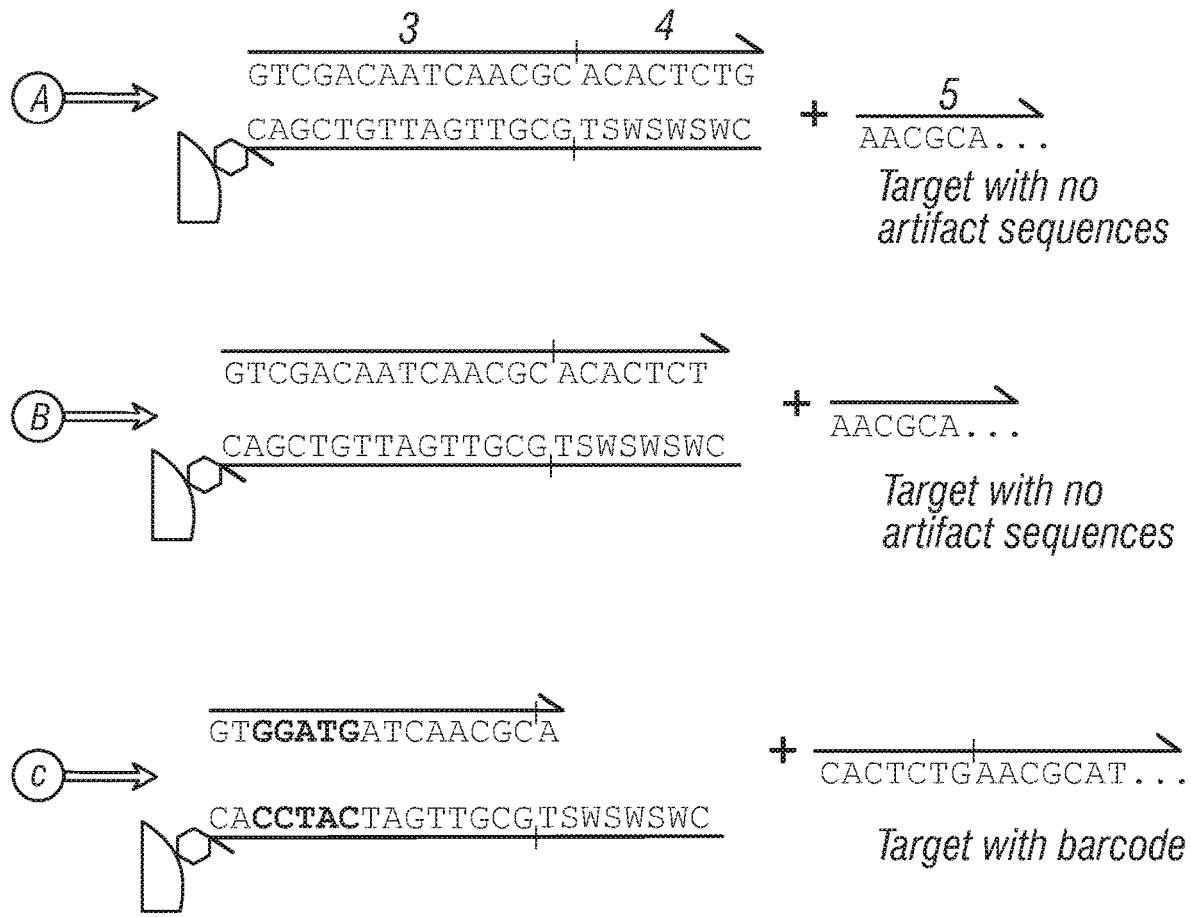

For many applications with purified pools of target oligonucleotides, the sequences of regions 3 and 4 would be an undesirable artifact. The sequence or composition of these regions may be designed to facilitate enzymatic removal of these regions from the desired target sequence after surface-based purification. FIG. 4 shows several strategies for enzymatically cleaving the captured target sequences after region 4 to remove all artifact sequences, or after region 3 to remove the purification sequence but not the barcode.

VII. SNAP PURIFICATION WORKFLOW

Figure 3:
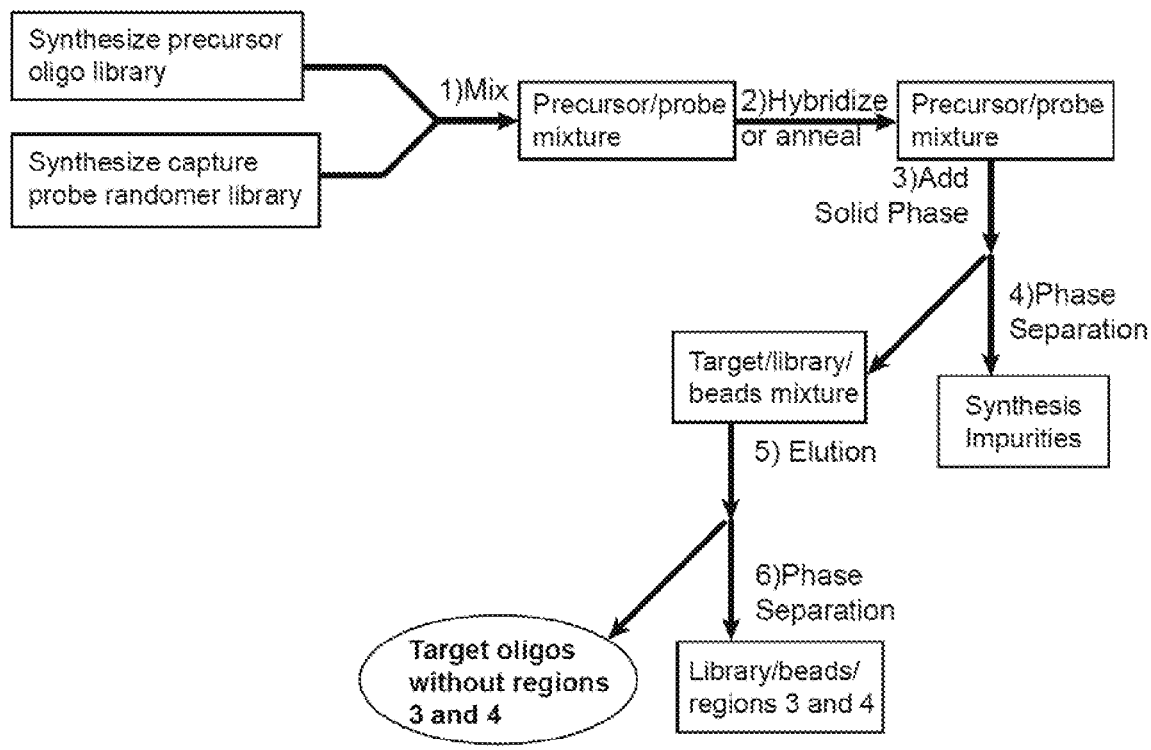
FIG. 3: Multiplexed oligonucleotide purification workflow. The process consists of 6 sequential steps. In step 3, solid phase consists of functionalized magnetic beads that enable the phase separation in steps 4 and 6. Depending on whether the user desires target sequences with or without the universal region 3 and barcode region 4, in step 5 either heat/NaOH denaturation or restriction enzyme cleavage can be used after the purification to separate the final products from the library and magnetic beads.

FIG. 3 shows one embodiment of the overall SNAP purification workflow. Hybridization durations, buffers, and temperatures vary depending on the concentration of the probe and precursor oligonucleotides, and reasonable parameter values are known to those ordinary in the art of nucleic acid hybridization probes. The capture of biotin-functionalized probes by magnetic beads and subsequent wash protocols are typically provided by suppliers of biotin-functionalized magnetic beads (e.g., Thermo Fisher Dynabeads, New England Biolabs streptavidin magnetic beads). The USER enzyme (e.g., from New England Biolabs) can be used to site-specifically cleave precursor oligonucleotides at dU positions.

VIII. RATIOMETRIC CONCENTRATIONS OF PURIFIED TARGETS

Through the use of multiple barcodes (region 4) for the same target sequence (region 5), it is possible to adjust the stoichiometric ratios of different target sequences after SNAP purification. FIG. 5 shows an example in which 3 different target sequences are sought to be purified in a 1:2:6 ratio.

The number of available barcodes based on variable positions determines the range of available stoichiometric ratios and number of sequences possible. For example, a probe library with 12 variable positions and 2 possible nucleotides at each position contains $2^{12}$=4096 sequence instances. The sum of all integer stoichiometry ratios among different target sequences must sum to 4096 (or less). For example, it is possible to purify a library of 2097 target sequences, in which 2096 target sequences are at equal stoichiometry to one another, and the last target sequence is present at 1000× excess.

Importantly, degenerate randomer sequences can also be incorporated in region 4 of the precursor sequences, in order to reduce the cost of precursor synthesis. For example, in FIG. 5, Target 2 occupies two sequence instances of the barcode through the use of a degenerate W in region 7.

In some instances, to yield uniform concentrations of target oligonucleotides in the final pool, the capture probe library should be at a significantly lower concentration than the input target oligonucleotide sample. For example, the full-length product of Target 1 is initially at 5 µM and the full-length product of Target 2 is initially at 8 µM, each member of the capture probe library should be kept below 5 µM, such as 1 µM. In such an instance, the purification yield may be lower than for HPLC and PAGE methods for single targets but will provide a uniform final concentration of target molecules. In instances where a uniform final target concentration is not needed, the yield will not be reduced in such a way.

IX. BARCODE ASSIGNMENT BASED ON TARGET SEQUENCE

To simultaneously achieve high sequence specificity and high hybridization yield, the standard free energies of hybridization (ΔG°Hyb) between the different precursor and their respective matched probe sequence instances must be similar. Naive design of the validation region sequence (region 3) and assignment of barcodes (region 4) may result in precursor oligonucleotides with significant secondary structure between region 5 and regions 3 and 4, resulting in ΔG°Hyb significantly more positive than expected, in turn leading to lower capture yields. Consequently, it is suggested that the sequences of regions 3 and 4 be rationally designed given desired target sequences, so that similar secondary structure is observed for all precursor sequences.

X. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Stoichiometric SNAP Purification

Figure 6:
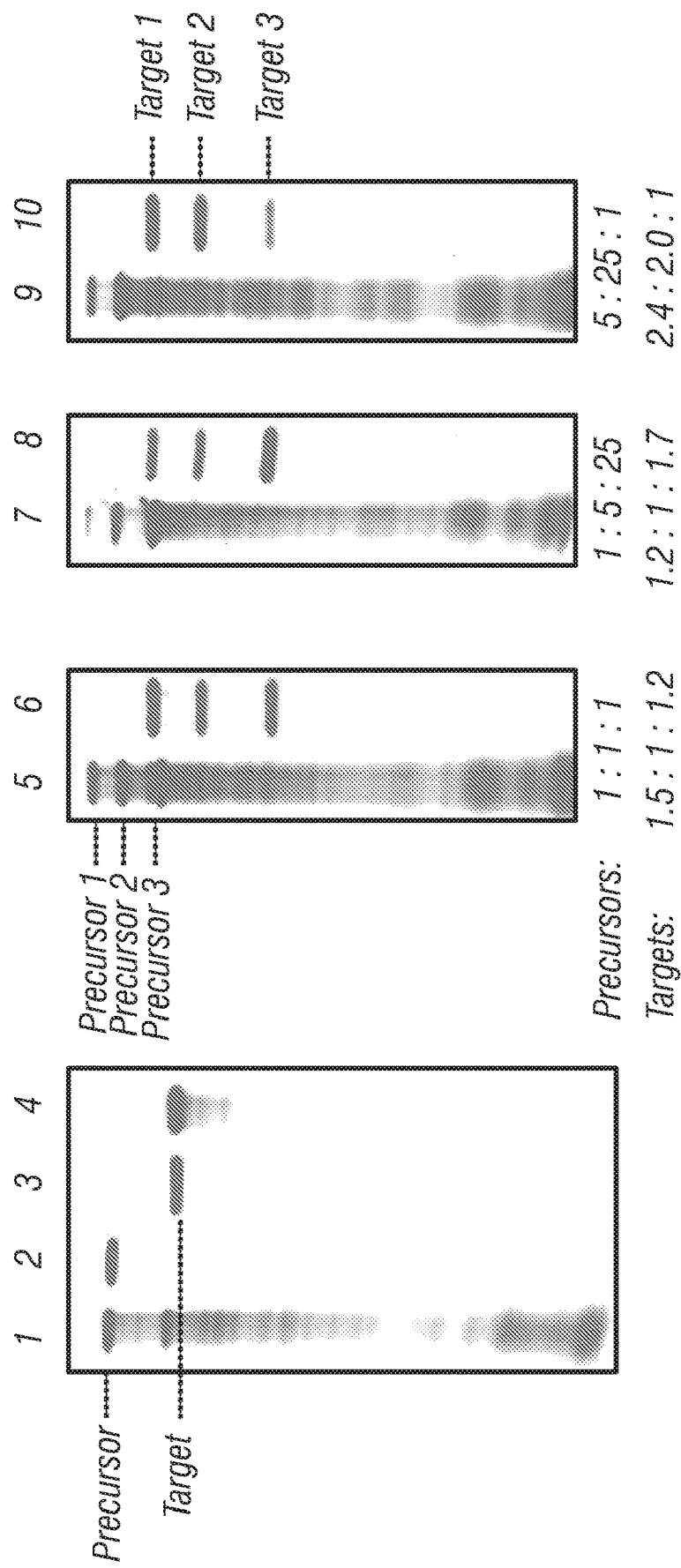
FIG. 6: Proof of concept results using fluorescent labelled oligonucleotides, assayed through fluorescent polyacrylamide gel electrophoresis. 160 pmol of a capture probe library biotinylated in 3' end, comprising 64 different region 1 sequences, is incubated with 64 synthetic unpurified precursor oligonucleotides each at 10 pmol. Each precursor oligonucleotide has a uniquely assigned region 4, complementary to one and only one instance of region 1 on the capture probe species. Lane 1 shows the length distribution of Precursor 1, and Lane 2 shows the length distribution of Precursor 1 after undergoing SNAP, but without cleavage of regions 3 and 4. Lane 3 shows the SNAP product after cleavage of regions 3 and 4. Lane 4 shows the length distribution of the corresponding commercially provided PAGE-purified oligo as comparison. Lanes 5-10 show that, regardless of initial stoichiometric ratio of the 3 Precursors, the final stoichiometry of the SNAP products are close to 1:1:1. The SNAP protocol used for this series of experiments is as follows: The capture probe library and Precursors are allowed to hybridize for 2 hr at 60° C. in 0.5M NaCl pH 7.5. Subsequently, 3 mg of streptavidin coated magnetic beads (pre-washed with the same incubation buffer) are added to the oligonucleotide mixture to a final volume of 100 µL, and incubated for 30 min at 60° C., with the sample being rocked by a shaker. The supernatant is then discarded and the magnetic beads are washed twice in the incubation buffer and one time in the buffer to be used for the subsequent enzymatic cleavage. For lane 2, the full-length precursors are eluted using 50% v/v formamide at 95° C. for 5 to 15 min For lane 3, the beads were re-suspended in USER buffer, and 2 enzymatic units of USER enzyme mix were added to achieve a final volume of 25 µL; this mix was then incubated for 1 hour at 37° C. Finally supernatant containing the desired purified target is extracted.

FIG. 6 shows data demonstrating proof-of-concept of the SNAP purification technique. Denaturing polyacrylamide gel electrophoresis is used to visualize and quantitate the purity and concentration of different oligonucleotide species. Lane 1 shows a chemically synthesized precursor oligonucleotide, and lane 4 shows the corresponding chemically synthesized target oligonucleotide. Both the precursor and the target oligonucleotides were synthesized with a 3' FAM fluorophore functionalization to allow easy visualization. Lanes 2 shows the captured precursor molecules before USER enzyme treatment to remove regions 3 and 4, and Lane 3 shows the final purified product after USER enzyme treatment. The relative lack of truncation bands in Lanes 2 and 3 indicate that truncation products have been removed.

Lane 5 shows a mixture of 3 precursor oligonucleotides of different lengths (100nt, 90nt, and 80nt), prepared at a nominal stoichiometric ratio of 1:1:1. Lane 6 shows the output of the SNAP purification protocol. The stoichiometric ratio of the purified target oligonucleotides was quantitated to be 1.2:1:1.5. Lane 7 and 8 show a similar set of experiments, except the 3 precursor oligonucleotides were nominally prepared at 1:5:25 and the SNAP-purified products were observed to be at 1.2:1:1.7, and is closer to the designed 1:1:1 stoichiometric than the precursors. Lane 9 and 10 show a similar set of experiments, except the 3 precursor oligonucleotides were nominally prepared at 5:25:1 and the SNAP-purified products were observed to be at 1.2:1:0.5.

Figure 7:
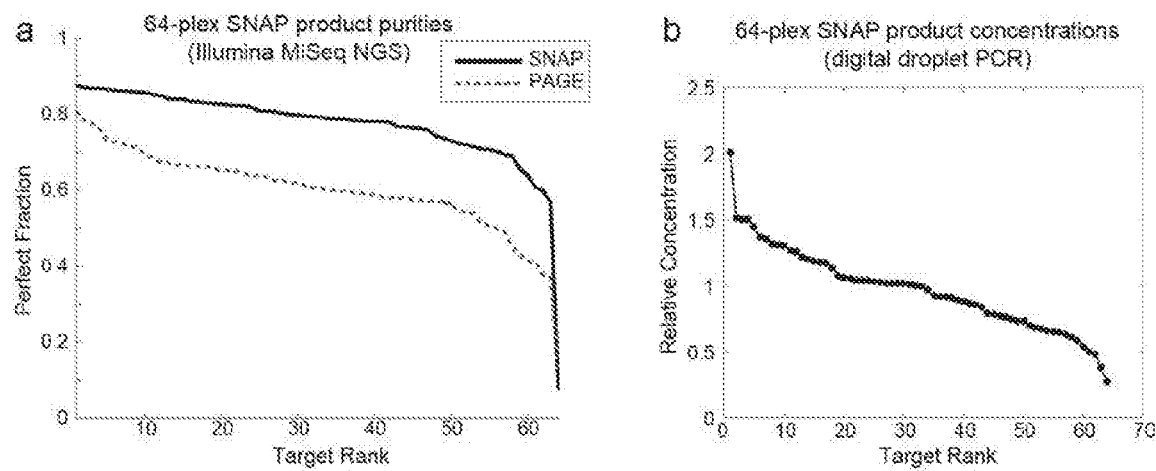
FIGS. 7A-B. Characterization of purity and stoichiometry for multiplexed SNAP. 64 separate Precursors (10 pmol each) were simultaneously purified via SNAP.

FIGS. 7A-B show data demonstrating purity and stoichiometry attainable by means of SNAP purification as measured by Next Generation Sequence and digital droplet PCR. FIG. 7A shows that the median of reads perfectly matching the desired sequence is about the 80%, in case of SNAP purification, which is greater that the median from PAGE purification which is about 60% and the one from unpurified oligos, which is about 55%. FIG. 7B shows the concentration of the individual sequences as measured through digital droplet PCR, using target specific primers. After the SNAP purification the concentration of the oligo is within a factor of two for the 95% of the sequences of the pool.

Figure 11:
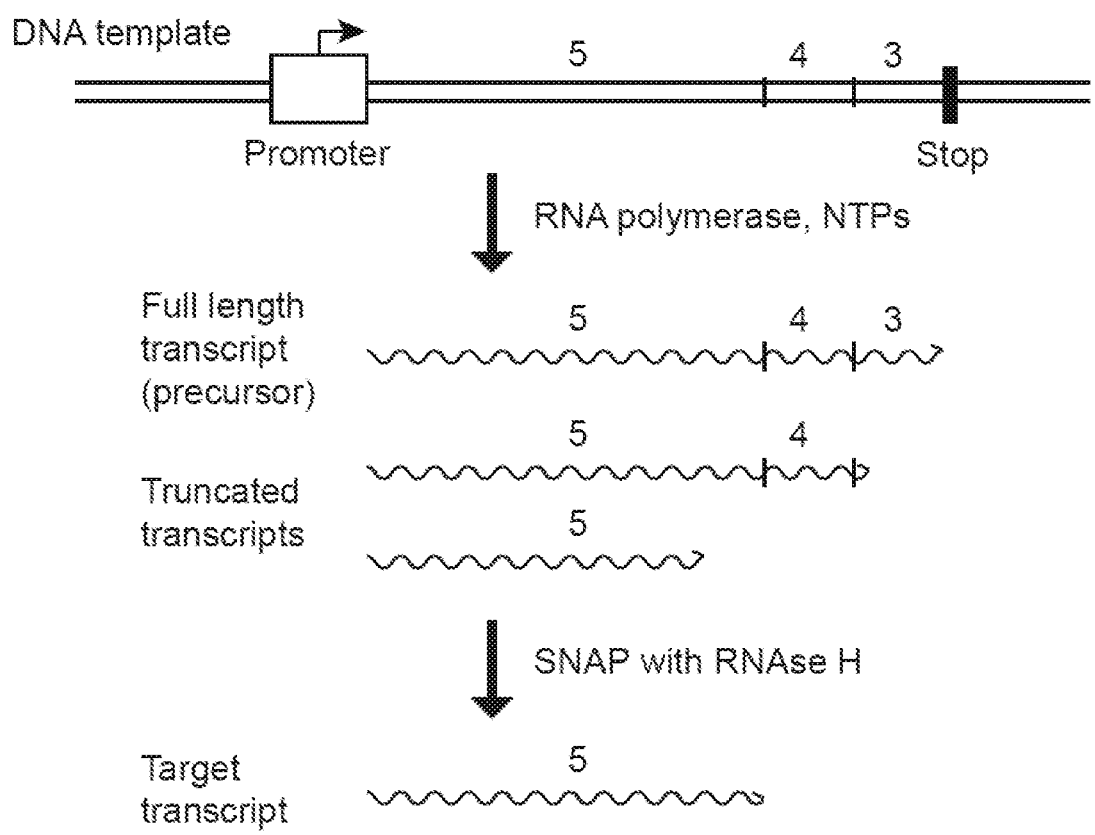
FIG. 11: Purification of RNA transcripts produced from a synthetic DNA template that comprises regions 3 and 4.
Figure 12:
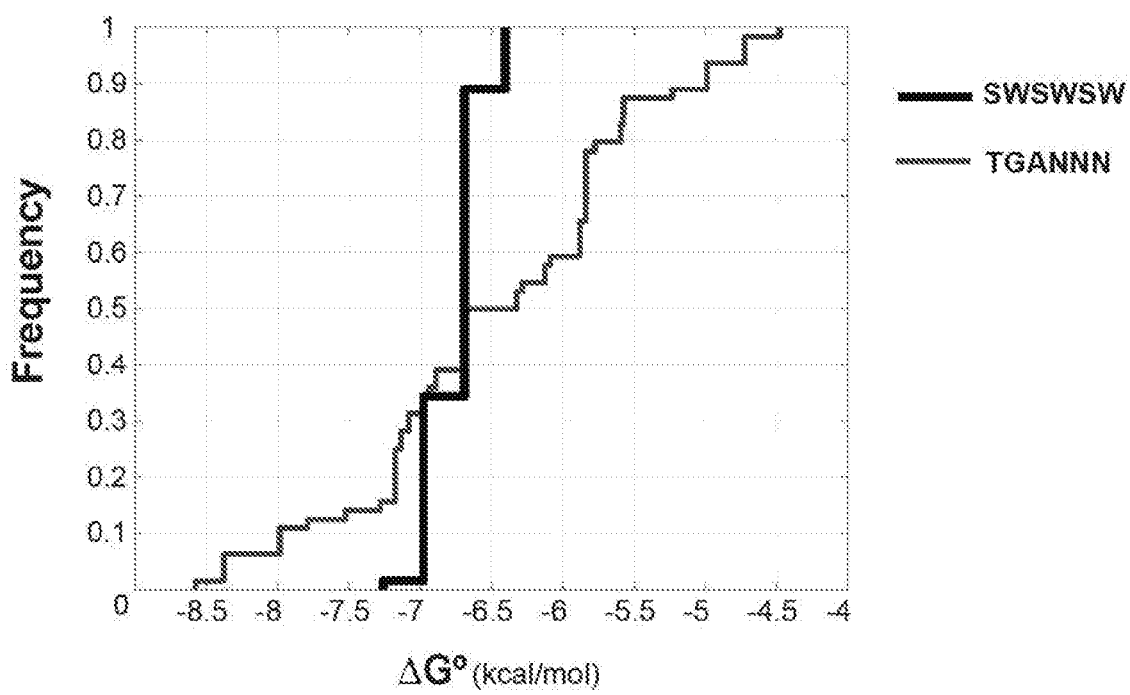
FIG. 12 Cumulative distribution of $\Delta G°_{rxn}$ for two different randomer sequences, each producing 64 instances. Using an SWSWSW library (flanked by CA in 5' end and C in 3' end) produces a tight thermodynamics range of 0.8 kcal/mol window. In contrast, using a TGANNN library results in a spread of more than 4 kcal/mol.
Figure 13A:
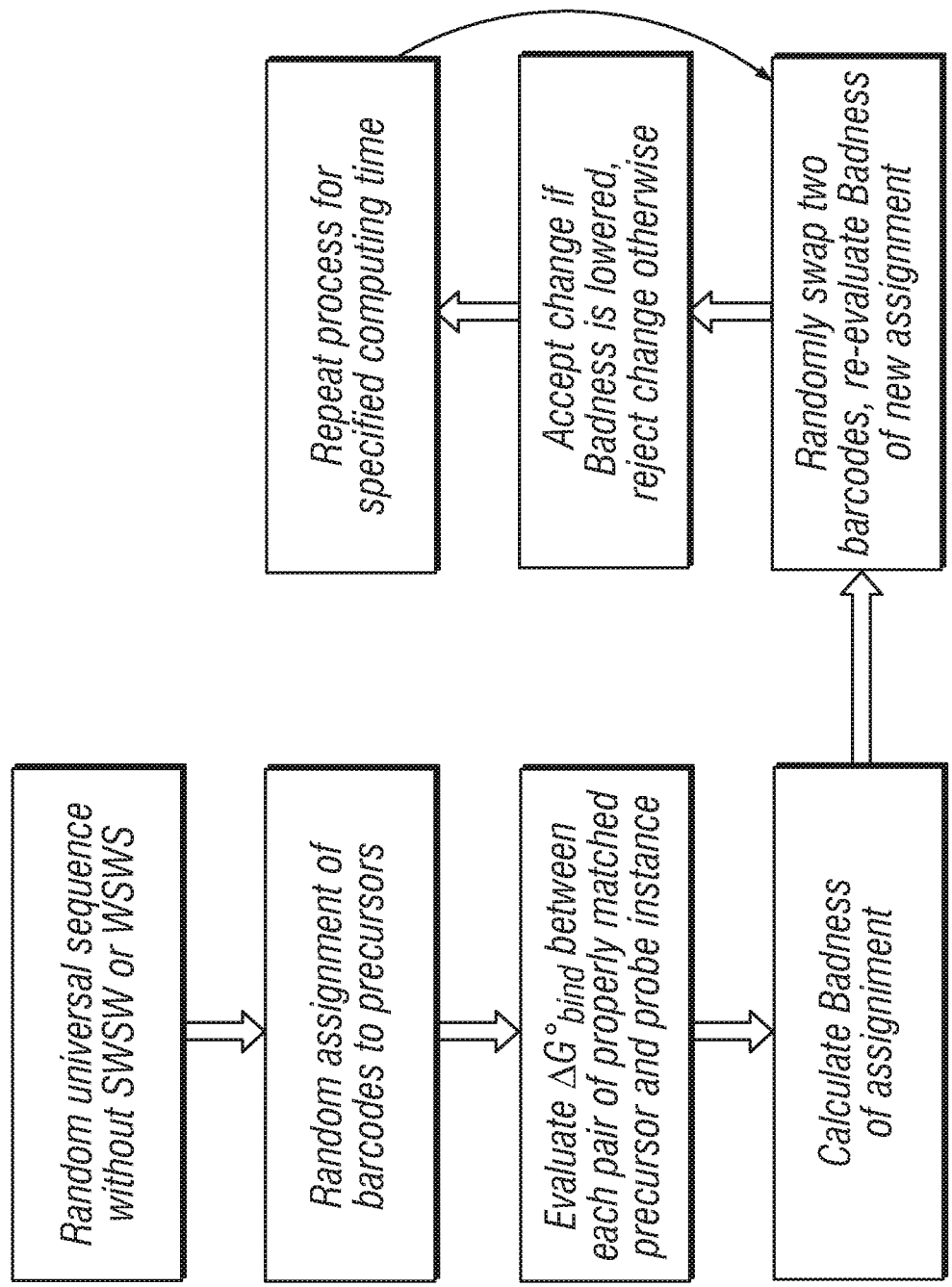
FIGS. 13A-C: Algorithm for the design of probe libraries and assignment of barcodes (region 4).
Figure 13B:
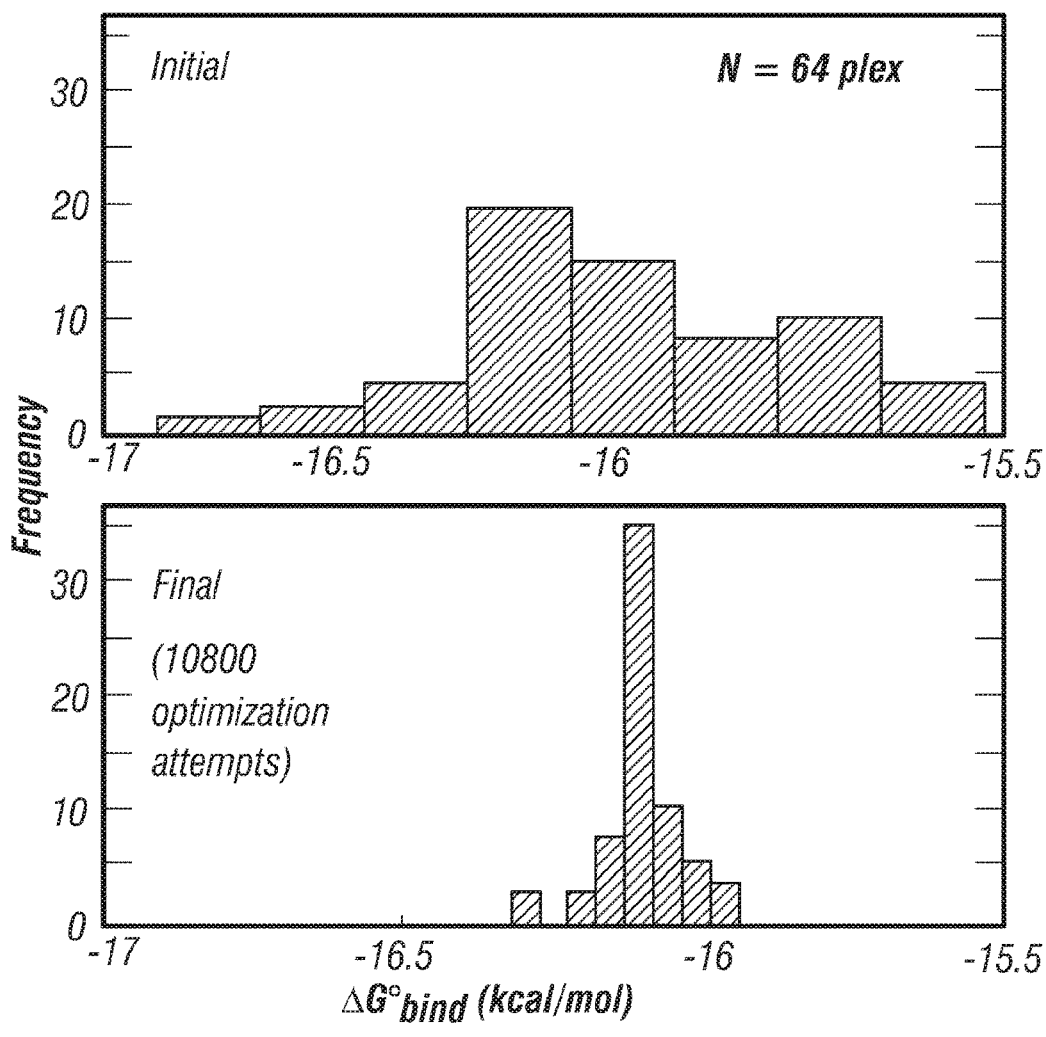
Figure 13C:
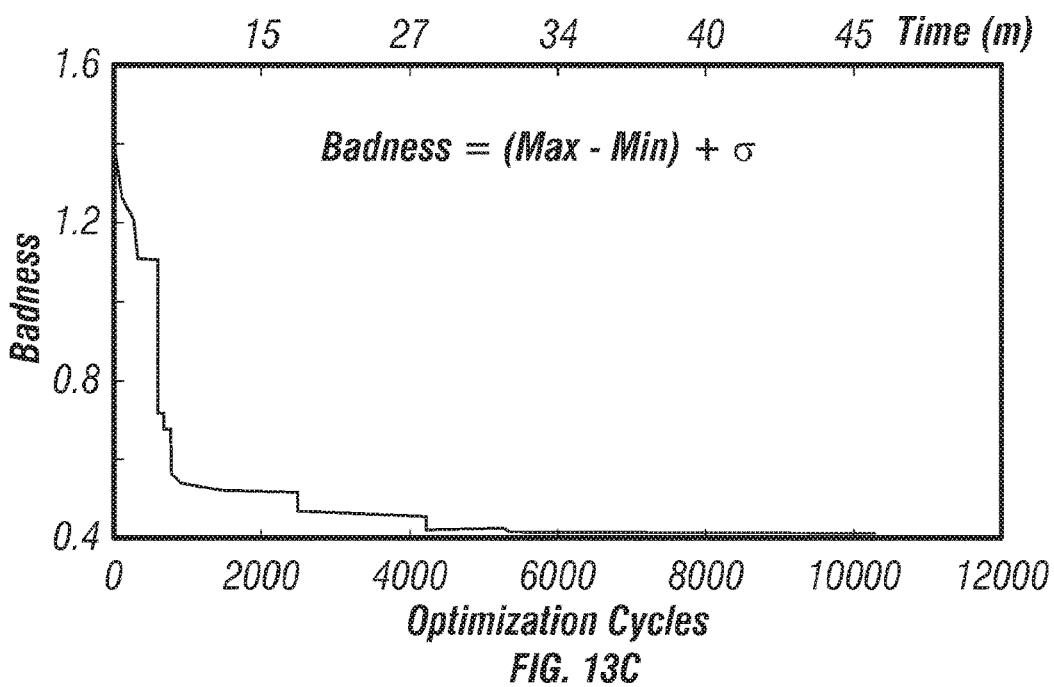
Figure 14:
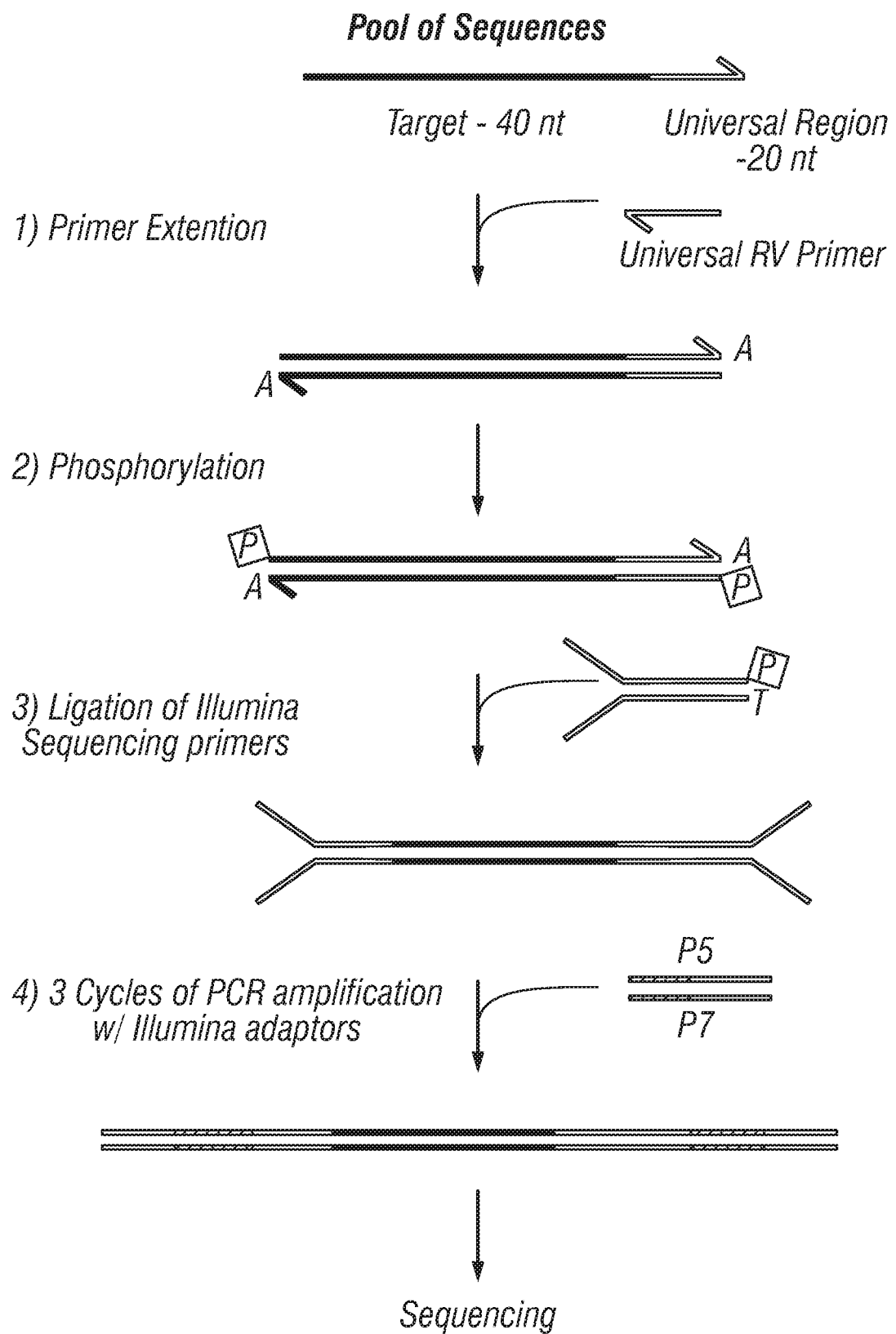
FIG. 14: Workflow for the characterization of purity of oligonucleotides libraries through NGS. The oligonucleotides share a universal region at the 3' end, which is used to align and enzymatically extend one short sequence used as primers. Upon the phosphorylation of the 5' end of the newly formed double stranded library, adaptors containing sequencing primers are enzymatically attached. Finally, the resulting library is amplified for 3 PCR cycles, to introduce the P7 and P5 sequences used for the cluster generation and the consequent sequencing with an Illumina instrument.
Figure 15:
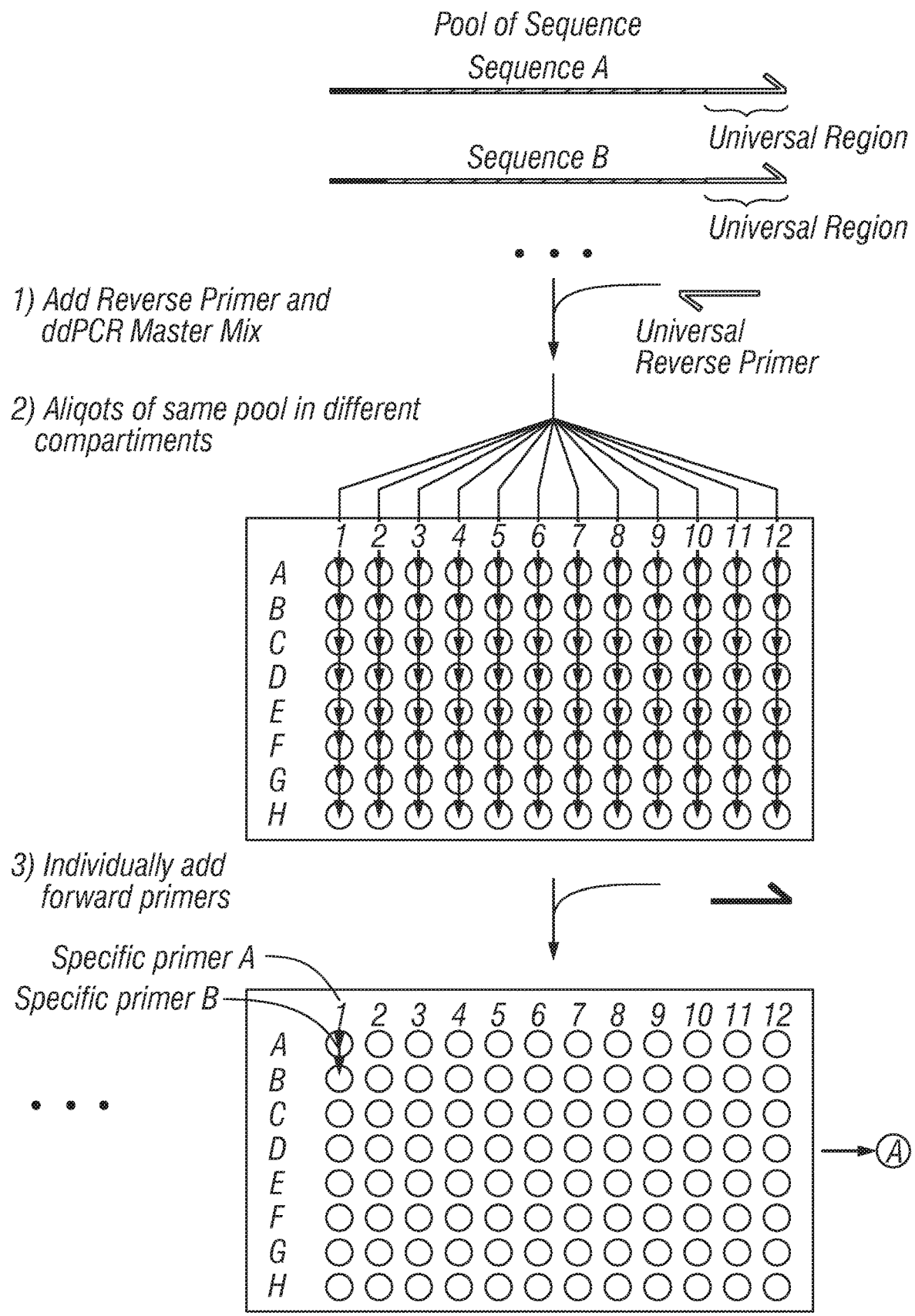
FIG. 15: Workflow for the characterization of stoichiometries within oligonucleotides libraries through digital droplet PCR (ddPCR). The oligonucleotides of the library share a common region at 3' end for the priming with a reverse primer, which is added as well as the master mix contain the enzyme and the EvaGreen dye for ddPCR reaction. The reaction mixture is distributed in 64 equal aliquots, each of which receives one forward primer specific for one oligonucleotide sequence within the library. Subsequently oil is added to every sample, which undergoes to the emulsion process. Finally, upon the PCR reaction, the fluorescent reader is used to determine the ratio between the droplets-containing amplification product and those that are empty, ratio that give a statistical quantification of the template molecule that have been amplified.

FIG. 11 shows data demonstrating purity for a 256-plex, as measured by NGS. Also in this case the fraction of perfect reads for SNAP purified oligo is close the 80%.

Example 2—Purification of Enzymatically-Produced Precursors

Figure 10:
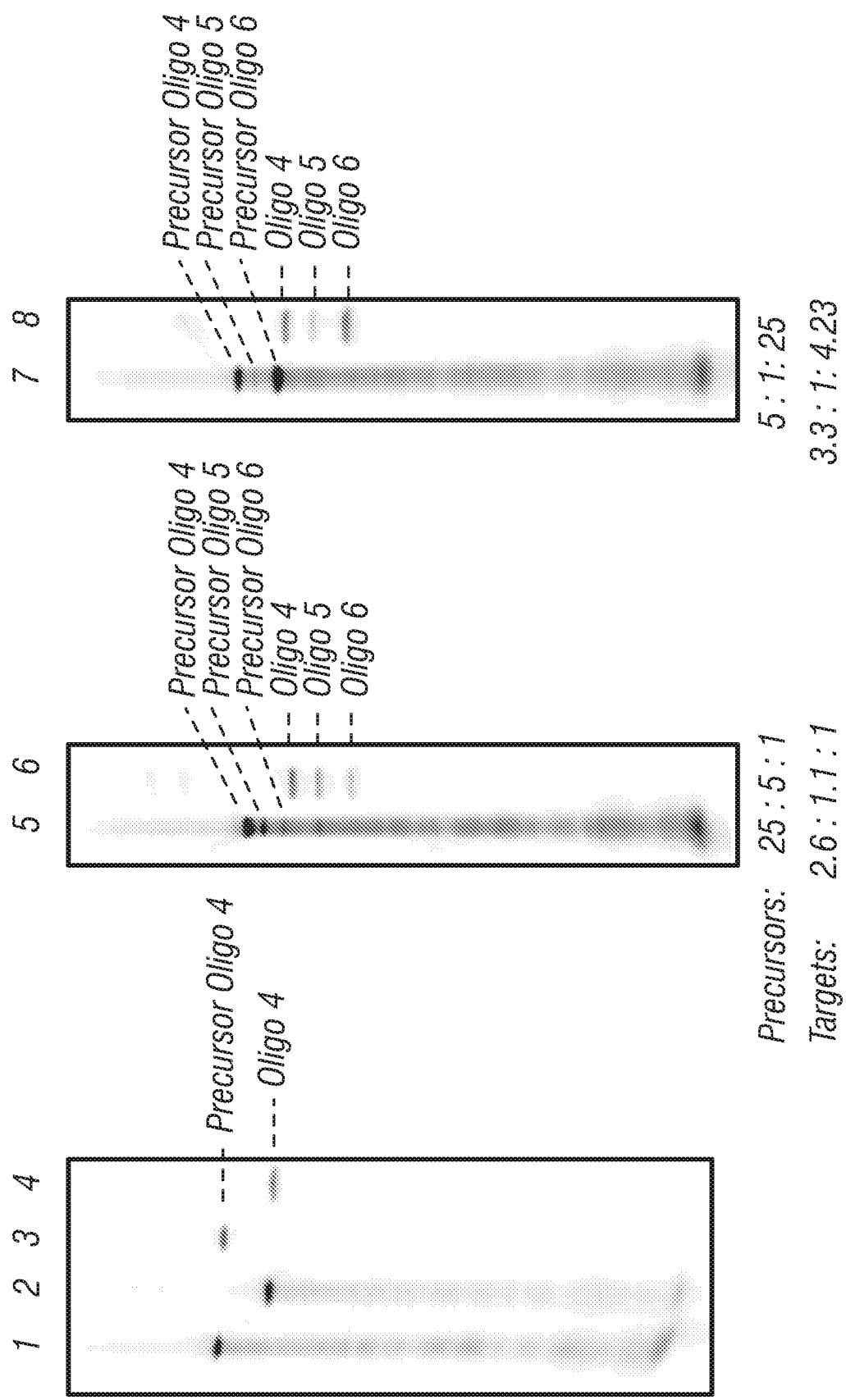
FIG. 10: Experimental results on double-stranded capture probe article shown in FIG. 9B. SNAP was performed using 640 pmol of capture probe biotinylated in 5'end, 1280 pmol of protector strand, and 40 pmol of one unpurified Precursor. Note that, unlike in FIG. 6, only a single Precursor species is introduced, so that the Capture Probes are NOT saturated by Precursors. SNAP protocol is otherwise similar to FIG. 6 caption. Lane 1 corresponds to the unpurified Precursor, Lane 2 corresponds to the PAGE-purified Target oligo, Lane 3 corresponds to the SNAP product without cleavage of regions 3 and 4, and Lane 4 corresponds to the final SNAP product. Lanes 5-10 show that, regardless of initial stoichiometric ratio of the 3 Precursors, the final stoichiometry of the SNAP products are close to 1:1:1.

FIG. 10 shows an example embodiment of purifying enzymatically produced precursors, in this case a transcribed RNA species. Chemical synthesis of RNA oligonucleotides is significantly (8-fold) more expensive than DNA synthesis, and limited to shorter lengths (typically ≤50nt). In vitro transcribed RNA using RNA polymerase and a corresponding DNA template sequence can produce economically produce large quantity of desired RNA target sequences that is also significantly longer than chemically synthesized RNA, but requires labor-intensive Polyacrylamide Gel electrophoresis (PAGE) purification. The present SNAP purification methods can significantly reduce the labor needed to produce RNA molecules, especially in highly multiplexed settings.

Because enzymatically produced precursors disproportionately exhibit truncations and errors at the 3' end rather than the 5' end, the DNA template sequence is designed so that the validation and barcode regions (3 and 4, respectively) will be positioned at the 3' end of the transcript. The stoichiometric capture of full-length precursor RNA transcripts occurs similarly to that of DNA oligonucleotides described previously. An RNAse H enzyme may be used to remove regions 6 and 7 from the precursor to leave only the desired target RNA sequence, because RNAse H will selectively cleave RNA at regions where it is hybridized to DNA.

Example 3—Probe Design Variations

FIGS. 9A-D show a few possible variations in design of the probe and protector sequences. The relative ordering of the regions may be altered, as long as the complementarity relationship between the regions are preserved (e.g., region 2 is complementary to region 3).

Figure 9:
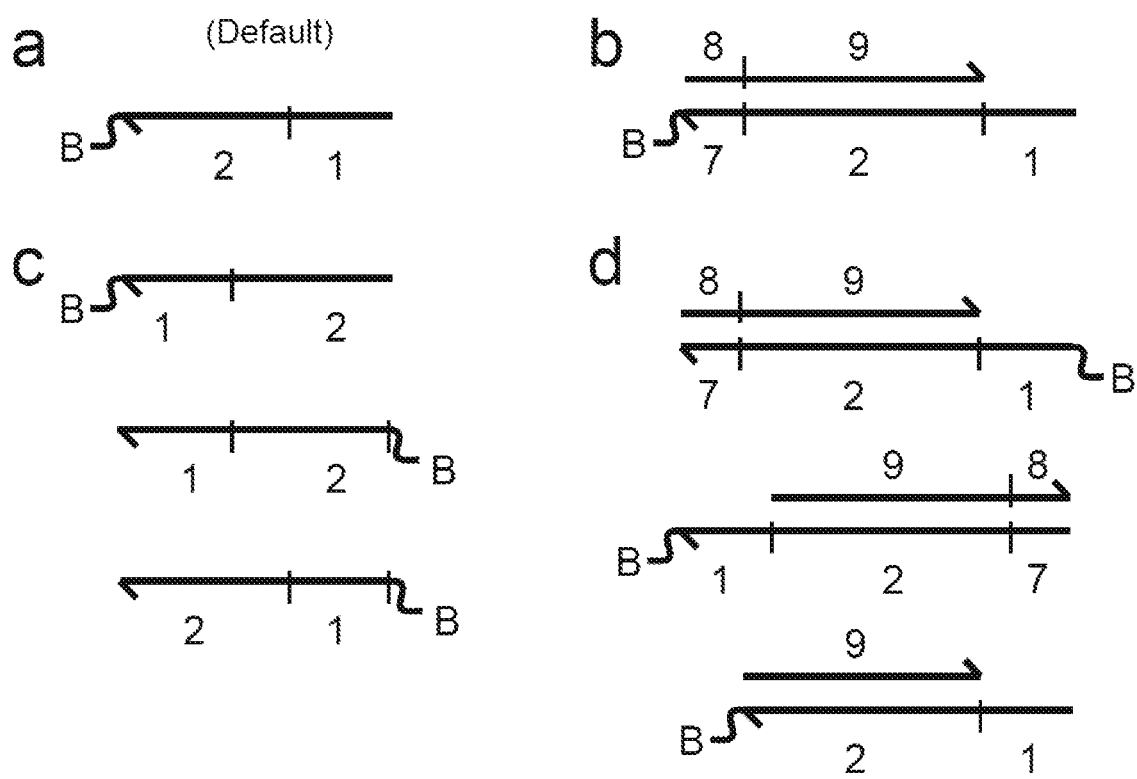
FIGS. 9A-D: Four possible variations in design of the capture probe libraries.

FIG. 9B In those instances when the number capture probes is higher than the number or target sequences, as well as in those case where multiple validation regions (region 2) are used simultaneously, the purpose of the protector oligonucleotide and of regions 7 and 8, is to ensure sequence-specific hybridization of each precursor to its matched probe oligonucleotide. Zhang, D. Y., Chen, S. X., & Yin, P. (2012). Optimizing the specificity of nucleic acid hybridization. Nature chemistry, 4(3), 208-214. and Wu, L. R., Wang, J. S., Fang, J. Z., Evans, E. R., Pinto, A., Pekker, I., & Zhang, D. Y. (2015). Continuously tunable nucleic acid hybridization probes. Nature methods, 12(12), 1191-1196. shows that the competitive hybridization between precursors and the protectors is specific to even single-nucleotide changes in sequence when the sequences of the probe and protector are designed appropriately.

This specificity is useful for 2 purposes: First, it limits the off-target hybridization of precursors to non-cognate probe sequence instances that are not perfectly complementary. Second, it prevents the hybridization of imperfectly synthesized precursors that lack any nucleotide in regions 3 or 4.

Unless explicitly stated otherwise, "complementary" in this document refers to "partially or fully complementary". Two sequences are defined to be "partially complementary" when over 80% of the aligned nucleotides of one sequence is complementary to corresponding nucleotides of the other sequence.

Tables 1-4, below, shows a hypothetical set of sequences for the precursors, capture probe and protector that could be used in methods of the present disclosure. In the sequence of the capture probe, S or W indicates that all variants are included in the capture probe library. For example, both A and T would be present in the mixture of capture probes at each W as part of the randomer library of capture probes.

TABLE 1

List of 64 precursor for the 64plex described in FIGS. 7A-B

| Name | Region 3 | Region 4 | Region 5 |
|---|---|---|---|
| NGSPlex64_1 | TAGGTGC GGTCGCA SEQ ID NO: 1 | TGTGAC TCACTG SEQ ID NO: 2 | GCCCGTCGGCATGTATTAGCTCTAGAATTACCACAGTGCA ACCTTTCGAGTCTCGTACGGTTAAGAGCC SEQ ID NO: 3 |

TABLE 1-continued

List of 64 precursor for the 64plex described in FIGS. 7A-B

| | | | |
|---|---|---|---|
| NGSPlex64_2 | TAGGTGCGGTCGCA SEQ ID NO: 1 | TGTCTGTGTCTG SEQ ID NO: 4 | GGGGCCGGAGAGGGGCTGACCGGGTTGGTTTTGATGCG GTGCTCGAGTCTCGTACGGTTAAGAGCC SEQ ID NO: 5 |
| NGSPlex64_3 | TAGGTGCGGTCGCA SEQ ID NO: 1 | TGTCACACTCTG SEQ ID NO: 6 | CCCTGATTCCCCGTCACCCGTGGTCACCATGGTAGTGGC CATAGCAGTCTCGTACGGTTAAGAGCC SEQ ID NO: 7 |
| NGSPlex64_4 | TAGGTGCGGTCGCA SEQ ID NO: 1 | TGTGACACTCTG SEQ ID NO: 8 | TTTTTCGTCACTACCTCCCCGGGTCGGGAGTGGGTGAATT ATGCTGAACGAGTCTCGTACGGTTAAGAGCC SEQ ID NO: 9 |
| NGSPlex64_5 | TAGGTGCGGTCGCA SEQ ID NO: 1 | TGTGAGAGACTG SEQ ID NO: 10 | GCCCGCCCGCTCCCAAGATCCAACTACGAGCTTTTAGGT CAGTGGAGTCTCGTACGGTTAAGAGCC SEQ ID NO: 11 |
| NGSPlex64_6 | TAGGTGCGGTCGCA SEQ ID NO: 1 | TGTGTCTGTCTG SEQ ID NO: 12 | GGCCGTCCCTCTTAATCATGGCCTCAGTTCCGAAACCTAC ACATTATCTGAGTCTCGTACGGTTAAGAGCC SEQ ID NO: 13 |
| NGSPlex64_7 | TAGGTGCGGTCGCA SEQ ID NO: 1 | TGTGAGTCACTG SEQ ID NO: 14 | GGTATCTGATCGTCTTCGAACCTCCGACTTTCGTTCTGGA CATGCCAGTCTCGTACGGTTAAGAGCC SEQ ID NO: 15 |
| NGSPlex64_8 | TAGGTGCGGTCGCA SEQ ID NO: 1 | TGTCTCAGACTG SEQ ID NO: 16 | TGGTGGTGCCCTTCCGTCAATTCCTTTAAGTTTCATGCTTC TACTCCAGTCTCGTACGGTTAAGAGCC SEQ ID NO: 17 |
| NGSPlex64_9 | TAGGTGCGGTCGCA SEQ ID NO: 1 | TGTCACTCACTG SEQ ID NO: 18 | CCTGTCCGTGTCCGGGCCGGGTGAGGTTTCCCGTGCACT AGGGCTGAGTCTCGTACGGTTAAGAGCC SEQ ID NO: 19 |
| NGSPlex64_10 | TAGGTGCGGTCGCA SEQ ID NO: 1 | TGTGACTGTCTG SEQ ID NO: 20 | GTAACTAGTTAGCATGCCAGAGTCTCGTTCGTTATCGGAT GGCCTAGTATAGTCTCGTACGGTTAAGAGCC SEQ ID NO: 21 |
| NGSPlex64_11 | TAGGTGCGGTCGCA SEQ ID NO: 1 | TGTCACTCTCTG SEQ ID NO: 22 | GCCCCGGACATCTAAGGGCATCACAGACCTGTTATTCCTT GTTGAAGAGTCTCGTACGGTTAAGAGCC SEQ ID NO: 23 |
| NGSPlex64_12 | TAGGTGCGGTCGCA SEQ ID NO: 1 | TGTCTCAGTCTG SEQ ID NO: 24 | GGTAGTAGCGACGGGCGGTGTGTACAAAGGGCAGGTGA GTATTTGATTCAAGTCTCGTACGGTTAAGAGCC SEQ ID NO:25 |
| NGSPlex64_13 | TAGGTGCGGTCGCA SEQ ID NO: 1 | TGTCTCTGACTG SEQ ID NO: 26 | GGCGCTGGGCTCTTCCCTGTTCACTCGCCGTTACTATGTT CGGCCTTTTTAGTCTCGTACGGTTAAGAGCC SEQ ID NO: 27 |
| NGSPlex64_14 | TAGGTGCGGTCGCA SEQ ID NO: 1 | TGTGTGTGACTG SEQ ID NO: 28 | TACCACCCGCTTTGGGCTGCATTCCCAAGCAACCCCCCC GAAAGTCTCGTACGGTTAAGAGCC SEQ ID NO: 29 |
| NGSPlex64_15 | TAGGTGCGGTCGCA SEQ ID NO: 1 | TGTCTGACACTG SEQ ID NO: 30 | CTTTCCCTTACGGTACTTGTTGACTATCGGTCTCGTAAAC GGTTAGATCGAGTCTCGTACGGTTAAGAGCC SEQ ID NO: 31 |

TABLE 1-continued

List of 64 precursor for the 64plex described in FIGS. 7A-B

| NGSPlex64_16 | TAGGTGC GGTCGCA SEQ ID NO: 1 | TGTCTC TCTCTG SEQ ID NO: 32 | GGCGGACTGCGCGGACCCCACCCGTTTACCTCTTAGGTA TATAACGCCAGTCTCGTACGGTTAAGAGCC SEQ ID NO: 33 |
|---|---|---|---|
| NGSPlex64_17 | TAGGTGC GGTCGCA SEQ ID NO: 1 | TGTGAC TCTCTG SEQ ID NO: 34 | GGTGGAAATGCGCCCGGCGGCGGCCGGTCGCCGGTACA CAGTTGAGTCTCGTACGGTTAAGAGCC SEQ ID NO: 35 |
| NGSPlex64_18 | TAGGTGC GGTCGCA SEQ ID NO: 1 | TGTGTG ACTCTG SEQ ID NO: 36 | CCTTCCCCGCCGGGCCTTCCCAGCCGTCCCGGAGCAAGA TTGTTTACAGAAGTCTCGTACGGTTAAGAGCC SEQ ID NO: 37 |
| NGSPlex64_19 | TAGGTGC GGTCGCA SEQ ID NO: 1 | TGTCAG TGTCTG SEQ ID NO: 38 | GGGATTCGGCGAGTGCTGCTGCCGGGGGGGCTGTAGGA CAACGTACAACAGTCTCGTACGGTTAAGAGCC SEQ ID NO: 39 |
| NGSPlex64_20 | TAGGTGC GGTCGCA SEQ ID NO: 1 | TGTGAC TGACTG SEQ ID NO: 40 | GCCGTGGGAGGGGTGGCCCGGCCCCCCCACGAGGACTA CTCAAGAATTGCAGTCTCGTACGGTTAAGAGCC SEQ ID NO: 41 |
| NGSPlex64_21 | TAGGTGC GGTCGCA SEQ ID NO: 1 | TGTGAG ACTCTG SEQ ID NO: 42 | GCCGACCCCGTGCGCTCGCTCCGCCGTCCCCCTCTGCAC GCGGACAGTCTCGTACGGTTAAGAGCC SEQ ID NO: 43 |
| NGSPlex64_22 | TAGGTGC GGTCGCA SEQ ID NO: 1 | TGTGAG TGTCTG SEQ ID NO: 44 | GTGTTAGACTCCTTGGTCCGTGTTTCAAGACGGGTGGTCA TTTAGCGAGTCTCGTACGGTTAAGAGCC SEQ ID NO: 45 |
| NGSPlex64_23 | TAGGTGC GGTCGCA SEQ ID NO: 1 | TGTCTG TCACTG SEQ ID NO: 46 | CCAGGCATAGTTCACCATCTTTCGGGTCCTAACACGGAGC CCATTACAGTCTCGTACGGTTAAGAGCC SEQ ID NO: 47 |
| NGSPlex64_24 | TAGGTGC GGTCGCA SEQ ID NO: 1 | TGTGTG AGTCTG SEQ ID NO: 48 | GGGTGCGTCGGGTCTGCGAGAGCGCCAGCTATCCTATAA GCGCCGTCCAGTCTCGTACGGTTAAGAGCC SEQ ID NO: 49 |
| NGSPlex64_25 | TAGGTGC GGTCGCA SEQ ID NO: 1 | TGTGTC TCACTG SEQ ID NO: 50 | GTTCGGTTCATCCCGCAGCGCCAGTTCTGCTTACCGTGC CACAGTCTCGTACGGTTAAGAGCC SEQ ID NO: 51 |
| NGSPlex64_26 | TAGGTGC GGTCGCA SEQ ID NO: 1 | TGTGTG AGACTG SEQ ID NO: 52 | GGATTCCGACTTCCATGGCCACCGTCCTGCTGTCTGAAAA AATTTCTGCAAGTCTCGTACGGTTAAGAGCC SEQ ID NO: 53 |
| NGSPlex64_27 | TAGGTGC GGTCGCA SEQ ID NO: 1 | TGTCAC AGACTG SEQ ID NO: 54 | ACGCTCCAGCGCCATCCATTTTCAGGGCTAGTTGACGCTA TGGCATCAAGTCTCGTACGGTTAAGAGCC SEQ ID NO: 55 |
| NGSPlex64_28 | TAGGTGC GGTCGCA SEQ ID NO: 1 | TGTGTC TCTCTG SEQ ID NO: 56 | GCAGCGGCCCTCCTACTCGTCGCGGCGTAGCGTCCCATT GAGCAGTTGAGTCTCGTACGGTTAAGAGCC SEQ ID NO: 57 |
| NGSPlex64_29 | TAGGTGC GGTCGCA SEQ ID NO: 1 | TGTCAG ACACTG SEQ ID NO: 58 | ACCCTTCTCCACTTCGGCCTTCAAAGTTCTCGTTTCTAGA GCCCAGTCTCGTACGGTTAAGAGCC SEQ ID NO: 59 |
| NGSPlex64_30 | TAGGTGC GGTCGCA SEQ ID NO: 1 | TGTCAC ACACTG SEQ ID NO: 60 | ACTCTCCCCGGGGCTCCCGCCGGCTTCTCCGGGATGTGA TGGGAGTACCAGTCTCGTACGGTTAAGAGCC SEQ ID NO: 61 |

TABLE 1-continued

List of 64 precursor for the 64plex described in FIGS. 7A-B

| | | | |
|---|---|---|---|
| NGSPlex64_31 | TAGGTGC GGTCGCA SEQ ID NO: 1 | TGTCAC TGTCTG SEQ ID NO: 62 | GCCAGAGGCTGTTCACCTTGGAGACCTGCTGCGGACCGC TCACAAAGTCTCGTACGGTTAAGAGCC SEQ ID NO: 63 |
| NGSPlex64_32 | TAGGTGC GGTCGCA SEQ ID NO: 1 | TGTCTG AGACTG SEQ ID NO: 64 | CCCAGCCCTTAGAGCCAATCCTTATCCCGAAGTTATCAAT CAGTTGCAGTCTCGTACGGTTAAGAGCC SEQ ID NO: 65 |
| NGSPlex64_33 | TAGGTGC GGTCGCA SEQ ID NO: 1 | TGTGTC AGTCTG SEQ ID NO: 66 | GCTCCCCCGGGGAGGGGGAGGACGGGGAGCGGGGTT GAGAGTCTCGTACGGTTAAGAGCC SEQ ID NO: 67 |
| NGSPlex64_34 | TAGGTGC GGTCGCA SEQ ID NO: 1 | TGTGAC AGTCTG SEQ ID NO: 68 | CCCCTGC CGCCCCGACCCTTCTCCCCCCGCCGCCGTATCTAAGGTC CCGTCTCGTACGGTTAAGAGCC SEQ ID NO: 69 |
| NGSPlex64_35 | TAGGTGC GGTCGCA SEQ ID NO: 1 | TGTCTG AGTCTG SEQ ID NO: 70 | GGCGGGGGGGACCGGCCCGCGGCCCCTCCGCCGCCGT CATGTCCAAGTCTCGTACGGTTAAGAGCC SEQ ID NO: 71 |
| NGSPlex64_36 | TAGGTGC GGTCGCA SEQ ID NO: 1 | TGTGAG AGTCTG SEQ ID NO: 72 | GGATTCCCCTGGTCCGCACCAGTTCTAAGTCGGCTAGGG AAGGCAAGTCTCGTACGGTTAAGAGCC SEQ ID NO: 73 |
| NGSPlex64_37 | TAGGTGC GGTCGCA SEQ ID NO: 1 | TGTCAG TCTCTG SEQ ID NO: 74 | GGCTACCTTAAGAGAGTCATAGTTACTCCCGCCGTGGCC CTTCACCAGTCTCGTACGGTTAAGAGCC SEQ ID NO: 75 |
| NGSPlex64_38 | TAGGTGC GGTCGCA SEQ ID NO: 1 | TGTGAG TGACTG SEQ ID NO: 76 | CACCTCTCATGTCTCTTCACCGTGCCAGACTAGAGGCGG ATCCGAGTCTCGTACGGTTAAGAGCC SEQ ID NO: 77 |
| NGSPlex64_39 | TAGGTGC GGTCGCA SEQ ID NO: 1 | TGTCTC ACACTG SEQ ID NO: 78 | GCCCCTCGGGGCTCGCCCCCCCGCCTCACCGGGTCCGG AACGCAGTCTCGTACGGTTAAGAGCC SEQ ID NO: 79 |
| NGSPlex64_40 | TAGGTGC GGTCGCA SEQ ID NO: 1 | TGTGTG ACACTG SEQ ID NO: 80 | GCCCTTCTGCTCCACGGGAGGTTTCTGTCCTCCCTAGTTT GCCAGACCAGTCTCGTACGGTTAAGAGCC SEQ ID NO: 81 |
| NGSPlex64_41 | TAGGTGC GGTCGCA SEQ ID NO: 1 | TGTCTC TGTCTG SEQ ID NO: 82 | GCTTGGCCGCCACAAGCCAGTTATCCCTGTGGTAATGATC TCTCTGAGTAGTCTCGTACGGTTAAGAGCC SEQ ID NO: 83 |
| NGSPlex64_42 | TAGGTGC GGTCGCA SEQ ID NO: 1 | TGTGTG TGTCTG SEQ ID NO: 84 | GCGGTTCCTCTCGTACTGAGCAGGATTACCATGGCGGCC AAATATAGTCTCGTACGGTTAAGAGCC SEQ ID NO: 85 |
| NGSPlex64_43 | TAGGTGC GGTCGCA SEQ ID NO: 1 | TGTCTG TCTCTG SEQ ID NO: 86 | CCGAGGCTCCGCGGCGCTGCCGTATCGTTCCGCCTATGG AGGAGGACAGTCTCGTACGGTTAAGAGCC SEQ ID NO: 87 |
| NGSPlex64_44 | TAGGTGC GGTCGCA SEQ ID NO: 1 | TGTGAC ACACTG SEQ ID NO: 88 | AGGTCGTCTACGAATGGTTTAGCGCCAGGTTCCCCAGCC TCAGGCAGTCTCGTACGGTTAAGAGCC SEQ ID NO: 89 |
| NGSPlex64_45 | TAGGTGC GGTCGCA SEQ ID NO: 1 | TGTCAC TGACTG SEQ ID NO: 90 | CATCTTTCCCTTGCGGTACTATATCTATTGCGCCAGCCTC CCCTCAGTCTCGTACGGTTAAGAGCC SEQ ID NO: 91 |

TABLE 1-continued

List of 64 precursor for the 64plex described in FIGS. 7A-B

| | | | |
|---|---|---|---|
| NGSPlex64_46 | TAGGTGC GGTCGCA SEQ ID NO: 1 | TGTCAG AGTCTG SEQ ID NO: 92 | GACGGGTGTGCTCTTTTAGCTGTTCTTAGGTAGCTAGTAT CTCGTCCCCAGTCTCGTACGGTTAAGAGCC SEQ ID NO: 93 |
| NGSPlex64_47 | TAGGTGC GGTCGCA SEQ ID NO: 1 | TGTGTC ACACTG SEQ ID NO: 94 | GCTTTTAGGCCTACTATGGGTGTTAAATTTTTTACTCTCTC TACAAGTCGAGTCTCGTACGGTTAAGAGCC SEQ ID NO: 95 |
| NGSPlex64_48 | TAGGTGC GGTCGCA SEQ ID NO: 1 | TGTCTG TGACTG SEQ ID NO: 96 | AGGGTGATAGATTGGTCCAATTGGGTGTGAGGAGTTCAA CGTGTATTGTAAGTCTCGTACGGTTAAGAGCC SEQ ID NO: 97 |
| NGSPlex64_49 | TAGGTGC GGTCGCA SEQ ID NO: 1 | TGTGTC ACTCTG SEQ ID NO: 98 | GACTTGTTGGTTGATTGTAGATATTGGGCTGTTAATTGTCA GTTTGTTGTAGTCTCGTACGGTTAAGAGCC SEQ ID NO: 99 |
| NGSPlex64_50 | TAGGTGC GGTCGCA SEQ ID NO: 1 | TGTCTG ACTCTG SEQ ID NO: 100 | GTAAGATTTGCCGAGTTCCTTTTACTTTTTTTAACCTTTCCT TATGCCAAAGTCTCGTACGGTTAAGAGCC SEQ ID NO: 101 |
| NGSPlex64_51 | TAGGTGC GGTCGCA SEQ ID NO: 1 | TGTCAG AGACTG SEQ ID NO: 102 | GCTGAACCCTCGTGGAGCCATTCATACAGGTCCCTGTCC ACCGGCTAGTCTCGTACGGTTAAGAGCC SEQ ID NO: 103 |
| NGSPlex64_52 | TAGGTGC GGTCGCA SEQ ID NO: 1 | TGTCAG TGACTG SEQ ID NO: 104 | GCTCGGAGGTTGGGTTCTGCTCCGAGGTCGCCCCACTTG CATCCTTTGGAGTCTCGTACGGTTAAGAGCC SEQ ID NO: 105 |
| NGSPlex64_53 | TAGGTGC GGTCGCA SEQ ID NO: 1 | TGTGTC AGACTG SEQ ID NO: 106 | GGATTGCGCTGTTATCCCTAGGGTAACTTGTTCCGCAGAC GTTGTGCAGTCTCGTACGGTTAAGAGCC SEQ ID NO: 107 |
| NGSPlex64_54 | TAGGTGC GGTCGCA SEQ ID NO: 1 | TGTCAG ACTCTG SEQ ID NO: 108 | GCCTTATTTCTCTTGTCCTTTCGTACAGGGAGGAATTTGAA TATCTGTTTAGTCTCGTACGGTTAAGAGCC SEQ ID NO: 109 |
| NGSPlex64_55 | TAGGTGC GGTCGCA SEQ ID NO: 1 | TGTCAG TCACTG SEQ ID NO: 110 | TTTCCCGTGGGGTGTGGCTAGGCTAAGCGTTTTGCATTT CATAGACCTTAGTCTCGTACGGTTAAGAGCC SEQ ID NO: 111 |
| NGSPlex64_56 | TAGGTGC GGTCGCA SEQ ID NO: 1 | TGTCTC ACTCTG SEQ ID NO: 112 | CAGGTGAGTTTTAGCTTTATTGGGGAGGGGTGATCTACT GCATCGTTAGAGTCTCGTACGGTTAAGAGCC SEQ ID NO: 113 |
| NGSPlex64_57 | TAGGTGC GGTCGCA SEQ ID NO: 1 | TGTGTC TGACTG SEQ ID NO: 114 | GGCTCGTAGTGTTCTGGCGAGCAGTTTTGTTGATTTGAGT CTAAGGAGTAGTCTCGTACGGTTAAGAGCC SEQ ID NO: 115 |
| NGSPlex64_58 | TAGGTGC GGTCGCA SEQ ID NO: 1 | TGTGTG TCACTG SEQ ID NO: 116 | GTACTTGCGCTTACTTTGTAGCCTTCATCAGGGTTTGGGG TTACCTGCAGTCTCGTACGGTTAAGAGCC SEQ ID NO: 117 |
| NGSPlex64_59 | TAGGTGC GGTCGCA SEQ ID NO: 1 | TGTGAG TCTCTG SEQ ID NO: 118 | GTGACGGGCGGTGTGTACGCGCTTCAGGGCCCTGTACAA TCCTGGTAAGAAGTCTCGTACGGTTAAGAGCC SEQ ID NO: 119 |
| NGSPlex64_60 | TAGGTGC GGTCGCA SEQ ID NO: 1 | TGTCAC AGTCTG SEQ ID NO: 120 | TCTTCATCGACGCACGAGCCGAGTGATCCACCGCTGTTTC CCTTCCAAGTCTCGTACGGTTAAGAGCC SEQ ID NO: 121 |

TABLE 1-continued

List of 64 precursor for the 64plex described in FIGS. 7A-B

| | | | |
|---|---|---|---|
| NGSPlex64_61 | TAGGTGCGGTCGCA SEQ ID NO: 1 | TGTGACAGACTG SEQ ID NO: 122 | GATCAATGTGTCCTGCAATTCACATTAATTCTCGCAGCTAGCGTTCACAAAGTCTCGTACGGTTAAGAGCC SEQ ID NO: 123 |
| NGSPlex64_62 | TAGGTGCGGTCGCA SEQ ID NO: 1 | TGTGTGTCTCTG SEQ ID NO: 124 | GCTCAGACAGGCGTAGCCCCGGGAGGAACCCGGGGTCACGAGTCTCGTACGGTTAAGAGCC SEQ ID NO: 125 |
| NGSPlex64_63 | TAGGTGCGGTCGCA SEQ ID NO: 1 | TGTCTCTCACTG SEQ ID NO: 126 | GCCTACAGCACCCGGTATTCCCAGGCGGTCTCCCAAGGAGCATATATAACAGTCTCGTACGGTTAAGAGCC SEQ ID NO: 127 |
| NGSPlex64_64 | TAGGTGCGGTCGCA SEQ ID NO: 1 | TGTGAGACACTG SEQ ID NO: 128 | GAGATCGGGCGCGTTCAGGGTGGTATGGCCGTAGAGCGTTATCCAGTCTCGTACGGTTAAGAGCC SEQ ID NO: 129 |
| Name | Region 1 | Region 2 | |
| Capture Probe64 plex | CAGWSWSWS | ACATGCGACCGCACCTA TTTTTTTTTT\Biotin (SEQ ID NO: 130) | |

TABLE 2

Figure 8:
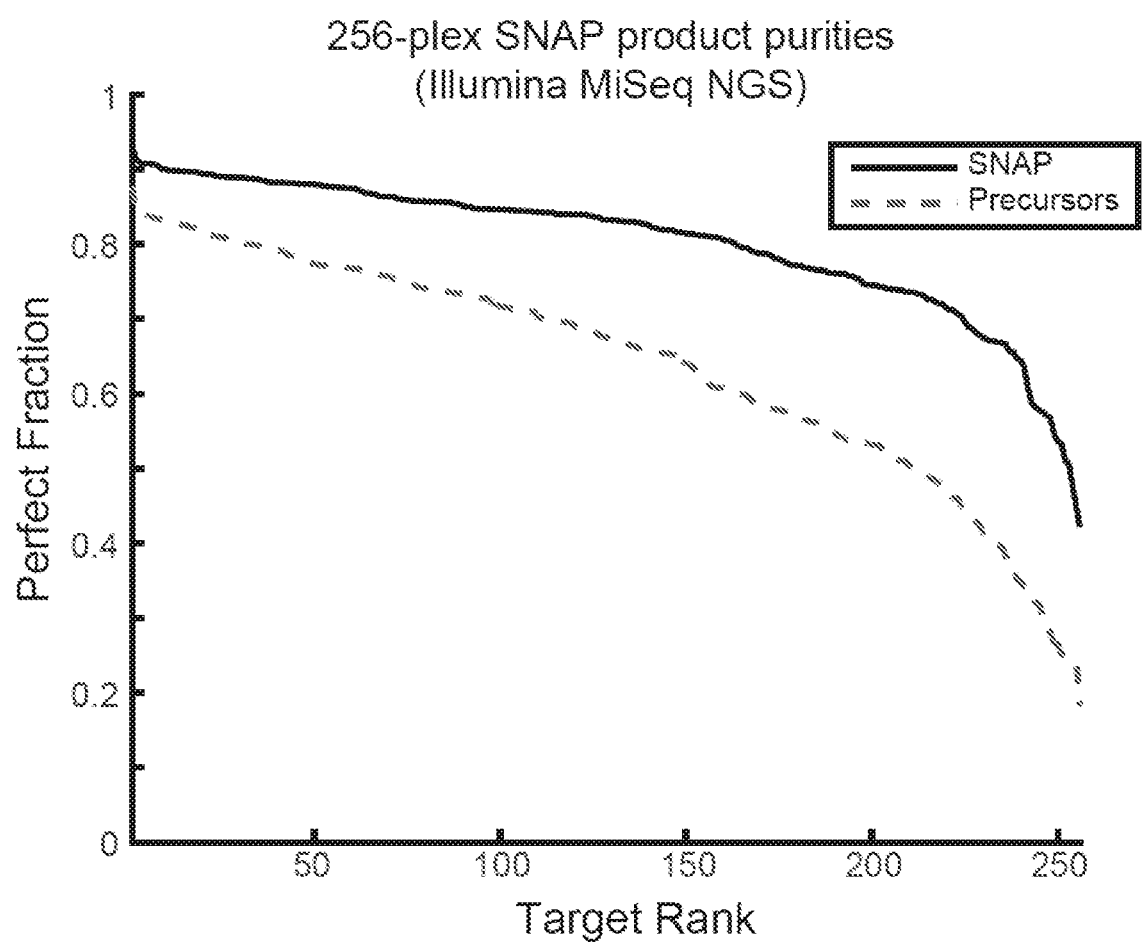
FIG. 8: Characterization of purity for 256-plex SNAP purified (2.5 pmol of each Precursor).

List of 256 precursor for the 256plex of in FIG. 8

| Name | Region 3 | Region 4 | Region 5 |
|---|---|---|---|
| NGSPLEx256_1 | TCGCGAAATTCGGTTGT SEQ ID NO: 131 | CTCAGACAG | TCGCCGCGTAAACGACGCGGCGCGCGTGCTGCCGCACTGGTCGGTGCTCGCAGGCTCGGCA SEQ ID NO: 132 |
| NGSPLEx256_2 | TCGCGAAATTCGGTTGT SEQ ID NO: 131 | GACAGACAG | AGCCCGCCGCGCACGCGCCCTGCGCCCGCGCCGCCCCAGGTGGTCGGTGCTCGCAGGCTCGGCA SEQ ID NO: 133 |
| NGSPLEx256_3 | TCGCGAAATTCGGTTGT SEQ ID NO: 131 | CTGTCTCAG | CTGCTCCCGGCTGGGCCCACCGCCAAAGCAGCGGCCCCACAGGAGCTGGTCGGTGCTCGCAGGCTCGGCA SEQ ID NO: 134 |
| NGSPLEx256_4 | TCGCGAAATTCGGTTGT SEQ ID NO: 131 | GTCACACAG | CTCCTCCGGCCCCGCGCGCCCACTCCGCGCCCGGCCTGGCCGCTGGTCGGTGCTCGCAGGCTCGGCA SEQ ID NO: 135 |
| NGSPLEx256_5 | TCGCGAAATTCGGTTGT SEQ ID NO: 131 | CAGACTCAG | GCCGCCGCCGCCGCCGCCGCCGCCGCCCCGCTGCCTTCTCAGCCTGGTCGGTGCTCGCAGGCTCGGCA SEQ ID NO: 136 |
| NGSPLEx256_6 | TCGCGAAATTCGGTTGT SEQ ID NO: 131 | CAGTGTGAG | GCGGGTGGGCGGCCCGCGTTCCTTAGCCGCGGCTCCGCGGCTGGTCGGTGCTCGCAGGCTCGGCA SEQ ID NO: 137 |
| NGSPLEx256_7 | TCGCGAAATTCGGTTGT SEQ ID NO: 131 | GAGTCTCAG | CCATTCCTGCCAGACCCCCGGCTATCCCGGTGGCCAGGCTGGTCGGTGCTCGCAGGCTCGGCA SEQ ID NO: 138 |
| NGSPLEx256_8 | TCGCGAAATTCGGTTGT SEQ ID NO: 131 | GACTCTCAG | GGCCTCGCGTGCCTGGACAGCCCCGCGGGCCAGCAAGCCTATGGTCGGTGCTCGCAGGCTCGGCA SEQ ID NO: 139 |
| NGSPLEx256_9 | TCGCGAAATTCGGTTGT SEQ ID NO: 131 | CTCTCTCAG | CCATCTCAGGGTGAGGGGCTTCGGCAGCCCCTCATGCTGTGGTCGGTGCTCGCAGGCTCGGCA SEQ ID NO: 140 |
| NGSPLEx256_10 | TCGCGAAATTCGGTTGT SEQ ID NO: 131 | CACACAGTG | GCGACCAAAGGCCGGCGCACGGCCTGGCCGCTCAGCGACTCCCGGCTGGTCGGTGCTCGCAGGCTCGGCA SEQ ID NO: 141 |

TABLE 2-continued

List of 256 precursor for the 256plex of in FIG. 8

| | | | |
|---|---|---|---|
| NGSPLEx 256_11 | TCGCGAAAT TCGGTTGT SEQ ID NO: 131 | GTGTG TCAG | CGCGGCCTCAAAAGGCCTCCTAGGCCGCGGCGGGCAAA GCACTGGTCGGTGCTCGCAGGCTCGGCA SEQ ID NO: 142 |
| NGSPLEx 256_12 | TCGCGAAAT TCGGTTGT SEQ ID NO: 131 | GTGTC AGAG | TACGCTCTCGCGCACCAGGTACGCCTGGTGTTTCTTTGT GGTTGGTCGGTGCTCGCAGGCTCGGCA SEQ ID NO: 143 |
| NGSPLEx 256_13 | TCGCGAAAT TCGGTTGT SEQ ID NO: 131 | GAGAG TGTG | CTCTGCCCAATCCCGGCTCCGGGCGACCCGGGCCCCTG GTCGGTGCTCGCAGGCTCGGCA SEQ ID NO: 144 |
| NGSPLEx 256_14 | TCGCGAAAT TCGGTTGT SEQ ID NO: 131 | CACTC TGAG | TCTTGTAGGAGGCCCATTCCTCCCACCACGGGGCCACC CACCCCGTGGTCGGTGCTCGCAGGCTCGGCA SEQ ID NO: 145 |
| NGSPLEx 256_15 | TCGCGAAAT TCGGTTGT SEQ ID NO: 131 | CTGAC TGTG | CAGCCCCAAACCCGACTGGTCGAAGGGGACATCAAG TCCCCCTGGTCGGTGCTCGCAGGCTCGGCA SEQ ID NO: 146 |
| NGSPLEx 256_16 | TCGCGAAAT TCGGTTGT SEQ ID NO: 131 | GTCTC ACTG | CGCAGCCGACGCCGGCGCGAGAGCAGGGGCGGGGCCG GCGCGGTGGTCGGTGCTCGCAGGCTCGGCA SEQ ID NO: 147 |
| NGSPLEx 256_17 | TCGCGAAAT TCGGTTGT SEQ ID NO: 131 | CAGTC AGAG | GGCCCGCTCGGCAGGCCCCAACTGGCCCTCCCCCTTGG CGGCGATGGTCGGTGCTCGCAGGCTCGGCA SEQ ID NO: 148 |
| NGSPLEx 256_18 | TCGCGAAAT TCGGTTGT SEQ ID NO: 131 | GAGTG TCAG | CGGGCCGAATGCCAGCCCGCCGAGCTCAGGGCAGCGG GGAGCTGGTTGGTCGGTGCTCGCAGGCTCGGCA SEQ ID NO: 149 |
| NGSPLEx 256_19 | TCGCGAAAT TCGGTTGT SEQ ID NO: 131 | CACAG TGAG | ACCTCCGCTGCGTCTCTCGCGCCGCCGCCGCTGCTCG CCGTTGGTCGGTGCTCGCAGGCTCGGCA SEQ ID NO: 150 |
| NGSPLEx 256_20 | TCGCGAAAT TCGGTTGT SEQ ID NO: 131 | CTCAC AGAG | CGGCCCAGGTCTCGGTCAGGGCCAGGGCCGCCGAGAG CAGCAGGATGGTCGGTGCTCGCAGGCTCGGCA SEQ ID NO: 151 |
| NGSPLEx 256_21 | TCGCGAAAT TCGGTTGT SEQ ID NO: 131 | GTGAG AGTG | CTGCCTCACGCATCACAGCACCCCCACCCGAGCGCGGG CGGGTGGTCGGTGCTCGCAGGCTCGGCA SEQ ID NO: 152 |
| NGSPLEx 256_22 | TCGCGAAAT TCGGTTGT SEQ ID NO: 131 | CAGAC ACTG | GGCCACGCTGCCACCAGCAGCAGGCCCATGGGGTGGCA GGGTGGTCGGTGCTCGCAGGCTCGGCA SEQ ID NO: 153 |
| NGSPLEx 256_23 | TCGCGAAAT TCGGTTGT SEQ ID NO: 131 | CTGTG TCAG | CCAGGGGTAGCCCCCTGGATTATGGTCTGACTCAGGACT GGTCGGTGCTCGCAGGCTCGGCA SEQ ID NO: 154 |
| NGSPLEx 256_24 | TCGCGAAAT TCGGTTGT SEQ ID NO: 131 | GTGTC ACTG | CGAAGTTGCCCAGGGTGGCAGTGCAGCCCCGGGCTGAG TGGTCGGTGCTCGCAGGCTCGGCA SEQ ID NO: 155 |
| NGSPLEx 256_25 | TCGCGAAAT TCGGTTGT SEQ ID NO: 131 | GACAC TCTG | GTTACCTCCCCGCACACGGACTGTGTGGATGCGGCGGG GTGGTCGGTGCTCGCAGGCTCGGCA SEQ ID NO: 156 |
| NGSPLEx 256_26 | TCGCGAAAT TCGGTTGT SEQ ID NO: 131 | CAGAG AGAG | AGAGCTCATGTATGGGTTAATCCGACCATGAGCTCTGTG GTCGGTGCTCGCAGGCTCGGCA SEQ ID NO: 157 |
| NGSPLEx 256_27 | TCGCGAAAT TCGGTTGT SEQ ID NO: 131 | CTGAG ACAG | GGCCGGGCCACGGCCAGCATCCGGACCCGGGGCAGCG GCGTGGTCGGTGCTCGCAGGCTCGGCA SEQ ID NO: 158 |
| NGSPLEx 256_28 | TCGCGAAAT TCGGTTGT SEQ ID NO: 131 | GACTC ACAG | GCCATTACGGCTTCCCCGGCCAATAGACGCCCGGCTGC CCTTACATGGTCGGTGCTCGCAGGCTCGGCA SEQ ID NO: 159 |
| NGSPLEx 256_29 | TCGCGAAAT TCGGTTGT SEQ ID NO: 131 | CTCTG ACAG | TTCAGCATTTCTGCTGAAATCTAGGGTGGAAATGCGTTCC TAGTGTGGTCGGTGCTCGCAGGCTCGGCA SEQ ID NO: 160 |

TABLE 2-continued

List of 256 precursor for the 256plex of in FIG. 8

| Name | Part 1 | Part 2 | Part 3 |
|---|---|---|---|
| NGSPLEx 256_30 | TCGCGAAAT TCGGTTGT SEQ ID NO: 131 | CTCAC TCAG | CTCAGCGGAAATCCGGCGATCTGGCCGGAAGTGCGGCA CACTCTGGTCGGTGCTCGCAGGCTCGGCA SEQ ID NO: 161 |
| NGSPLEx 256_31 | TCGCGAAAT TCGGTTGT SEQ ID NO: 131 | GAGAC TCAG | TGGCAGGAAGCTGCAGCCTTTCTCAAGAGCAGCCAGGAT CTCCTGCTGGTCGGTGCTCGCAGGCTCGGCA SEQ ID NO: 162 |
| NGSPLEx 256_32 | TCGCGAAAT TCGGTTGT SEQ ID NO: 131 | GAGTC TCTG | GGTAGCGAGGAGAGCGGCTGAGGCTCAGTGCGCCTGC GCGGCGCTGGTCGGTGCTCGCAGGCTCGGCA SEQ ID NO: 163 |
| NGSPLEx 256_33 | TCGCGAAAT TCGGTTGT SEQ ID NO: 131 | GAGAG TCAG | GCCATGGCAGCTTTCATGGCGTCTGGGGTTTTACCCCAC TCATCTTTGGTCGGTGCTCGCAGGCTCGGCA SEQ ID NO: 164 |
| NGSPLEx 256_34 | TCGCGAAAT TCGGTTGT SEQ ID NO: 131 | CACTC ACAG | TGCATCTTCAGGAGACGCTCGTAGCCCTCGCGCTTCTCC TTGGTCGGTGCTCGCAGGCTCGGCA SEQ ID NO: 165 |
| NGSPLEx 256_35 | TCGCGAAAT TCGGTTGT SEQ ID NO: 131 | CAGAG ACTG | CCGTTGGCCACTTGTGGCCATTCCTACTCCCATGCCGGC TGGTCGGTGCTCGCAGGCTCGGCA SEQ ID NO: 166 |
| NGSPLEx 256_36 | TCGCGAAAT TCGGTTGT SEQ ID NO: 131 | CTCAG TGTG | AACTGGGTCCTACGGCTTGGACTTTCCAACCCTGACAGA CCCGCATGGTCGGTGCTCGCAGGCTCGGCA SEQ ID NO: 167 |
| NGSPLEx 256_37 | TCGCGAAAT TCGGTTGT SEQ ID NO: 131 | GAGAC TGAG | GCCGCTGCTGCAGCAGCTGCCTTATCCACCCGGAGCTT GTGGTCGGTGCTCGCAGGCTCGGCA SEQ ID NO: 168 |
| NGSPLEx 256_38 | TCGCGAAAT TCGGTTGT SEQ ID NO: 131 | GTCTC TGAG | ACGCGGCCTCTCCCGGCCCCTTCCGTTTAGTAGGAGCC GCACTGGTCGGTGCTCGCAGGCTCGGCA SEQ ID NO: 169 |
| NGSPLEx 256_39 | TCGCGAAAT TCGGTTGT SEQ ID NO: 131 | CTCTG AGAG | TGAGGGGCTTGGGCAGACCCTCATGCTGCACATGGCAG GTGTATTGGTCGGTGCTCGCAGGCTCGGCA SEQ ID NO: 170 |
| NGSPLEx 256_40 | TCGCGAAAT TCGGTTGT SEQ ID NO: 131 | GTGTG TGAG | CCCGGCCCAACAAACTACCTACGTCCGGGAGTCGCCAA CCGACGTGGTCGGTGCTCGCAGGCTCGGCA SEQ ID NO: 171 |
| NGSPLEx 256_41 | TCGCGAAAT TCGGTTGT SEQ ID NO: 131 | GAGAC AGAG | AGGCAGACTGCTGCAGGACGGGACTGGGCCGGGAACC GGCTGGTCGGTGCTCGCAGGCTCGGCA SEQ ID NO: 172 |
| NGSPLEx 256_42 | TCGCGAAAT TCGGTTGT SEQ ID NO: 131 | CACTG TGAG | TCTAAACCGTTTATTTCTCCCCACCAGAAGGTTGGGGTG GTCGGTGCTCGCAGGCTCGGCA SEQ ID NO: 173 |
| NGSPLEx 256_43 | TCGCGAAAT TCGGTTGT SEQ ID NO: 131 | GAGTG TGTG | AACACTGCCTTCTTGGCCTTTAAAGCCTTCGCTTTGGCTT CATGGTCGGTGCTCGCAGGCTCGGCA SEQ ID NO: 174 |
| NGSPLEx 256_44 | TCGCGAAAT TCGGTTGT SEQ ID NO: 131 | GTCAC TCTG | CGGTAGCCGAAGGAGTTCAAAAGACCTCTAGTGCGCCCA CCGCATGGTCGGTGCTCGCAGGCTCGGCA SEQ ID NO: 175 |
| NGSPLEx 256_45 | TCGCGAAAT TCGGTTGT SEQ ID NO: 131 | CTCTC TCTG | GGTGACAGGGTGGCCCAGGAGCGGCCACTGAGATGAGA CCTTGGTCGGTGCTCGCAGGCTCGGCA SEQ ID NO: 176 |
| NGSPLEx 256_46 | TCGCGAAAT TCGGTTGT SEQ ID NO: 131 | GAGTG TCTG | GATCACTCCCCAGGCGCTGAGGACGATGCCGCAGGCGG CTGGTCGGTGCTCGCAGGCTCGGCA SEQ ID NO: 177 |
| NGSPLEx 256_47 | TCGCGAAAT TCGGTTGT SEQ ID NO: 131 | GAGAG TGAG | CTTAAGACCAGTCAGTGGTTGCTCCTACCCATTCAGTGG CCTGAGCTGGTCGGTGCTCGCAGGCTCGGCA SEQ ID NO: 178 |
| NGSPLEx 256_48 | TCGCGAAAT TCGGTTGT SEQ ID NO: 131 | GTCTG TCTG | GAAGCTCCTAGAAGCTTCACAAGTTGGGGCACAACTCCT GTTGGTCGGTGCTCGCAGGCTCGGCA SEQ ID NO: 179 |

TABLE 2-continued

List of 256 precursor for the 256plex of in FIG. 8

| | | | |
|---|---|---|---|
| NGSPLEx 256_49 | TCGCGAAAT TCGGTTGT SEQ ID NO: 131 | CACTC AGTG | TGGCGCGCGGCACTGGGAGCCGCCGGGCCGAGCCTGT CAATGGTCGGTGCTCGCAGGCTCGGCA SEQ ID NO: 180 |
| NGSPLEx 256_50 | TCGCGAAAT TCGGTTGT SEQ ID NO: 131 | GAGTC ACAG | TCATAGAAAGAGAGGGAAGTTTTGGCGATCACAACAGCG CCAAATGGTCGGTGCTCGCAGGCTCGGCA SEQ ID NO: 181 |
| NGSPLEx 256_51 | TCGCGAAAT TCGGTTGT SEQ ID NO: 131 | CACTC AGAG | CAAAGAATGCAAACATCATGTTTGAGCCCTGGGGATCAG GGTGGTCGGTGCTCGCAGGCTCGGCA SEQ ID NO: 182 |
| NGSPLEx 256_52 | TCGCGAAAT TCGGTTGT SEQ ID NO: 131 | GTCTG AGTG | GATAGCGCTCCTGTCTATTGGCTGCGCCATCGCCCGTCA GACTGGTCGGTGCTCGCAGGCTCGGCA SEQ ID NO: 183 |
| NGSPLEx 256_53 | TCGCGAAAT TCGGTTGT SEQ ID NO: 131 | CTCAG TGAG | CATATGCAGGTCCCCTGTTGGCCATTCCAATGGGTGGCG GTGGCTGGTCGGTGCTCGCAGGCTCGGCA SEQ ID NO: 184 |
| NGSPLEx 256_54 | TCGCGAAAT TCGGTTGT SEQ ID NO: 131 | CTCAG TCTG | ACTCCCTGCTCCTTGGGAATACGGACCACGCAGTCTATA ATGCCTTGGTCGGTGCTCGCAGGCTCGGCA SEQ ID NO: 185 |
| NGSPLEx 256_55 | TCGCGAAAT TCGGTTGT SEQ ID NO: 131 | CACAC TGTG | CGGGGTAACCGTGGAGGGCGACGCGCAGAGGCTGCGG CTATTTATGGTCGGTGCTCGCAGGCTCGGCA SEQ ID NO: 186 |
| NGSPLEx 256_56 | TCGCGAAAT TCGGTTGT SEQ ID NO: 131 | CAGTC TGTG | GGACTGGTCCCATGAGGCAGAAGGAGCACCAGCGCCTG CTGGGTGGTGGTCGGTGCTCGCAGGCTCGGCA SEQ ID NO: 187 |
| NGSPLEx 256_57 | TCGCGAAAT TCGGTTGT SEQ ID NO: 131 | GTCTC TGTG | CGAGAAACAGCGCCCGACACCTGGCCCTTCGCAGCTCT CGCCTTGGTCGGTGCTCGCAGGCTCGGCA SEQ ID NO: 188 |
| NGSPLEx 256_58 | TCGCGAAAT TCGGTTGT SEQ ID NO: 131 | CAGAG TGTG | CTGCATGGCCTTCATGACATGAAGGTTGGGCACATTCTT GTCTGGTCGGTGCTCGCAGGCTCGGCA SEQ ID NO: 189 |
| NGSPLEx 256_59 | TCGCGAAAT TCGGTTGT SEQ ID NO: 131 | CTGAC TGAG | CCGAAACCCATGGTGTCGGCTGTATCCGAGAGCTGGGG AGCAGCTGGTCGGTGCTCGCAGGCTCGGCA SEQ ID NO: 190 |
| NGSPLEx 256_60 | TCGCGAAAT TCGGTTGT SEQ ID NO: 131 | GACAC TCAG | TTCATGCAGATCACCTGCACCCCGCTTGTGTTCAGTGGG GTTGGTCGGTGCTCGCAGGCTCGGCA SEQ ID NO: 191 |
| NGSPLEx 256_61 | TCGCGAAAT TCGGTTGT SEQ ID NO: 131 | GAGAC ACAG | AGCTGCCGGGGTCCGGTTCCTCAGCTCCAGGTGGATCC TTGGTCGGTGCTCGCAGGCTCGGCA SEQ ID NO: 192 |
| NGSPLEx 256_62 | TCGCGAAAT TCGGTTGT SEQ ID NO: 131 | CTCTG TGAG | CTCGGAAGTAGCCCCCGTAGGTGCCCTGCTTGTGGTCAA ACTGGTCGGTGCTCGCAGGCTCGGCA SEQ ID NO: 193 |
| NGSPLEx 256_63 | TCGCGAAAT TCGGTTGT SEQ ID NO: 131 | CACAC AGAG | CGGGGGTAGCGGTCAATTCCAGCCACCAGAGCATGGCT GTGGTCGGTGCTCGCAGGCTCGGCA SEQ ID NO: 194 |
| NGSPLEx 256_64 | TCGCGAAAT TCGGTTGT SEQ ID NO: 131 | GTCAC ACTG | GAAACATGATCGCTTATAAGCCAGCGGTCCCAATTCGGT CCACCGTGGTCGGTGCTCGCAGGCTCGGCA SEQ ID NO: 195 |
| NGSPLEx 256_65 | TCGCGAAAT TCGGTTGT SEQ ID NO: 131 | GTGTG ACAG | CCCACACGTCCATGACTGGTCGTCCTAGATTTTAGGTGT CTGGTCGGTGCTCGCAGGCTCGGCA SEQ ID NO: 196 |
| NGSPLEx 256_66 | TCGCGAAAT TCGGTTGT SEQ ID NO: 131 | CACAC ACAG | CTTTAGCTCGAGATTGTCCCTCTCTGTCCAGCAGATAGG TGGTCGGTGCTCGCAGGCTCGGCA SEQ ID NO: 197 |
| NGSPLEx 256_67 | TCGCGAAAT TCGGTTGT SEQ ID NO: 131 | CTCTC AGAG | GCCGTCCTGCGCAAGCGCTTTTCAACCCCACTCCTTTCT TGGTCGGTGCTCGCAGGCTCGGCA SEQ ID NO: 198 |

TABLE 2-continued

List of 256 precursor for the 256plex of in FIG. 8

| | | | |
|---|---|---|---|
| NGSPLEx 256_68 | TCGCGAAAT TCGGTTGT SEQ ID NO: 131 | GACTG TGTG | CAGTCTCTGGGAGAATGGGCAGTTCCCAATCTTGGCCCC TGGTCGGTGCTCGCAGGCTCGGCA SEQ ID NO: 199 |
| NGSPLEx 256_69 | TCGCGAAAT TCGGTTGT SEQ ID NO: 131 | GTCTG TGTG | GGTTGGTGCTTGCCACACTTCTTACAGAAAGTCCGGCGG GTTTTGGTCGGTGCTCGCAGGCTCGGCA SEQ ID NO: 200 |
| NGSPLEx 256_70 | TCGCGAAAT TCGGTTGT SEQ ID NO: 131 | GTGTC ACAG | CATGTAGTTGAGGTCAATGAAGGGGTCATTGATGGCAAC AATATTGGTCGGTGCTCGCAGGCTCGGCA SEQ ID NO: 201 |
| NGSPLEx 256_71 | TCGCGAAAT TCGGTTGT SEQ ID NO: 131 | CTCAC TGTG | CGGAACTGGAGGTTTCCTTTTCCGCCATAGTTTGTCCTG GTCGGTGCTCGCAGGCTCGGCA SEQ ID NO: 202 |
| NGSPLEx 256_72 | TCGCGAAAT TCGGTTGT SEQ ID NO: 131 | GTGTC TCAG | TTGTAGTCTGAGAGAGTGCGGCCATCCTCCAGCTGTTTG CCGGTGGTCGGTGCTCGCAGGCTCGGCA SEQ ID NO: 203 |
| NGSPLEx 256_73 | TCGCGAAAT TCGGTTGT SEQ ID NO: 131 | GTCAG TGTG | CTGCAGTGGCTTTAAACCCACAGTAGTAACCTGCAGGAT CACACTTGGTCGGTGCTCGCAGGCTCGGCA SEQ ID NO: 204 |
| NGSPLEx 256_74 | TCGCGAAAT TCGGTTGT SEQ ID NO: 131 | CACTG TCTG | CGAAGGACAGGTGGTCTCTTCGTTGGGACGTCCCCTTTG CCAGCATGGTCGGTGCTCGCAGGCTCGGCA SEQ ID NO: 205 |
| NGSPLEx 256_75 | TCGCGAAAT TCGGTTGT SEQ ID NO: 131 | CAGTG AGAG | AGCTTGGCTCCCTTCTTGCGGCCCAGGGGCAGCGCATG GTCGGTGCTCGCAGGCTCGGCA SEQ ID NO: 206 |
| NGSPLEx 256_76 | TCGCGAAAT TCGGTTGT SEQ ID NO: 131 | GTCTG TGAG | TTCCGACATGTCCGCATTTTTGATCACGGCCTTTCGGTG GTCGGTGCTCGCAGGCTCGGCA SEQ ID NO: 207 |
| NGSPLEx 256_77 | TCGCGAAAT TCGGTTGT SEQ ID NO: 131 | CAGAG TCAG | CTTGGGAAGACCAAGTCCTCAAGGATGGCATCGTGCACA GCTGTGGTCGGTGCTCGCAGGCTCGGCA SEQ ID NO: 208 |
| NGSPLEx 256_78 | TCGCGAAAT TCGGTTGT SEQ ID NO: 131 | CTCTG TCAG | CGGCCGCCTCCAGGAACGCCGACCACTCCACTTTAGGT ATCATGGTCGGTGCTCGCAGGCTCGGCA SEQ ID NO: 209 |
| NGSPLEx 256_79 | TCGCGAAAT TCGGTTGT SEQ ID NO: 131 | GTCTC TCTG | AGGCGAAGTTCCGTCTACGGCTATTTAATGGAGCGCCTG GTCGGTGCTCGCAGGCTCGGCA SEQ ID NO: 210 |
| NGSPLEx 256_80 | TCGCGAAAT TCGGTTGT SEQ ID NO: 131 | CTCTC TGAG | TGTATGTTCCATCCATGTGAGCAGCAAATGTGTATTTCCC ACTGGTCGGTGCTCGCAGGCTCGGCA SEQ ID NO: 211 |
| NGSPLEx 256_81 | TCGCGAAAT TCGGTTGT SEQ ID NO: 131 | CAGTC TGAG | GGTCTCATCCGAACCCTGCGGATATATTTTTCACCCAAGA AATTTGGTCGGTGCTCGCAGGCTCGGCA SEQ ID NO: 212 |
| NGSPLEx 256_82 | TCGCGAAAT TCGGTTGT SEQ ID NO: 131 | GACAC AGAG | GGCCTTCACGCGGCCCAGGAGTTTCTTATTGTTGCGGCA GTTGGTCGGTGCTCGCAGGCTCGGCA SEQ ID NO: 213 |
| NGSPLEx 256_83 | TCGCGAAAT TCGGTTGT SEQ ID NO: 131 | GTGAG ACAG | CCTTTTCCAAGGATTTTACGTTGCGGCTTGTTAGGGTGAT TTGGTCGGTGCTCGCAGGCTCGGCA SEQ ID NO: 214 |
| NGSPLEx 256_84 | TCGCGAAAT TCGGTTGT SEQ ID NO: 131 | GTGTG AGAG | ACTGTTCTCTCTTGGCAAAGTAATCAGGATACATTGCCTG GTCGGTGCTCGCAGGCTCGGCA SEQ ID NO: 215 |
| NGSPLEx 256_85 | TCGCGAAAT TCGGTTGT SEQ ID NO: 131 | GTCAC TGTG | ACAGTAGCATGCAGTCCCACAACTTGTACCAGCATCCCC AGCGTCTTGGTCGGTGCTCGCAGGCTCGGCA SEQ ID NO: 216 |
| NGSPLEx 256_86 | TCGCGAAAT TCGGTTGT SEQ ID NO: 131 | GTCAG TCAG | ACTTGGCTCCAGCATGTTGTCACCATTCCAACCAGAAATT GGCATGGTCGGTGCTCGCAGGCTCGGCA SEQ ID NO: 217 |

TABLE 2-continued

List of 256 precursor for the 256plex of in FIG. 8

| NGSPLEx 256_87 | TCGCGAAAT TCGGTTGT SEQ ID NO: 131 | GACTC AGAG | ACAATGCAAAGATGGCTTTTCAGAGCAGCCAGTGGGGGT GGTCGGTGCTCGCAGGCTCGGCA SEQ ID NO: 218 |
|---|---|---|---|
| NGSPLEx 256_88 | TCGCGAAAT TCGGTTGT SEQ ID NO: 131 | CTGAG ACTG | CGACGTAGCCCGGCCTCTTCGACCTGCACCTCCGCGGC TCCCTCTGTGGTCGGTGCTCGCAGGCTCGGCA SEQ ID NO: 219 |
| NGSPLEx 256_89 | TCGCGAAAT TCGGTTGT SEQ ID NO: 131 | CTCTC ACTG | AGTGGAAACAGGATTACTATGATACAAAACTTCCACTACT GGTCGGTGCTCGCAGGCTCGGCA SEQ ID NO: 220 |
| NGSPLEx 256_90 | TCGCGAAAT TCGGTTGT SEQ ID NO: 131 | GTGAC ACAG | GCAAAGGCAATCTTCAAATAGAAGCTGGCAACACAAGAC CTGGTCGGTGCTCGCAGGCTCGGCA SEQ ID NO: 221 |
| NGSPLEx 256_91 | TCGCGAAAT TCGGTTGT SEQ ID NO: 131 | GTGTG TGTG | AATCACGCACTGTCCCCAACAGCCCCAGTTAACACAGGG TGGTCGGTGCTCGCAGGCTCGGCA SEQ ID NO: 222 |
| NGSPLEx 256_92 | TCGCGAAAT TCGGTTGT SEQ ID NO: 131 | CTCAG ACTG | CAGGGTTTCTGGTCCAAATAGGCTTGGTCTTGTTTATGGT CGGTGCTCGCAGGCTCGGCA SEQ ID NO: 223 |
| NGSPLEx 256_93 | TCGCGAAAT TCGGTTGT SEQ ID NO: 131 | GTGTC TCTG | CCCGAATCCGCCGGCCCTTCTCACCAAGAACATTCTGTT GGTCGGTGCTCGCAGGCTCGGCA SEQ ID NO: 224 |
| NGSPLEx 256_94 | TCGCGAAAT TCGGTTGT SEQ ID NO: 131 | GTCTC TCAG | GGAGATCCATCATCTCTCCCTTCAATTTGTCTTCGATGAC ATTGGTCGGTGCTCGCAGGCTCGGCA SEQ ID NO: 225 |
| NGSPLEx 256_95 | TCGCGAAAT TCGGTTGT SEQ ID NO: 131 | GACTC ACTG | TGGCATTAGCAGTAGGTTCTTGTATTTGAGTCTGCTTGGT CGGTGCTCGCAGGCTCGGCA SEQ ID NO: 226 |
| NGSPLEx 256_96 | TCGCGAAAT TCGGTTGT SEQ ID NO: 131 | CTCAC AGTG | GAAAACTGGTCAGATGAATATTATTGCTTCCCATTTTCAA CCAGTTGGTCGGTGCTCGCAGGCTCGGCA SEQ ID NO: 227 |
| NGSPLEx 256_97 | TCGCGAAAT TCGGTTGT SEQ ID NO: 131 | GACTC TGTG | TCCAGAGGGTCCGGATCGCTCTCTTCTGCACTGAGGTTG GTCGGTGCTCGCAGGCTCGGCA SEQ ID NO: 228 |
| NGSPLEx 256_98 | TCGCGAAAT TCGGTTGT SEQ ID NO: 131 | CTCTG ACTG | CCATCCTGGCAGGCGGCTGTGGTGGTTTGAAGAGTTTG GACTGGTCGGTGCTCGCAGGCTCGGCA SEQ ID NO: 229 |
| NGSPLEx 256_99 | TCGCGAAAT TCGGTTGT SEQ ID NO: 131 | GTCAG TGAG | GCTGGCAAGGCTGAGCAATTCATGTTTATCTGCAACAGC TGGTCGGTGCTCGCAGGCTCGGCA SEQ ID NO: 230 |
| NGSPLEx 256_100 | TCGCGAAAT TCGGTTGT SEQ ID NO: 131 | GAGAG ACTG | AGCATCAGCTACTGCCAGCGGTTCATGGGCTTCTTTTAC TATGGTCGGTGCTCGCAGGCTCGGCA SEQ ID NO: 231 |
| NGSPLEx 256_101 | TCGCGAAAT TCGGTTGT SEQ ID NO: 131 | CAGTC TCTG | TGAGTGAGCCCTCCTGCCACGTCTCCACGGTCACCACCT CCTCTGGTCGGTGCTCGCAGGCTCGGCA SEQ ID NO: 232 |
| NGSPLEx 256_102 | TCGCGAAAT TCGGTTGT SEQ ID NO: 131 | GTGAC AGAG | CTTTGGGTCCCAAGGTGCTCTTTACCAAGTCTCCAATGG CGATTGGTCGGTGCTCGCAGGCTCGGCA SEQ ID NO: 233 |
| NGSPLEx 256_103 | TCGCGAAAT TCGGTTGT SEQ ID NO: 131 | CAGTG ACTG | AACCCAATTAGTTCCCAGAAGTCACAACTCAGCTCATGG CCACCTGTGGTCGGTGCTCGCAGGCTCGGCA SEQ ID NO: 234 |
| NGSPLEx 256_104 | TCGCGAAAT TCGGTTGT SEQ ID NO: 131 | CACAC TGAG | CTCCTTGGTTCCATCTCCCGTGGCATCGCTTCCCTCTCG GTGGTCGGTGCTCGCAGGCTCGGCA SEQ ID NO: 235 |
| NGSPLEx 256_105 | TCGCGAAAT TCGGTTGT SEQ ID NO: 131 | GAGTG AGAG | TATTTCACCAGGCCGGCAAAGAATGGACGGTCCTTCAGG TCAACGTGGTCGGTGCTCGCAGGCTCGGCA SEQ ID NO: 236 |

TABLE 2-continued

List of 256 precursor for the 256plex of in FIG. 8

| NGSPLEx 256_106 | TCGCGAAAT TCGGTTGT SEQ ID NO: 131 | CTGTG TCTG | CCCTCAGAGGACAGGGCGCGGTTGCTGGGTCATGAGCA CCTGGTCGGTGCTCGCAGGCTCGGCA SEQ ID NO: 237 |
|---|---|---|---|
| NGSPLEx 256_107 | TCGCGAAAT TCGGTTGT SEQ ID NO: 131 | CTGTC TGTG | CAGGCACCAGACCAAAGACCTCCTGCCCCACAGCAAATG GTCGGTGCTCGCAGGCTCGGCA SEQ ID NO: 238 |
| NGSPLEx 256_108 | TCGCGAAAT TCGGTTGT SEQ ID NO: 131 | CAGTG AGTG | AGTTTCCTCTTCACTCAGCAGCATGTTGGGGATCCCGCG GTGGTCGGTGCTCGCAGGCTCGGCA SEQ ID NO: 239 |
| NGSPLEx 256_109 | TCGCGAAAT TCGGTTGT SEQ ID NO: 131 | GTCAC TGAG | TCTGTGAGAAAACCTTGGAGAATCAATAATGGTGGATTCA TTGATTGGTCGGTGCTCGCAGGCTCGGCA SEQ ID NO: 240 |
| NGSPLEx 256_110 | TCGCGAAAT TCGGTTGT SEQ ID NO: 131 | GAGAC ACTG | GCTGTATCTGGTCCTGGCGGCCGGCTGTGATGTTTGACA TTGTCCATGGTCGGTGCTCGCAGGCTCGGCA SEQ ID NO: 241 |
| NGSPLEx 256_111 | TCGCGAAAT TCGGTTGT SEQ ID NO: 131 | CACTC TCTG | GATGGCGGCGGGGGGCAGGGGGCGCACGTAGCCTGGC CATGGTCGGTGCTCGCAGGCTCGGCA SEQ ID NO: 242 |
| NGSPLEx 256_112 | TCGCGAAAT TCGGTTGT SEQ ID NO: 131 | GACTG TGAG | CTCTCTCTTCAGCAATGGTGAGGCGGATACCCTTTCCTC GGGTGGTCGGTGCTCGCAGGCTCGGCA SEQ ID NO: 243 |
| NGSPLEx 256_113 | TCGCGAAAT TCGGTTGT SEQ ID NO: 131 | GTGTG ACTG | TCTGGGACAAGACAGTCGAGGGAGCTTCTTCCTCAGGGA ACTTGGTCGGTGCTCGCAGGCTCGGCA SEQ ID NO: 244 |
| NGSPLEx 256_114 | TCGCGAAAT TCGGTTGT SEQ ID NO: 131 | CAGAG AGTG | GCTGCCAAAGCTGGGTCCATGACAACTTCTGGTGGGGC GTGGTCGGTGCTCGCAGGCTCGGCA SEQ ID NO: 245 |
| NGSPLEx 256_115 | TCGCGAAAT TCGGTTGT SEQ ID NO: 131 | GTCAG TCTG | AGACTGCCAGCGAAGCCCCTCTTATGAGCAAAAGAGCAA CCCTGGTCGGTGCTCGCAGGCTCGGCA SEQ ID NO: 246 |
| NGSPLEx 256_116 | TCGCGAAAT TCGGTTGT SEQ ID NO: 131 | CACTC TCAG | CTTCAGGTGTCCTTGAAGCAATAATTTCTGTCAGTACTTT TTCATTTGGTCGGTGCTCGCAGGCTCGGCA SEQ ID NO: 247 |
| NGSPLEx 256_117 | TCGCGAAAT TCGGTTGT SEQ ID NO: 131 | CTGTC ACAG | AACGATCAAAATTAGACATGTCTTCATCTGAATCATCTTC CCAGTGGTCGGTGCTCGCAGGCTCGGCA SEQ ID NO: 248 |
| NGSPLEx 256_118 | TCGCGAAAT TCGGTTGT SEQ ID NO: 131 | GTGAG TGTG | CGGCCACACCATCTTTGTCAGCAGTCACATTGCCCAAGT CTCCAACTGGTCGGTGCTCGCAGGCTCGGCA SEQ ID NO: 249 |
| NGSPLEx 256_119 | TCGCGAAAT TCGGTTGT SEQ ID NO: 131 | GAGTC AGTG | TGACCTCTCACTTTTCCAGCACGGGCCAGGGAACCATGG ACTTTTGGTCGGTGCTCGCAGGCTCGGCA SEQ ID NO: 250 |
| NGSPLEx 256_120 | TCGCGAAAT TCGGTTGT SEQ ID NO: 131 | GTGAC TGAG | GTCAGCATAATCTTTATTTCAAAATAACATTTTTATTATGG TCGGTGCTCGCAGGCTCGGCA SEQ ID NO: 252 |
| NGSPLEx 256_121 | TCGCGAAAT TCGGTTGT SEQ ID NO: 131 | CTCAC ACAG | AGCCACAGGATGTTCTCGTCACACTTTTCCATGTAGGCG TTATTGGTCGGTGCTCGCAGGCTCGGCA SEQ ID NO: 253 |
| NGSPLEx 256_122 | TCGCGAAAT TCGGTTGT SEQ ID NO: 131 | GTCTG ACAG | TATCCGTTCCTTACATTGAACCATTTTACTGTTCCCAAAAC CTTCGTGGTCGGTGCTCGCAGGCTCGGCA SEQ ID NO: 254 |
| NGSPLEx 256_123 | TCGCGAAAT TCGGTTGT SEQ ID NO: 131 | CTGTC AGTG | GACTTTTACAATCGATTCCCCAAACCCCTTTATGGCAGCA ACACTGTGGTCGGTGCTCGCAGGCTCGGCA SEQ ID NO: 255 |
| NGSPLEx 256_124 | TCGCGAAAT TCGGTTGT SEQ ID NO: 131 | GACAC TGAG | TTCTTGTAATTTGCATAATCCTCAAGAATGGAATCCACTG GTCGGTGCTCGCAGGCTCGGCA SEQ ID NO: 256 |

TABLE 2-continued

List of 256 precursor for the 256plex of in FIG. 8

| NGSPLEx 256_125 | TCGCGAAAT TCGGTTGT SEQ ID NO: 131 | GAGAG AGAG | TGGTCCCAGGGGAAAGGAAGAGGCCAGTTGGTCCAGTT TTGATTGGTCGGTGCTCGCAGGCTCGGCA SEQ ID NO: 257 |
|---|---|---|---|
| NGSPLEx 256_126 | TCGCGAAAT TCGGTTGT SEQ ID NO: 131 | GACTG ACTG | CAGGGGACGGTACTCCACATCCTCTCTGAGCAGGCGGT GGTCGGTGCTCGCAGGCTCGGCA SEQ ID NO: 258 |
| NGSPLEx 256_127 | TCGCGAAAT TCGGTTGT SEQ ID NO: 131 | CTCTG AGTG | CTTCTACATCATCAGCTGCCATACGAAGAAGGGACTCCG TTGGTCGGTGCTCGCAGGCTCGGCA SEQ ID NO: 259 |
| NGSPLEx 256_128 | TCGCGAAAT TCGGTTGT SEQ ID NO: 131 | GACTG ACAG | GCCACCAGCATCAACCTTCTTGGCTTCGGGTTTCTTCTG GTCGGTGCTCGCAGGCTCGGCA SEQ ID NO: 260 |
| NGSPLEx 256_129 | TCGCGAAAT TCGGTTGT SEQ ID NO: 131 | GTCTG AGAG | CCCCACCGGTGCTCTTGGTACGAAGATCCATGCTAAATT CCCCATGGTCGGTGCTCGCAGGCTCGGCA SEQ ID NO: 261 |
| NGSPLEx 256_130 | TCGCGAAAT TCGGTTGT SEQ ID NO: 131 | CAGAG TGAG | TTGTATATAAGATTACTTTATTCCTGCATCTTCTCAATGGT TTCTTTGGTCGGTGCTCGCAGGCTCGGCA SEQ ID NO: 262 |
| NGSPLEx 256_131 | TCGCGAAAT TCGGTTGT SEQ ID NO: 131 | GACAG ACTG | CATTTTCATGGTTTTGTAGAGCTTCAATTTTGTCTAAGCCT CCATGGTCGGTGCTCGCAGGCTCGGCA SEQ ID NO: 263 |
| NGSPLEx 256_132 | TCGCGAAAT TCGGTTGT SEQ ID NO: 131 | GTGAC TGTG | CATAGTTGTCAACAAGCACAGTGAAAGCGCCATTCTCTTT ACATGGTCGGTGCTCGCAGGCTCGGCA SEQ ID NO: 264 |
| NGSPLEx 256_133 | TCGCGAAAT TCGGTTGT SEQ ID NO: 131 | GTCTC AGTG | GCCAACAGCATGCTGGGTAACATTGTAGACTCTTCCTGG TCGGTGCTCGCAGGCTCGGCA SEQ ID NO: 265 |
| NGSPLEx 256_134 | TCGCGAAAT TCGGTTGT SEQ ID NO: 131 | CTGAC AGAG | AGGAGATCTCCACAGGGGCTGGACGGTTCATTATGGCAA ATTGGTCGGTGCTCGCAGGCTCGGCA SEQ ID NO: 266 |
| NGSPLEx 256_135 | TCGCGAAAT TCGGTTGT SEQ ID NO: 131 | CTGAG TCAG | TTGAGCATCTCGTAGTGGGAGGCTGGCCGCTGTTGACA GGAGAGTGGTCGGTGCTCGCAGGCTCGGCA SEQ ID NO: 267 |
| NGSPLEx 256_136 | TCGCGAAAT TCGGTTGT SEQ ID NO: 131 | CAGAC TGTG | CTCCCTTTCCCCAGTAGTTTCGGTTTCTCAACAGTTTCCT TGGTCGGTGCTCGCAGGCTCGGCA SEQ ID NO: 268 |
| NGSPLEx 256_137 | TCGCGAAAT TCGGTTGT SEQ ID NO: 131 | GTGAG ACTG | TGGTTTTTAACAGGTTTAACCAATCATCTACTATCTGATTG GTCGGTGCTCGCAGGCTCGGCA SEQ ID NO: 269 |
| NGSPLEx 256_138 | TCGCGAAAT TCGGTTGT SEQ ID NO: 131 | CTGAC AGTG | CCTTCTGTCCTCATGTTGGCAGAGATATCTACTCTGTGGT CGGTGCTCGCAGGCTCGGCA SEQ ID NO: 270 |
| NGSPLEx 256_139 | TCGCGAAAT TCGGTTGT SEQ ID NO: 131 | GACAG AGAG | GGATTCCAGTAGCCAGGTTGGTACGGGACGGCATCATAA CATGGTCGGTGCTCGCAGGCTCGGCA SEQ ID NO: 271 |
| NGSPLEx 256_140 | TCGCGAAAT TCGGTTGT SEQ ID NO: 131 | CTGAG AGTG | CTTCAGCGGAGGCATTTCCACCAATGAGCGAGTCATTGG TCGGTGCTCGCAGGCTCGGCA SEQ ID NO: 272 |
| NGSPLEx 256_141 | TCGCGAAAT TCGGTTGT SEQ ID NO: 131 | GTCAG ACAG | GTTTATGGTAAAGCTTAGCCTTCAGACCAATCATTTTCTTT GCTGGTCGGTGCTCGCAGGCTCGGCA SEQ ID NO: 273 |
| NGSPLEx 256_142 | TCGCGAAAT TCGGTTGT SEQ ID NO: 131 | CTCAC TCTG | GGCCGCAAAAGGGAAGAGAACTACACGCTGCTTCCGGT TCTTGGTCGGTGCTCGCAGGCTCGGCA SEQ ID NO: 274 |
| NGSPLEx 256_143 | TCGCGAAAT TCGGTTGT SEQ ID NO: 131 | GAGTG TGAG | TTGTTCACTGGGTCTTTGTCTTTCTTGGCCGACTTTCCAG CGTCTGGTCGGTGCTCGCAGGCTCGGCA SEQ ID NO: 275 |

TABLE 2-continued

List of 256 precursor for the 256plex of in FIG. 8

| | | | |
|---|---|---|---|
| NGSPLEx 256_144 | TCGCGAAAT TCGGTTGT SEQ ID NO: 131 | GAGAC AGTG | CTTCCCAGTTAAGGCTCTTTATTTTATTTTGAACACTTTTT TGCATTGGTCGGTGCTCGCAGGCTCGGCA SEQ ID NO: 276 |
| NGSPLEx 256_145 | TCGCGAAAT TCGGTTGT SEQ ID NO: 131 | CAGAC ACAG | ATCAACAAGCCACGGTTTTAGCTCTTCAGGAATCTTTACT TTAACTGGTCGGTGCTCGCAGGCTCGGCA SEQ ID NO: 277 |
| NGSPLEx 256_146 | TCGCGAAAT TCGGTTGT SEQ ID NO: 131 | CACAC TCTG | GGTGGTTCCTTGAGGGCTTTGATGATCAGGGCAGAGGC AGAAGGCTGGTCGGTGCTCGCAGGCTCGGCA SEQ ID NO: 278 |
| NGSPLEx 256_147 | TCGCGAAAT TCGGTTGT SEQ ID NO: 131 | GTGTC AGTG | AATTCACACACCTCACAGTAAACATCAGACTTTGCTGGGA CCTCTGGTCGGTGCTCGCAGGCTCGGCA SEQ ID NO: 279 |
| NGSPLEx 256_148 | TCGCGAAAT TCGGTTGT SEQ ID NO: 131 | GTCTG ACTG | TGTCATCCTTCTTGCCACCTCCAGGACCATGACCACCAC TCTGACTGGTCGGTGCTCGCAGGCTCGGCA SEQ ID NO: 280 |
| NGSPLEx 256_149 | TCGCGAAAT TCGGTTGT SEQ ID NO: 131 | GTGAG TCTG | GAGCAAGGAGGGCTGGAAGCTGTTAGTCAGAGTGTTGA AGCTGGTCGGTGCTCGCAGGCTCGGCA SEQ ID NO: 281 |
| NGSPLEx 256_150 | TCGCGAAAT TCGGTTGT SEQ ID NO: 131 | CACAC TCAG | AAAATTGTGCGGATGTGGCTTCTGGAAGACCTTCATTCTA AAGCTGGTCGGTGCTCGCAGGCTCGGCA SEQ ID NO: 282 |
| NGSPLEx 256_151 | TCGCGAAAT TCGGTTGT SEQ ID NO: 131 | CACTG TGTG | GCAGTTTTCTAATTGAGAATGTAATCTTGGTCTTTAAAGA ACATGGTCGGTGCTCGCAGGCTCGGCA SEQ ID NO: 283 |
| NGSPLEx 256_152 | TCGCGAAAT TCGGTTGT SEQ ID NO: 131 | CACAC ACTG | GTTTCTGCATCAGCCCGCTCATCAAATCCAGGGAAGTTG GTCGGTGCTCGCAGGCTCGGCA SEQ ID NO: 284 |
| NGSPLEx 256_153 | TCGCGAAAT TCGGTTGT SEQ ID NO: 131 | CTGAG TCTG | CCAGCGGCAACCTCAGCCAAGTAACGGTAGTAATCTCCT TGGTCGGTGCTCGCAGGCTCGGCA SEQ ID NO: 285 |
| NGSPLEx 256_154 | TCGCGAAAT TCGGTTGT SEQ ID NO: 131 | GACAC TGTG | GTGATCGGGGTTTCTTGATACCATTTCTGTGCCATTTTCG GGTGGTCGGTGCTCGCAGGCTCGGCA SEQ ID NO: 286 |
| NGSPLEx 256_155 | TCGCGAAAT TCGGTTGT SEQ ID NO: 131 | GTCAC AGAG | AGGAGGTCCTGCTGAGTTGGTGAATCTCTGGTAACGGTG GTGGTCGGTGCTCGCAGGCTCGGCA SEQ ID NO: 287 |
| NGSPLEx 256_156 | TCGCGAAAT TCGGTTGT SEQ ID NO: 131 | CTGAG TGAG | CCTGGTTTTCTAAAATTCTTCAGGTCAATAGTCAAGCCTT TGGTCGGTGCTCGCAGGCTCGGCA SEQ ID NO: 288 |
| NGSPLEx 256_157 | TCGCGAAAT TCGGTTGT SEQ ID NO: 131 | CTGAC ACAG | ACAATATCACCTTTCTTATAGATTCGCATATATGTGGCCA AAGGATGGTCGGTGCTCGCAGGCTCGGCA SEQ ID NO: 289 |
| NGSPLEx 256_158 | TCGCGAAAT TCGGTTGT SEQ ID NO: 131 | CTCTG TGTG | AAACAAAACAAGAAAAAGTAATCTGCTAAAAACTATAGGG TCCCCTGGTCGGTGCTCGCAGGCTCGGCA SEQ ID NO: 290 |
| NGSPLEx 256_159 | TCGCGAAAT TCGGTTGT SEQ ID NO: 131 | CAGTG ACAG | TAGAATCTTTTTTATTCAGAAAAAAAAAAACCCCAAAAAACA TGGTCGGTGCTCGCAGGCTCGGCA SEQ ID NO: 291 |
| NGSPLEx 256_160 | TCGCGAAAT TCGGTTGT SEQ ID NO: 131 | CTGTG AGAG | AGTTTAATAAATACAAATACTCGTTTCTTTTTGATTAGTGT GGTCGGTGCTCGCAGGCTCGGCA SEQ ID NO: 292 |
| NGSPLEx 256_161 | TCGCGAAAT TCGGTTGT SEQ ID NO: 131 | GTGAC TCAG | ACTTTGAGATTCTTTTCTTTTGCGCCTCTTATCAAGTCAG CTGGTCGGTGCTCGCAGGCTCGGCA SEQ ID NO: 293 |
| NGSPLEx 256_162 | TCGCGAAAT TCGGTTGT SEQ ID NO: 131 | CACAG AGAG | AGCCTGGTTGGAGGATTCCTAGTTTTATACATGAGAAATA GTGGTCGGTGCTCGCAGGCTCGGCA SEQ ID NO: 294 |

TABLE 2-continued

List of 256 precursor for the 256plex of in FIG. 8

| | | | |
|---|---|---|---|
| NGSPLEx 256_163 | TCGCGAAAT TCGGTTGT SEQ ID NO: 131 | GAGTC AGAG | GTTCCCAAGATAGAAGAGTAGGTATGAAGCAATTCTGAC TCTGGTCGGTGCTCGCAGGCTCGGCA SEQ ID NO: 295 |
| NGSPLEx 256_164 | TCGCGAAAT TCGGTTGT SEQ ID NO: 131 | GACTC AGTG | TCTTTGTATGAGTCTTCATTCAGTGTATCAAGTTCATGGT CGGTGCTCGCAGGCTCGGCA SEQ ID NO: 296 |
| NGSPLEx 256_165 | TCGCGAAAT TCGGTTGT SEQ ID NO: 131 | CTGTG ACTG | ACAGATGAATGTAGGATTGATGCAAGTCACTTCCAGGAA TGGTCGGTGCTCGCAGGCTCGGCA SEQ ID NO: 297 |
| NGSPLEx 256_166 | TCGCGAAAT TCGGTTGT SEQ ID NO: 131 | GTGAG TGAG | TCGCTTTTAGCTCCTCGAGTTTCTTCTGCTCCTCTTTTGT TTTGGTCGGTGCTCGCAGGCTCGGCA SEQ ID NO: 298 |
| NGSPLEx 256_167 | TCGCGAAAT TCGGTTGT SEQ ID NO: 131 | CTCAG AGTG | TACTTCTGGGCCGTCACAGGGGAGGGCAGGTGGATGGT GATCATGGTCGGTGCTCGCAGGCTCGGCA SEQ ID NO: 299 |
| NGSPLEx 256_168 | TCGCGAAAT TCGGTTGT SEQ ID NO: 131 | CACTC ACTG | TGGTGCCGGATGAACTTCTTGGTTCTCTTTTTGACGATCT TGTGGTCGGTGCTCGCAGGCTCGGCA SEQ ID NO: 300 |
| NGSPLEx 256_169 | TCGCGAAAT TCGGTTGT SEQ ID NO: 131 | GAGTC TGAG | TATGCCTAGAACTTTCACGCCAATTATTTCACCTCTTGCA CATATGGTCGGTGCTCGCAGGCTCGGCA SEQ ID NO: 301 |
| NGSPLEx 256_170 | TCGCGAAAT TCGGTTGT SEQ ID NO: 131 | CACAG TCTG | CCCAGGTCCTGTGATGTTATTGAAGGAAGCAAGGGCAG GGTGGTCGGTGCTCGCAGGCTCGGCA SEQ ID NO: 302 |
| NGSPLEx 256_171 | TCGCGAAAT TCGGTTGT SEQ ID NO: 131 | CAGAC AGTG | GTCCCTTTGTTTTCTTCTTCTTTTTCCCCACTCTAGTTGGT ACAGGTGGTCGGTGCTCGCAGGCTCGGCA SEQ ID NO: 303 |
| NGSPLEx 256_172 | TCGCGAAAT TCGGTTGT SEQ ID NO: 131 | CAGAC TCTG | CCATCGATGTTGGTGTTGAGTACTCGCAAAATATGCTGG TCGGTGCTCGCAGGCTCGGCA SEQ ID NO: 304 |
| NGSPLEx 256_173 | TCGCGAAAT TCGGTTGT SEQ ID NO: 131 | GTGTG TCTG | GATACCACAGAATCAGCAGGGTGAGAAACAATTGCACAA AAGACTTGGTCGGTGCTCGCAGGCTCGGCA SEQ ID NO: 305 |
| NGSPLEx 256_174 | TCGCGAAAT TCGGTTGT SEQ ID NO: 131 | GACTC TCTG | AAAGCTTGAGATCACTTGAGGCCAGAGTTTTCAGACCTG GTCGGTGCTCGCAGGCTCGGCA SEQ ID NO: 306 |
| NGSPLEx 256_175 | TCGCGAAAT TCGGTTGT SEQ ID NO: 131 | GACAG TCTG | CGGGTGTGGACGGGCGGCGGATCGGCAAAGGCGAGGC TCTTGGTCGGTGCTCGCAGGCTCGGCA SEQ ID NO: 307 |
| NGSPLEx 256_176 | TCGCGAAAT TCGGTTGT SEQ ID NO: 131 | CACAG ACAG | CAGCGCGAGTGCAGAGCATGGTGGTAGATGTGGCAGAG GATGGCATGGTCGGTGCTCGCAGGCTCGGCA SEQ ID NO: 308 |
| NGSPLEx 256_177 | TCGCGAAAT TCGGTTGT SEQ ID NO: 131 | CTGAG TGTG | GACCCTCATAGACAGCAGACAGAAGAGGAGTAATATGAT GTTTATTGGTCGGTGCTCGCAGGCTCGGCA SEQ ID NO: 309 |
| NGSPLEx 256_178 | TCGCGAAAT TCGGTTGT SEQ ID NO: 131 | GTGTG AGTG | AAATACACTTTTAATTGATTTCAGATAAAAACTACTTGGTC GGTGCTCGCAGGCTCGGCA SEQ ID NO: 310 |
| NGSPLEx 256_179 | TCGCGAAAT TCGGTTGT SEQ ID NO: 131 | GTGAG TCAG | GCCGCGCAAGCCGGAGAGGAGAAGAAGAGAAGGAGG GTTAGGCTGGTCGGTGCTCGCAGGCTCGGCA SEQ ID NO: 311 |
| NGSPLEx 256_180 | TCGCGAAAT TCGGTTGT SEQ ID NO: 131 | CAGTC ACTG | CAAATCTCAGGGAAGCAGTGATGGAGGACACAATCTGGC TGGTCGGTGCTCGCAGGCTCGGCA SEQ ID NO: 312 |
| NGSPLEx 256_181 | TCGCGAAAT TCGGTTGT SEQ ID NO: 131 | CACTC TGTG | GGTCATAGTGGAGGGTAAGAGCTTTTACATCCCGCAGTG GTCGGTGCTCGCAGGCTCGGCA SEQ ID NO: 313 |

TABLE 2-continued

List of 256 precursor for the 256plex of in FIG. 8

| Name | Part 1 | Part 2 | Part 3 |
|---|---|---|---|
| NGSPLEx 256_182 | TCGCGAAAT TCGGTTGT SEQ ID NO: 131 | CACAG TGTG | GATCCATCATTTCTCCTTTAAGCTTATCTTCCAAAATGGTC GGTGCTCGCAGGCTCGGCA SEQ ID NO: 314 |
| NGSPLEx 256_183 | TCGCGAAAT TCGGTTGT SEQ ID NO: 131 | GTCTG TCAG | TGTTTACTGATTTCTGTCTGGTTAAACATCCAATACTGGT CGGTGCTCGCAGGCTCGGCA SEQ ID NO: 315 |
| NGSPLEx 256_184 | TCGCGAAAT TCGGTTGT SEQ ID NO: 131 | GACAG TCAG | GCCTATCTCTTTCCATCAGACTCCAGTGATACCCAATGGT CGGTGCTCGCAGGCTCGGCA SEQ ID NO: 316 |
| NGSPLEx 256_185 | TCGCGAAAT TCGGTTGT SEQ ID NO: 131 | GACAG AGTG | CCTGTAATCTCAGCACGTTGGGAGGCGAGGTGGGTGGA TGTGGTCGGTGCTCGCAGGCTCGGCA SEQ ID NO: 317 |
| NGSPLEx 256_186 | TCGCGAAAT TCGGTTGT SEQ ID NO: 131 | CTCTC ACAG | CTTAAATACCAGATACATTTTTAGTCCTCTACATAATGGTC GGTGCTCGCAGGCTCGGCA SEQ ID NO: 318 |
| NGSPLEx 256_187 | TCGCGAAAT TCGGTTGT SEQ ID NO: 131 | GACAC AGTG | GTTTTTTGGAAGATTCGGGTTCAGCACAGGATTCCATTTG GTCGGTGCTCGCAGGCTCGGCA SEQ ID NO: 319 |
| NGSPLEx 256_188 | TCGCGAAAT TCGGTTGT SEQ ID NO: 131 | GTCTC AGAG | TGATATCCTTGTTTTTAACTGTTGTGGCTTGCTGAATCAA ATGGTCGGTGCTCGCAGGCTCGGCA SEQ ID NO: 320 |
| NGSPLEx 256_189 | TCGCGAAAT TCGGTTGT SEQ ID NO: 131 | CAGAG ACAG | AAGACGGAGTAGTTAAGAGCCAGGCCTAATCGGATGGTG GTCGGTGCTCGCAGGCTCGGCA SEQ ID NO: 321 |
| NGSPLEx 256_190 | TCGCGAAAT TCGGTTGT SEQ ID NO: 131 | CTGTC ACTG | CGAGTTCCAGAGACAATATCAAAATTACCCTCCTTTTGGT CGGTGCTCGCAGGCTCGGCA SEQ ID NO: 322 |
| NGSPLEx 256_191 | TCGCGAAAT TCGGTTGT SEQ ID NO: 131 | CTCTG TCTG | GGTGAGAGAACTAATAGCAACCAGGCAACTGAGGACGAA GTTGGTCGGTGCTCGCAGGCTCGGCA SEQ ID NO: 323 |
| NGSPLEx 256_192 | TCGCGAAAT TCGGTTGT SEQ ID NO: 131 | CTCAC ACTG | TTGGGGTGCTTTATCTTCTTTGAGTTTTCGCACAAGATGG TCGGTGCTCGCAGGCTCGGCA SEQ ID NO: 324 |
| NGSPLEx 256_193 | TCGCGAAAT TCGGTTGT SEQ ID NO: 131 | CTGTG TGTG | GGGCATGGGCTCACATTCACTTCCTTTATAACTCCATCCT GGTCGGTGCTCGCAGGCTCGGCA SEQ ID NO: 325 |
| NGSPLEx 256_194 | TCGCGAAAT TCGGTTGT SEQ ID NO: 131 | CAGTC TCAG | GCCTGTTTTCCCTTTGCTCCCCTTTTCCCTTTTGTTTGCA CTGGTCGGTGCTCGCAGGCTCGGCA SEQ ID NO: 326 |
| NGSPLEx 256_195 | TCGCGAAAT TCGGTTGT SEQ ID NO: 131 | GAGAC TCTG | CATTTTTCCGATAGTTAATAGTAATGGAGTAATAATGTTG GTCGGTGCTCGCAGGCTCGGCA SEQ ID NO: 327 |
| NGSPLEx 256_196 | TCGCGAAAT TCGGTTGT SEQ ID NO: 131 | GTGAC TCTG | CACTTGGCCCTTTCTCTTCTTATCTCCTCCCAGTTCTGGT CGGTGCTCGCAGGCTCGGCA SEQ ID NO: 328 |
| NGSPLEx 256_197 | TCGCGAAAT TCGGTTGT SEQ ID NO: 131 | GACTG TCAG | TCGTCCTCCTCCTCTTCATCCACACCATCCACCTCGGTG GTCGGTGCTCGCAGGCTCGGCA SEQ ID NO: 329 |
| NGSPLEx 256_198 | TCGCGAAAT TCGGTTGT SEQ ID NO: 131 | GACAG TGAG | CCTCCTCTTCCTCCCCACCTTCTTCCTCTTCTTCGTCTAC TGGTCGGTGCTCGCAGGCTCGGCA SEQ ID NO: 330 |
| NGSPLEx 256_199 | TCGCGAAAT TCGGTTGT SEQ ID NO: 131 | GACTG AGAG | ACGATGGCGGAGAAAGGAAGAGGAGGGAAGCTGGCGG AATGGTCGGTGCTCGCAGGCTCGGCA SEQ ID NO: 331 |
| NGSPLEx 256_200 | TCGCGAAAT TCGGTTGT SEQ ID NO: 131 | GAGAG ACAG | TATAATACAAAAAAGACCAAAAAACAAAACAAAACAAAA CATCAATGGTCGGTGCTCGCAGGCTCGGCA SEQ ID NO: 332 |

TABLE 2-continued

List of 256 precursor for the 256plex of in FIG. 8

| | | | |
|---|---|---|---|
| NGSPLEx 256_201 | TCGCGAAAT TCGGTTGT SEQ ID NO: 131 | CTCAC TGAG | AACACAAGTGTGTTGTTGTCTTCTATCTTCTTCATGGCAT GGTCGGTGCTCGCAGGCTCGGCA SEQ ID NO: 333 |
| NGSPLEx 256_202 | TCGCGAAAT TCGGTTGT SEQ ID NO: 131 | GAGTG ACAG | ACCAAAACCACAATTTCTGCAGTTTAAAATGTTTCACTTG GTCGGTGCTCGCAGGCTCGGCA SEQ ID NO: 334 |
| NGSPLEx 256_203 | TCGCGAAAT TCGGTTGT SEQ ID NO: 131 | CACAG AGTG | CCGCTGCTCGGTCCCCAGGCCCCGCCGTCCTTGCTGT TTGGTCGGTGCTCGCAGGCTCGGCA SEQ ID NO: 335 |
| NGSPLEx 256_204 | TCGCGAAAT TCGGTTGT SEQ ID NO: 131 | GACTG AGTG | CGAGATCCTGGTGCTCCCACTCGCGTTGCTGCAGCAAGA AATGGTCGGTGCTCGCAGGCTCGGCA SEQ ID NO: 336 |
| NGSPLEx 256_205 | TCGCGAAAT TCGGTTGT SEQ ID NO: 131 | CACTG TCAG | GCCGGCCGGGGTGGGGAACGAGCGCCGGGTTCCGTCC TGGTCGGTGCTCGCAGGCTCGGCA SEQ ID NO: 337 |
| NGSPLEx 256_206 | TCGCGAAAT TCGGTTGT SEQ ID NO: 131 | GTCAG AGTG | TCTCTGCCACCGCTGGTGCTGCTGTCTCCCACTCGGTGG TCGGTGCTCGCAGGCTCGGCA SEQ ID NO: 338 |
| NGSPLEx 256_207 | TCGCGAAAT TCGGTTGT SEQ ID NO: 131 | CTGTG AGTG | CATCGAAGACGCTCGCTTCAGAAATGTCCCTGACTGCTG CGTGGTCGGTGCTCGCAGGCTCGGCA SEQ ID NO: 339 |
| NGSPLEx 256_208 | TCGCGAAAT TCGGTTGT SEQ ID NO: 131 | CTGAC ACTG | GTCTTTCAGGTCAATGTAGTGCTGCTTCAGGTGTTCTTCA GAGTGGTCGGTGCTCGCAGGCTCGGCA SEQ ID NO: 340 |
| NGSPLEx 256_209 | TCGCGAAAT TCGGTTGT SEQ ID NO: 131 | CTGTC TGAG | CATCAGCATAGCCTCCGATGACCATGGTGTTCCACAAAG GGTTGGTCGGTGCTCGCAGGCTCGGCA SEQ ID NO: 341 |
| NGSPLEx 256_210 | TCGCGAAAT TCGGTTGT SEQ ID NO: 131 | CACTG ACTG | GATGCCCAGAATCAGGGCCCAGATGTTCAGGCACTTGG CGGTGGTGGTCGGTGCTCGCAGGCTCGGCA SEQ ID NO: 342 |
| NGSPLEx 256_211 | TCGCGAAAT TCGGTTGT SEQ ID NO: 131 | CAGTG TCAG | AGAACCGGAAGAGAAAGGGGCTGCGGTGCAGCACGGGA AATAGGGTTGGTCGGTGCTCGCAGGCTCGGCA SEQ ID NO: 343 |
| NGSPLEx 256_212 | TCGCGAAAT TCGGTTGT SEQ ID NO: 131 | GTGAG AGAG | CCCCCCAACCCTCACTGTTTCCCGTTGCCATTGATGGTG GTCGGTGCTCGCAGGCTCGGCA SEQ ID NO: 344 |
| NGSPLEx 256_213 | TCGCGAAAT TCGGTTGT SEQ ID NO: 131 | CACTG ACAG | ACCTCATAGGTGCCTGCGTGGGCGCTCTTGTGGTCCAG GCTCTGGTCGGTGCTCGCAGGCTCGGCA SEQ ID NO: 345 |
| NGSPLEx 256_214 | TCGCGAAAT TCGGTTGT SEQ ID NO: 131 | GAGAC TGTG | ACAGGAGTCTTGCCCAAGCCCTGTCATGTCAGTGTGTGT GTGGTCGGTGCTCGCAGGCTCGGCA SEQ ID NO: 346 |
| NGSPLEx 256_215 | TCGCGAAAT TCGGTTGT SEQ ID NO: 131 | CAGTG TCTG | CTTCTTCAAGGTGATATAGACGCTGCCCGACGTCCGGTG GTCGGTGCTCGCAGGCTCGGCA SEQ ID NO: 347 |
| NGSPLEx 256_216 | TCGCGAAAT TCGGTTGT SEQ ID NO: 131 | GTGTC TGAG | GCCATCTGGGCCATCAGACCTGGCTGCCGGGCGCATG GTCGGTGCTCGCAGGCTCGGCA SEQ ID NO: 348 |
| NGSPLEx 256_217 | TCGCGAAAT TCGGTTGT SEQ ID NO: 131 | GACTC TGAG | GCTTCTTGGGAAATGAAGCCACAGCCAGCTCATATATGT GGTCGGTGCTCGCAGGCTCGGCA SEQ ID NO: 349 |
| NGSPLEx 256_218 | TCGCGAAAT TCGGTTGT SEQ ID NO: 131 | CAGAG TCTG | CTCATCCACGATGGCTGCTATCGGTAAACAGTTAAAACA GTCTGTTGGTCGGTGCTCGCAGGCTCGGCA SEQ ID NO: 350 |
| NGSPLEx 256_219 | TCGCGAAAT TCGGTTGT SEQ ID NO: 131 | GTCAG AGAG | TGACCCGCTCGATCGGAGCCACGGCCGTCTTGGAGATG GTGGTCGGTGCTCGCAGGCTCGGCA SEQ ID NO: 351 |

TABLE 2-continued

List of 256 precursor for the 256plex of in FIG. 8

| | | | |
|---|---|---|---|
| NGSPLEx 256_220 | TCGCGAAAT TCGGTTGT SEQ ID NO: 131 | CAGTC AGTG | GGGTGATCAGCTGTGAGGCATTGAACTTGGCCACCACAC TCTTGGTCGGTGCTCGCAGGCTCGGCA SEQ ID NO: 352 |
| NGSPLEx 256_221 | TCGCGAAAT TCGGTTGT SEQ ID NO: 131 | GTGTC TGTG | ACAGCACAGTAACAAAGTTATTAGGAAAACAGGACTACC ACAAAGATGGTCGGTGCTCGCAGGCTCGGCA SEQ ID NO: 353 |
| NGSPLEx 256_222 | TCGCGAAAT TCGGTTGT SEQ ID NO: 131 | CAGAC TGAG | ACCAATGTTTTTTAGAATAGTGGCACCATCATTGGTTGGT CGGTGCTCGCAGGCTCGGCA SEQ ID NO: 354 |
| NGSPLEx 256_223 | TCGCGAAAT TCGGTTGT SEQ ID NO: 131 | GACTG TCTG | GCAGTTTACGCTGTCTAGCCAGAGTTTCACCGTAAATATG ATTGGTCGGTGCTCGCAGGCTCGGCA SEQ ID NO: 355 |
| NGSPLEx 256_224 | TCGCGAAAT TCGGTTGT SEQ ID NO: 131 | GTCTC ACAG | CACTCTTTCACTTAAAGAGATATAGCTAGAAGGATTCACA GTGGTCGGTGCTCGCAGGCTCGGCA SEQ ID NO: 356 |
| NGSPLEx 256_225 | TCGCGAAAT TCGGTTGT SEQ ID NO: 131 | GACAC ACAG | ACCTTCAGGTCGTCCAGCTGTTTCAGCAGCTCCTCCTGG TCGGTGCTCGCAGGCTCGGCA SEQ ID NO: 357 |
| NGSPLEx 256_226 | TCGCGAAAT TCGGTTGT SEQ ID NO: 131 | CACAG TCAG | GCCGTCAACTTGCGTCGGAACATGGTCCCCGCTTCTCGC TCTGGTCTGGTCGGTGCTCGCAGGCTCGGCA SEQ ID NO: 358 |
| NGSPLEx 256_227 | TCGCGAAAT TCGGTTGT SEQ ID NO: 131 | GTGAC ACTG | CGATCCAAAAAGTGCGCGATGCGAGTAGTCAAGTCGTAC TGGTCGGTGCTCGCAGGCTCGGCA SEQ ID NO: 359 |
| NGSPLEx 256_228 | TCGCGAAAT TCGGTTGT SEQ ID NO: 131 | CTGTC TCTG | AGACAATGGTCCCTCTATTTCAACACCTTTTTCGGTGACA GTGTGGTCGGTGCTCGCAGGCTCGGCA SEQ ID NO: 360 |
| NGSPLEx 256_229 | TCGCGAAAT TCGGTTGT SEQ ID NO: 131 | GAGTC ACTG | GGTGATCTTGCTCTTGCTCCTTTCGATGGTCACCACCCC TCCATGGTCGGTGCTCGCAGGCTCGGCA SEQ ID NO: 361 |
| NGSPLEx 256_230 | TCGCGAAAT TCGGTTGT SEQ ID NO: 131 | CTCTC TGTG | AACAGCCTTTAGTTCTACAGGAAATGGCACTGATGGACA GAAGTGGTCGGTGCTCGCAGGCTCGGCA SEQ ID NO: 362 |
| NGSPLEx 256_231 | TCGCGAAAT TCGGTTGT SEQ ID NO: 131 | GAGAG TCTG | CCGGCTGTCTGTCTTGGTGCTCTCCACCTTCCGCACCAC CTCTGGTCGGTGCTCGCAGGCTCGGCA SEQ ID NO: 363 |
| NGSPLEx 256_232 | TCGCGAAAT TCGGTTGT SEQ ID NO: 131 | CTGAG AGAG | GGGAGGTGAACCCAGAACCAGTTCCCCCACCAAAGCTG TGGAAATGGTCGGTGCTCGCAGGCTCGGCA SEQ ID NO: 364 |
| NGSPLEx 256_233 | TCGCGAAAT TCGGTTGT SEQ ID NO: 131 | GAGTG AGTG | TCACAACAGGGGAGGCCTTGGTGAAAGCTGGGTGGAAA ACCCTGGTCGGTGCTCGCAGGCTCGGCA SEQ ID NO: 365 |
| NGSPLEx 256_234 | TCGCGAAAT TCGGTTGT SEQ ID NO: 131 | CTGTG ACAG | GTGGAGTCTAGAGGATCCACAGCTGGATAGATGCCCAG CTTGGTCGGTGCTCGCAGGCTCGGCA SEQ ID NO: 366 |
| NGSPLEx 256_235 | TCGCGAAAT TCGGTTGT SEQ ID NO: 131 | CACTG AGAG | AGGTAAAGGCCTGCAGCGATGAAACAGTTGTAGCTGACT TGCTTGGTCGGTGCTCGCAGGCTCGGCA SEQ ID NO: 367 |
| NGSPLEx 256_236 | TCGCGAAAT TCGGTTGT SEQ ID NO: 131 | CTCAG TCAG | TCATTGATTGGTTGCCCGTCAAATCGGAATCTGATCTGCT GGTCGGTGCTCGCAGGCTCGGCA SEQ ID NO: 368 |
| NGSPLEx 256_237 | TCGCGAAAT TCGGTTGT SEQ ID NO: 131 | CTGTG TGAG | GCTGAAACTTTCACAGGCTTCACAATCTTTTGCTTAGGTG CTGCCTTGGTCGGTGCTCGCAGGCTCGGCA SEQ ID NO: 369 |
| NGSPLEx 256_238 | TCGCGAAAT TCGGTTGT SEQ ID NO: 131 | GTGAC AGTG | CACATAGAAGTCCAGGCCGTAGATACCAATGCTTGGTGG TCGGTGCTCGCAGGCTCGGCA SEQ ID NO: 370 |

TABLE 2-continued

List of 256 precursor for the 256plex of in FIG. 8

| NGSPLEx 256_239 | TCGCGAAAT TCGGTTGT SEQ ID NO: 131 | CTGAC TCAG | ACCATGCCCAGCACATCCTGCACATGCTGGCCCAGGTTG GAGCCCTGGTCGGTGCTCGCAGGCTCGGCA SEQ ID NO: 371 |
|---|---|---|---|
| NGSPLEx 256_240 | TCGCGAAAT TCGGTTGT SEQ ID NO: 131 | GTCAG ACTG | GGTGATGGTAGCCTTTCTGCCCAGCGCGTGCCACAGTG GTCGGTGCTCGCAGGCTCGGCA SEQ ID NO: 372 |
| NGSPLEx 256_241 | TCGCGAAAT TCGGTTGT SEQ ID NO: 131 | CACTG AGTG | GCCGCATCCGCGTCAGATTCCCAAACTCGCGGCCCATTG TGGCTGGTCGGTGCTCGCAGGCTCGGCA SEQ ID NO: 373 |
| NGSPLEx 256_242 | TCGCGAAAT TCGGTTGT SEQ ID NO: 131 | CTCAG AGAG | TTGCTGTCACCAGCAACGTTGCCACGACGAACATCCTTG ACAGACATGGTCGGTGCTCGCAGGCTCGGCA SEQ ID NO: 374 |
| NGSPLEx 256_243 | TCGCGAAAT TCGGTTGT SEQ ID NO: 131 | CAGTC ACAG | GCTGGTATAAGGTGGTCTGGTTGACTTCTGGTGTCCCCA CGTGGTCGGTGCTCGCAGGCTCGGCA SEQ ID NO: 375 |
| NGSPLEx 256_244 | TCGCGAAAT TCGGTTGT SEQ ID NO: 131 | GAGAG AGTG | CGGCATCCTCTCAGGAGGGCCGGTCCGGGTCTCAGCGC GCCTGGTCGGTGCTCGCAGGCTCGGCA SEQ ID NO: 376 |
| NGSPLEx 256_245 | TCGCGAAAT TCGGTTGT SEQ ID NO: 131 | CAGAC AGAG | AGGTTAACCATGTGCCCGTCGATGTCCTTGGCGGAAAAC TCGTGCATGGTCGGTGCTCGCAGGCTCGGCA SEQ ID NO: 377 |
| NGSPLEx 256_246 | TCGCGAAAT TCGGTTGT SEQ ID NO: 131 | GAGTC TGTG | ACCACAAACTCTTCCACCAGCCAGCATGGCAAATTTGAG GTGCTTGTGGTCGGTGCTCGCAGGCTCGGCA SEQ ID NO: 378 |
| NGSPLEx 256_247 | TCGCGAAAT TCGGTTGT SEQ ID NO: 131 | CTGAC TCTG | TGGAGATTGCAGTGAGCTGAGATCACACCACTGGGCTCC AGCCTTGGTCGGTGCTCGCAGGCTCGGCA SEQ ID NO: 379 |
| NGSPLEx 256_248 | TCGCGAAAT TCGGTTGT SEQ ID NO: 131 | CAGTG TGTG | GGCCAGTGGTCTTGGTGTGCTGGCCTCGGACACGAATG GTCGGTGCTCGCAGGCTCGGCA SEQ ID NO: 380 |
| NGSPLEx 256_249 | TCGCGAAAT TCGGTTGT SEQ ID NO: 131 | CACAG ACTG | GCAGCTGGAGCATCTCCACCCTTGGTATTTCTGGTGTAA TGGTCGGTGCTCGCAGGCTCGGCA SEQ ID NO: 381 |
| NGSPLEx 256_250 | TCGCGAAAT TCGGTTGT SEQ ID NO: 131 | CTCTC AGTG | GTAGCTGGGGTGCTGGGGTTCATTCTCGGCACGGCTG CTGGTCGGTGCTCGCAGGCTCGGCA SEQ ID NO: 382 |
| NGSPLEx 256_251 | TCGCGAAAT TCGGTTGT SEQ ID NO: 131 | GTCAC AGTG | GCTGTAACCACACCGACGCGCGAGCTCTGCGCGGGCTT CACTGGTCGGTGCTCGCAGGCTCGGCA SEQ ID NO: 383 |
| NGSPLEx 256_252 | TCGCGAAAT TCGGTTGT SEQ ID NO: 131 | CTGTC AGAG | TCCAGGTCGATCTCCAAGGACTGGACTGTACGTCTCAGC TCTTGGTCGGTGCTCGCAGGCTCGGCA SEQ ID NO: 384 |
| NGSPLEx 256_253 | TCGCGAAAT TCGGTTGT SEQ ID NO: 131 | GACAG TGTG | TTAACCTACCACTGTTTTGTTTAGAGCGAACACAGTGTGG TCGGTGCTCGCAGGCTCGGCA SEQ ID NO: 385 |
| NGSPLEx 256_254 | TCGCGAAAT TCGGTTGT SEQ ID NO: 131 | GACAC ACTG | TCTCCTCCAGGGTGGCTGTCACTGCCTGGTACTTCCATG GTCGGTGCTCGCAGGCTCGGCA SEQ ID NO: 386 |
| NGSPLEx 256_255 | TCGCGAAAT TCGGTTGT SEQ ID NO: 131 | GAGTG ACTG | CACGACAGCAAATAGCACGGGTCAGATGCCCTTGGCTGA AAAGTGGTCGGTGCTCGCAGGCTCGGCA SEQ ID NO: 387 |
| NGSPLEx 256_256 | TCGCGAAAT TCGGTTGT SEQ ID NO: 131 | GTCAC TCAG | GGGACCAGCCGTCCTTATCAAAGTGCTCCCAGAAATTGG TCGGTGCTCGCAGGCTCGGCA SEQ ID NO: 388 |

TABLE 2-continued

List of 256 precursor for the 256plex of in FIG. 8

| Name | Region 1 | Region 2 |
|---|---|---|
| Capture Probe256 plex | CWSWSWSWS | ACAACCGAATTTCGCGAT TTTTTTTTTT\Biotin (SEQ ID NO: 389) |

TABLE 3

List of sequences used for proof of concept experiment FIG. 6

| Name | Region 3 | Region 4 | Region 5 |
|---|---|---|---|
| Precursor Oligo 1 | TAGCGCCTGCGGCCTGT SEQ ID NO: 390 | CTCTCTCTGU SEQ ID NO: 391 | TAGCGCCTGCGGCCTGTCTCTCTCTGUAAACGCATCGG TCGAATTATCTCCTGCTAGGCACTCGCTGTGCCCTGGA CTATCGTAA000ATGCTGTTT/36-FAM-3' SEQ ID NO: 392 |
| Precursor Oligo 2 | TAGCGCCTGCGGCCTGT SEQ ID NO: 390 | GTGTGACTGU SEQ ID NO: 393 | CTTGCGGAACACGAATCGACCACTGACACAATTCGTAAT CTCATTGCAAGCGTTT/36-FAM-3' SEQ ID NO: 394 |
| Precursor Oligo 3 | TAGCGCCTGCGGCCTGT SEQ ID NO: 390 | CAGAGACTGU SEQ ID NO: 395 | ATGCCCATTCAGCCTCACGTGGTGCTGATTTGGGGTGT TT/36-FAM-3/ SEQ ID NO: 396 |

| Name | Region 1 | Region 2 |
|---|---|---|
| Capture Probe256 plex | CAGWSWSWS | ACAGGCCGCAGGCGCTA/iBiodT/TTTTTTT/iBiodT/TTTTTTT/3B (SEQ ID NO: 397) |

TABLE 4

List of sequences used for FIG. 10

| Name/ Region | 6 | 7 | 8 |
|---|---|---|---|
| Precursor Oligo 4 | GTGGATGATCAACGC SEQ ID NO: 398 | A░░░░C | UCGCTTCCATACCGGGCGATGGACACAATTAAGAT CGCATTTAGAGTGAAGTATCAATCGGAAATCGTGC AGCGACC/36-FAM-3' SEQ ID NO: 399 |
| Precursor Oligo 5 | GTGGATGATCAACGC SEQ ID NO: 398 | A░░░░C | UCAATCAACCAGATTAGGACTCGGTTCCCGTGAGA AATAGAAGTCCGTATAAACGTTCAACGGGGTC/36-FAM-3' SEQ ID NO: 400 |
| Precursor Oligo 6 | GTGGATGATCAACGC SEQ ID NO: 398 | A░░░░C | UCGCTTCCATACCGGGCGATGGACACAATTAAGAT CGCATTTAGAGT/36-FAM-3' SEQ ID NO: 401 |

| Name/ Region | 1 | 4 | 2 |
|---|---|---|---|
| Capture Probe | GWSWSWST | GCGTTGATCATCCAC SEQ ID NO: 402 | ATAGACTCG/iBiodT/TTTTTTT/iBiodT/TTTTTTT/3B SEQ ID NO: 403 |

TABLE 4-continued

List of sequences used for FIG. 10

| Name/<br>RegionS | 5 | 3 |
|---|---|---|
| Pro-<br>tector | AGTCTAT | GTGGATGA<br>TCAACGC<br>SEQ ID NO:<br>398 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

XI. REFERENCES

The following references, to the extent that they provide exemplary procedural or other details supplementary to those set forth herein, are specifically incorporated herein by reference.

SantaLucia Jr, J., & Hicks, D. (2004). The thermodynamics of DNA structural motifs. Annu. Rev. Biophys. Biomol. Struct., 33, 415-440.

Wu, L. R., Wang, J. S., Fang, J. Z., Evans, E. R., Pinto, A., Pekker, I., & Zhang, D. Y. (2015). Continuously tunable nucleic acid hybridization probes. Nature methods, 12(12), 1191-1196.

Zhang, D. Y., Chen, S. X., & Yin, P. (2012). Optimizing the specificity of nucleic acid hybridization. Nature chemistry, 4(3), 208-214.

What is claimed:

1. A method for purifying one or more target nucleic acid molecules from a sample comprising a set of species of precursor oligonucleotide molecules, wherein each species of precursor oligonucleotide molecule comprises a fifth region comprising a target sequence, a fourth region comprising a sequence unique to the species of precursor oligonucleotide molecule in the set, wherein the fourth region is a barcode sequence of length n, wherein 2n is greater than or equal to the number of unique target sequences, and a third region that is conserved across all precursor oligonucleotide molecules in the set, the method comprising:
  (a) contacting the sample with a capture probe library at temperature and buffer conditions to allow for hybridization, wherein the capture probe library comprises a plurality of capture probe species, wherein each capture probe species comprises a first oligonucleotide comprising a first region and a second region, wherein the first region comprises a nucleotide sequence of n nucleotides in length, wherein each nucleotide in the nucleotide sequence of n nucleotides in length is selected from two or more nucleotides, wherein the first region is unique among the species of capture probes in the plurality, wherein the second region is conserved across all capture probe species, wherein the second region is complementary to the third region, and wherein the fourth region of each species of precursor molecule is complementary to the first region of a species of capture probe;
  (b) separating the plurality of species of precursor oligonucleotide molecules hybridized to the plurality of capture probes from the species of precursor oligonucleotides not hybridized to the plurality of capture probes;
  (c) treating the plurality of species of precursor oligonucleotide molecules hybridized to the plurality of capture probes with a cleavage agent sufficient to site-specifically cleave the plurality of species at a site to separate the fifth regions from at least a portion of the third and fourth regions; and
  (d) recovering the fifth regions from the plurality of capture probe species and at least a portion of the third and fourth regions, thereby producing one or more purified target nucleic acid molecule.

2. The method of claim 1, wherein the set of species of precursor oligonucleotide molecules is a set of precursor oligonucleotide molecules produced by the method comprising:
  (a1) calculating for each precursor oligonucleotide molecule a standard free energy of hybridization between the precursor oligonucleotide molecule and (i) a first oligonucleotide comprising a second region that is complementary to the third region of the precursor oligonucleotide molecule, and (ii) a first region that is complementary to the fourth region of the precursor oligonucleotide molecule;
  (a2) calculating a standard free energy of hybridization of folding for each precursor oligonucleotide molecule and for each first oligonucleotide;
  (b) calculating a standard free energy of a capture reaction as the standard free energy of hybridization between the precursor oligonucleotide molecule and the first oligonucleotide and the standard free energy of folding of the first oligonucleotide and the standard free energy of folding of the precursor oligonucleotide molecule;
  (c) rejecting the set of precursor oligonucleotide molecules if the difference between the lowest standard free energy of capture and a highest standard free energy of capture for the set of precursor nucleotide sequences exceeds 5 kcal/mol;
  (d) repeating steps (a) to (c) until a set of precursor oligonucleotide molecules meets the criterion; and
  (e) producing said set of precursor oligonucleotide molecules.

3. The method of claim 1, wherein each capture probe species further comprises a second oligonucleotide comprising a ninth region, wherein the ninth region is complementary to the second region.

4. The method of claim 3, wherein each first oligonucleotide further comprises a seventh region, wherein each second oligonucleotide further comprises an eighth region, and wherein the seventh region is complementary to the eighth region.

5. The method of claim 1, wherein each first oligonucleotide further comprises a chemical moiety, and wherein the separating the plurality of species of precursor molecules hybridized to the plurality of capture probe species comprises surface capture of the chemical moiety.

6. The method of claim 5, wherein the chemical moiety is selected from the group consisting of biotin, a thiol, an azide, an alkyne, a primary amine and a lipid.

7. The method of claim 1, wherein recovering the fifth regions from the plurality of capture probe species and the at least a portion of the third and fourth regions comprises a treatment selected from the group consisting of heating, introducing denaturants, washing with low salinity buffers, and introducing a nuclease.

8. The method of claim 1, wherein the site-specific cleavage comprises a treatment selected from the group consisting of changing the temperature, changing the pH, and illuminating the plurality of species of precursor molecules hybridized to the plurality of capture probe species at a specific wavelength.

9. The method of claim 1, wherein the standard free energies of binding between each first oligonucleotide and a DNA sequence complementary to the entire sequence of the first oligonucleotide are within 5 kcal/mol of each other.

10. The method of claim 1, wherein the two or more nucleotides at each nucleotide in the nucleotide sequence of n nucleotides in length are A or T.

11. The method of claim 1, wherein the two or more nucleotides at each nucleotide in the nucleotide sequence of n nucleotides in length are G or C.

12. The method of claim 1, wherein the two or more nucleotides at each nucleotide in the nucleotide sequence of n nucleotides in length are G or C for one or more nucleotides in the nucleotide sequence and A or T for one more nucleotides in the nucleotide sequence.

13. The method of claim 1, wherein the first region comprises between 3 and 25 nucleotides.

14. The method of claim 1, wherein n is between 3 and 60, 3 and 18, or 3 and 10 and not greater than the number of nucleotides in the first region.

15. The method of claim 1, wherein the first region further comprises at least one nucleotide in addition to the nucleotide sequence of n nucleotides in length.

16. The method of claim 1, wherein the second region comprises between 8 and 200 nucleotides.

17. The method of claim 3, wherein a concentration of the second oligonucleotide is greater than a sum of the concentrations of each first oligonucleotide of the capture probe library.

18. The method of claim 1, wherein the first region comprises an "S" degenerate nucleotide at one or more of the variable positions and/or a "W" degenerate nucleotide at one or more of the variable positions, but does not comprise an "N" degenerate nucleotide at any position, wherein the length of the first region is between 5 and 50 nucleotides, wherein the number of variable nucleotides is between 3 and 30, and wherein the length of the second region is between 5 and 50 nucleotides.

19. The method of claim 1, wherein the second nucleotide sequence comprises an "S" degenerate nucleotide at one or more position and/or a "W" degenerate nucleotide at one or more position, but does not comprise a "N" degenerate nucleotide at any position.

20. The method of claim 2, wherein the criterion is a maximum range of no more than 5 kcal/mol between a lowest standard free energy of capture and a highest standard free energy of capture for the set of precursor nucleotide sequences.

* * * * *

SEQUENCE LISTING

```
<160> NUMBER OF SEQ ID NOS: 421

<210> SEQ ID NO 1
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 1
taggtgcggt cgca                                                     14

<210> SEQ ID NO 2
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 2
tgtgactcac tg                                                       12

<210> SEQ ID NO 3
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 3
gcccgtcggc atgtattagc tctagaatta ccacagtgca acctttcgag tctcgtacgg    60
ttaagagcc                                                           69

<210> SEQ ID NO 4
<211> LENGTH: 12
<212> TYPE: DNA
```

```
<213> ORGANISM: Artificial sequence
<220> FEATURE:
<223> OTHER INFORMATION: Synthetic oligonucleotide

<400> SEQUENCE: 4
tgtctgtgtc tg                                                         12

<210> SEQ ID NO 5
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 5
ggggccggag aggggctgac cgggttggtt ttgatgcggt gctcgagtct cgtacggtta     60
agagcc                                                                66

<210> SEQ ID NO 6
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 6
tgtcacactc tg                                                         12

<210> SEQ ID NO 7
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 7
ccctgattcc ccgtcacccg tggtcaccat ggtagtggcc atagcagtct cgtacggtta     60
agagcc                                                                66

<210> SEQ ID NO 8
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 8
tgtgacactc tg                                                         12

<210> SEQ ID NO 9
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 9
tttttcgtca ctacctcccc gggtcgggag tgggtgaatt atgctgaacg agtctcgtac     60
ggttaagagc c                                                          71

<210> SEQ ID NO 10
<211> LENGTH: 12
<212> TYPE: DNA
<213> ORGANISM: Artificial sequence
```

```
<220> FEATURE:
<223> OTHER INFORMATION: Synthetic oligonucleotide

<400> SEQUENCE: 10
tgtgagagac tg                                                          12

<210> SEQ ID NO 11
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 11
gcccgcccgc tcccaagatc caactacgag cttttaggtc agtggagtct cgtacggtta     60
agagcc                                                                 66

<210> SEQ ID NO 12
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 12
tgtgtctgtc tg                                                          12

<210> SEQ ID NO 13
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 13
ggccgtccct cttaatcatg gcctcagttc cgaaacctac acattatctg agtctcgtac     60
ggttaagagc c                                                           71

<210> SEQ ID NO 14
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 14
tgtgagtcac tg                                                          12

<210> SEQ ID NO 15
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 15
ggtatctgat cgtcttcgaa cctccgactt tcgttctgga catgccagtc tcgtacggtt     60
aagagcc                                                                67

<210> SEQ ID NO 16
<211> LENGTH: 12
<212> TYPE: DNA
<213> ORGANISM: Artificial sequence
<220> FEATURE:
```

<223> OTHER INFORMATION: Synthetic oligonucleotide

<400> SEQUENCE: 16
tgtctcagac tg                                                         12

<210> SEQ ID NO 17
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 17
tggtggtgcc cttccgtcaa ttcctttaag tttcatgctt ctactcctag tctcgtacgg     60
ttaagagcc                                                             69

<210> SEQ ID NO 18
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 18
tgtcactcac tg                                                         12

<210> SEQ ID NO 19
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 19
cctgtccgtg tccgggccgg gtgaggtttc ccgtgcacta gggctgagtc tcgtacggtt     60
aagagcc                                                               67

<210> SEQ ID NO 20
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 20
tgtgactgtc tg                                                         12

<210> SEQ ID NO 21
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 21
gtaactagtt agcatgccag agtctcgttc gttatcggat ggcctagtat agtctcgtac     60
ggttaagagc c                                                          71

<210> SEQ ID NO 22
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 22
tgtcactctc tg                                                        12

<210> SEQ ID NO 23
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 23
gccccggaca tctaagggca tcacagacct gttattcctt gttgaagagt ctcgtacggt    60
taagagcc                                                             68

<210> SEQ ID NO 24
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 24
tgtctcagtc tg                                                        12

<210> SEQ ID NO 25
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 25
ggtagtagcg acgggcggtg tgtacaaagg gcaggtgagt atttgattca agtctcgtac    60
ggttaagagc c                                                         71

<210> SEQ ID NO 26
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 26
tgtctctgac tg                                                        12

<210> SEQ ID NO 27
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 27
ggcgctgggc tcttccctgt tcactcgccg ttactatgtt cggccttttt agtctcgtac    60
ggttaagagc c                                                         71

<210> SEQ ID NO 28
<211> LENGTH: 12
<212> TYPE: DNA
<213> ORGANISM: Artificial sequence
<220> FEATURE:
<223> OTHER INFORMATION: Synthetic oligonucleotide

```
<400> SEQUENCE: 28
tgtgtgtgac tg                                                    12

<210> SEQ ID NO 29
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 29
taccacccgc tttgggctgc attcccaagc aaccccccg aaagtctcgt acggttaaga    60
gcc                                                               63

<210> SEQ ID NO 30
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 30
tgtctgacac tg                                                    12

<210> SEQ ID NO 31
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 31
ctttccctta cggtacttgt tgactatcgg tctcgtaaac ggttagatcg agtctcgtac    60
ggttaagagc c                                                      71

<210> SEQ ID NO 32
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 32
tgtctctctc tg                                                    12

<210> SEQ ID NO 33
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 33
ggcggactgc gcggacccca cccgtttacc tcttaggtat ataacgccag tctcgtacgg    60
ttaagagcc                                                         69

<210> SEQ ID NO 34
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 34
```

```
tgtgactctc tg                                                           12

<210> SEQ ID NO 35
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 35
ggtggaaatg cgcccggcgg cggccggtcg ccggtacaca gttgagtctc gtacggttaa      60
gagcc                                                                  65

<210> SEQ ID NO 36
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 36
tgtgtgactc tg                                                           12

<210> SEQ ID NO 37
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 37
ccttccccgc cgggccttcc cagccgtccc ggagcaagat tgtttacaga agtctcgtac      60
ggttaagagc c                                                           71

<210> SEQ ID NO 38
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 38
tgtcagtgtc tg                                                           12

<210> SEQ ID NO 39
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 39
gggattcggc gagtgctgct gccggggggg ctgtaggaca acgtacaaca gtctcgtacg      60
gttaagagcc                                                             70

<210> SEQ ID NO 40
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 40
```
tgtgactgac tg                                                          12

<210> SEQ ID NO 41
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 41
gccgtgggag gggtggcccg gcccccccac gaggactact caagaattgc agtctcgtac     60
ggttaagagc c                                                          71

<210> SEQ ID NO 42
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 42
tgtgagactc tg                                                          12

<210> SEQ ID NO 43
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 43
gccgaccccg tgcgctcgct ccgccgtccc cctctgcacg cggacagtct cgtacggtta     60
agagcc                                                                66

<210> SEQ ID NO 44
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 44
tgtgagtgtc tg                                                          12

<210> SEQ ID NO 45
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 45
gtgttagact ccttggtccg tgtttcaaga cgggtggtca tttagcgagt ctcgtacggt     60
taagagcc                                                              68

<210> SEQ ID NO 46
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 46
tgtctgtcac tg                                                          12

```
<210> SEQ ID NO 47
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 47
ccaggcatag ttcaccatct ttcgggtcct aacacggagc ccattacagt ctcgtacggt    60
taagagcc                                                             68

<210> SEQ ID NO 48
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 48
tgtgtgagtc tg                                                        12

<210> SEQ ID NO 49
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 49
gggtgcgtcg ggtctgcgag agcgccagct atcctataag cgccgtccag tctcgtacgg    60
ttaagagcc                                                            69

<210> SEQ ID NO 50
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 50
tgtgtctcac tg                                                        12

<210> SEQ ID NO 51
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 51
gttcggttca tcccgcagcg ccagttctgc ttaccgtgcc acagtctcgt acggttaaga    60
gcc                                                                  63

<210> SEQ ID NO 52
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 52
tgtgtgagac tg                                                        12
```

<210> SEQ ID NO 53
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 53
ggattccgac ttccatggcc accgtcctgc tgtctgaaaa aatttctgca agtctcgtac    60
ggttaagagc c                                                         71

<210> SEQ ID NO 54
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 54
tgtcacagac tg                                                        12

<210> SEQ ID NO 55
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 55
acgctccagc gccatccatt ttcagggcta gttgacgcta tggcatcaag tctcgtacgg    60
ttaagagcc                                                            69

<210> SEQ ID NO 56
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 56
tgtgtctctc tg                                                        12

<210> SEQ ID NO 57
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 57
gcagcggccc tcctactcgt cgcggcgtag cgtcccattg agcagttgag tctcgtacgg    60
ttaagagcc                                                            69

<210> SEQ ID NO 58
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 58
tgtcagacac tg                                                        12

```
<210> SEQ ID NO 59
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 59
acccttctcc acttcggcct tcaaagttct cgtttctaga gcccagtctc gtacggttaa    60
gagcc                                                                65

<210> SEQ ID NO 60
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 60
tgtcacacac tg                                                        12

<210> SEQ ID NO 61
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 61
actctccccg gggctcccgc cggcttctcc gggatgtgat gggagtacca gtctcgtacg    60
gttaagagcc                                                           70

<210> SEQ ID NO 62
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 62
tgtcactgtc tg                                                        12

<210> SEQ ID NO 63
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 63
gccagaggct gttcaccttg gagacctgct gcggaccgct cacaaagtct cgtacggtta    60
agagcc                                                               66

<210> SEQ ID NO 64
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 64
tgtctgagac tg                                                        12

<210> SEQ ID NO 65
```

```
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 65
cccagccctt agagccaatc cttatcccga agttatcaat cagttgcagt ctcgtacggt    60
taagagcc                                                             68

<210> SEQ ID NO 66
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 66
tgtgtcagtc tg                                                        12

<210> SEQ ID NO 67
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 67
gctcccccgg ggaggggga ggacggggag cggggttgag agtctcgtac ggttaagagc     60
c                                                                    61

<210> SEQ ID NO 68
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 68
tgtgacagtc tg                                                        12

<210> SEQ ID NO 69
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 69 ccctgccgc cccgacccctt ctcccccgc cgccgtatct aaggtcccgt ctcgtacggt     60
taagagcc                                                             68

<210> SEQ ID NO 70
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 70
tgtctgagtc tg                                                        12

<210> SEQ ID NO 71
<211> LENGTH: 66
```

<212> TYPE: DNA
<213> ORGANISM: Artificial sequence
<220> FEATURE:
<223> OTHER INFORMATION: Synthetic oligonucleotide

<400> SEQUENCE: 71 ggcgggggg accggcccgc ggcccctccg ccgccgtcat gtccaagtct cgtacggtta    60
agagcc                                                              66

<210> SEQ ID NO 72
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 72
tgtgagagtc tg                                                       12

<210> SEQ ID NO 73
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 73
ggattcccct ggtccgcacc agttctaagt cggctaggga aggcaagtct cgtacggtta   60
agagcc                                                              66

<210> SEQ ID NO 74
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 74
tgtcagtctc tg                                                       12

<210> SEQ ID NO 75
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 75
ggctacctta agagagtcat agttactccc gccgtggccc ttcaccagtc tcgtacggtt   60
aagagcc                                                             67

<210> SEQ ID NO 76
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 76
tgtgagtgac tg                                                       12

<210> SEQ ID NO 77
<211> LENGTH: 65
<212> TYPE: DNA

```
<213> ORGANISM: Artificial sequence
<220> FEATURE:
<223> OTHER INFORMATION: Synthetic oligonucleotide

<400> SEQUENCE: 77
cacctctcat gtctcttcac cgtgccagac tagaggcgga tccgagtctc gtacggttaa    60
gagcc                                                                65

<210> SEQ ID NO 78
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 78
tgtctcacac tg                                                        12

<210> SEQ ID NO 79
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 79
gcccctcggg gctcgccccc ccgcctcacc gggtccggaa cgcagtctcg tacggttaag    60
agcc                                                                 64

<210> SEQ ID NO 80
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 80
tgtgtgacac tg                                                        12

<210> SEQ ID NO 81
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 81
gcccttctgc tccacgggag gtttctgtcc tccctagttt gccagaccag tctcgtacgg    60
ttaagagcc                                                            69

<210> SEQ ID NO 82
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 82
tgtctctgtc tg                                                        12

<210> SEQ ID NO 83
<211> LENGTH: 70
<212> TYPE: DNA
<213> ORGANISM: Artificial sequence
```

<220> FEATURE:
<223> OTHER INFORMATION: Synthetic oligonucleotide

<400> SEQUENCE: 83
gcttggccgc cacaagccag ttatccctgt ggtaatgatc tctctgagta gtctcgtacg    60
gttaagagcc                                                           70

<210> SEQ ID NO 84
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 84
tgtgtgtgtc tg                                                        12

<210> SEQ ID NO 85
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 85
gcggttcctc tcgtactgag caggattacc atggcggcca aatatagtct cgtacggtta    60
agagcc                                                               66

<210> SEQ ID NO 86
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 86
tgtctgtctc tg                                                        12

<210> SEQ ID NO 87
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 87
ccgaggctcc gcggcgctgc cgtatcgttc cgcctatgga ggaggacagt ctcgtacggt    60
taagagcc                                                             68

<210> SEQ ID NO 88
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 88
tgtgacacac tg                                                        12

<210> SEQ ID NO 89
<211> LENGTH: 66
<212> TYPE: DNA
<213> ORGANISM: Artificial sequence
<220> FEATURE:

<223> OTHER INFORMATION: Synthetic oligonucleotide

<400> SEQUENCE: 89
aggtcgtcta cgaatggttt agcgccaggt tccccagcct caggcagtct cgtacggtta    60
agagcc    66

<210> SEQ ID NO 90
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 90
tgtcactgac tg    12

<210> SEQ ID NO 91
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 91
catctttccc ttgcggtact atatctattg cgccagcctc ccctcagtct cgtacggtta    60
agagcc    66

<210> SEQ ID NO 92
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 92
tgtcagagtc tg    12

<210> SEQ ID NO 93
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 93
gacgggtgtg ctcttttagc tgttcttagg tagctagtat ctcgtcccca gtctcgtacg    60
gttaagagcc    70

<210> SEQ ID NO 94
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 94
tgtgtcacac tg    12

<210> SEQ ID NO 95
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 95
gcttttaggc ctactatggg tgttaaattt tttactctct ctacaagtcg agtctcgtac    60
ggttaagagc c    71

<210> SEQ ID NO 96
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 96
tgtctgtgac tg    12

<210> SEQ ID NO 97
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 97
agggtgatag attggtccaa ttgggtgtga ggagttcaac gtgtattgta agtctcgtac    60
ggttaagagc c    71

<210> SEQ ID NO 98
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 98
tgtgtcactc tg    12

<210> SEQ ID NO 99
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 99
gacttgttgg ttgattgtag atattgggct gttaattgtc agtttgttgt agtctcgtac    60
ggttaagagc c    71

<210> SEQ ID NO 100
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 100
tgtctgactc tg    12

<210> SEQ ID NO 101
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 101
gtaagatttg ccgagttcct tttactttt ttaacctttc cttatgccaa agtctcgtac    60
ggttaagagc c                                                        71

<210> SEQ ID NO 102
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 102
tgtcagagac tg                                                       12

<210> SEQ ID NO 103
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 103
gctgaaccct cgtggagcca ttcatacagg tccctgtcca ccggctagtc tcgtacggtt    60
aagagcc                                                             67

<210> SEQ ID NO 104
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 104
tgtcagtgac tg                                                       12

<210> SEQ ID NO 105
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 105
gctcggaggt tgggttctgc tccgaggtcg ccccacttgc atcctttgga gtctcgtacg    60
gttaagagcc                                                          70

<210> SEQ ID NO 106
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 106
tgtgtcagac tg                                                       12

<210> SEQ ID NO 107
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 107

```
ggattgcgct gttatccta gggtaacttg ttccgcagac gttgtgcagt ctcgtacggt    60
taagagcc                                                            68
```

<210> SEQ ID NO 108
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 108

```
tgtcagactc tg                                                       12
```

<210> SEQ ID NO 109
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 109

```
gccttatttc tcttgtcctt tcgtacaggg aggaatttga atatctgttt agtctcgtac    60
ggttaagagc c                                                        71
```

<210> SEQ ID NO 110
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 110

```
tgtcagtcac tg                                                       12
```

<210> SEQ ID NO 111
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 111

```
tttcccgtgg gggtgtggct aggctaagcg ttttgcattt catagacctt agtctcgtac    60
ggttaagagc c                                                        71
```

<210> SEQ ID NO 112
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 112

```
tgtctcactc tg                                                       12
```

<210> SEQ ID NO 113
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 113
caggtgagtt ttagctttat tggggagggg gtgatctact gcatcgttag agtctcgtac    60
ggttaagagc c    71

<210> SEQ ID NO 114
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 114
tgtgtctgac tg    12

<210> SEQ ID NO 115
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 115
ggctcgtagt gttctggcga gcagttttgt tgatttgagt ctaaggagta gtctcgtacg    60
gttaagagcc    70

<210> SEQ ID NO 116
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 116
tgtgtgtcac tg    12

<210> SEQ ID NO 117
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 117
gtacttgcgc ttactttgta gccttcatca gggtttgggg ttacctgcag tctcgtacgg    60
ttaagagcc    69

<210> SEQ ID NO 118
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 118
tgtgagtctc tg    12

<210> SEQ ID NO 119
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 119
gtgacgggcg gtgtgtacgc gcttcagggc cctgtacaat cctggtaaga agtctcgtac    60

```
ggttaagagc c                                                            71

<210> SEQ ID NO 120
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 120
tgtcacagtc tg                                                           12

<210> SEQ ID NO 121
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 121
tcttcatcga cgcacgagcc gagtgatcca ccgctgtttc ccttccaagt ctcgtacggt       60
taagagcc                                                                68

<210> SEQ ID NO 122
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 122
tgtgacagac tg                                                           12

<210> SEQ ID NO 123
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 123
gatcaatgtg tcctgcaatt cacattaatt ctcgcagcta gcgttcacaa agtctcgtac       60
ggttaagagc c                                                            71

<210> SEQ ID NO 124
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 124
tgtgtgtctc tg                                                           12

<210> SEQ ID NO 125
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 125
gctcagacag gcgtagcccc gggaggaacc cggggtcacg agtctcgtac ggttaagagc       60
```

```
c                                                              61

<210> SEQ ID NO 126
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 126
tgtctctcac tg                                                  12

<210> SEQ ID NO 127
<211> LENGTH: 71
<212> TYPE: DNA
<213> ORGANISM: Artificial sequence
<220> FEATURE:
<223> OTHER INFORMATION: Synthetic oligonucleotide

<400> SEQUENCE: 127
gcctacagca cccggtattc ccaggcggtc tcccaaggag catatataac agtctcgtac    60
ggttaagagc c                                                   71

<210> SEQ ID NO 128
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 128
tgtgagacac tg                                                  12

<210> SEQ ID NO 129
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 129
gagatcgggc gcgttcaggg tggtatggcc gtagagcgtt atccagtctc gtacggttaa    60
gagcc                                                          65

<210> SEQ ID NO 130
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 130
acatgcgacc gcacctattt tttttt                                   27

<210> SEQ ID NO 131
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 131
tcgcgaaatt cggttgt                                             17
```

```
<210> SEQ ID NO 132
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 132
tcgccgcgta aacgacgcgg cgcgcgtgct gccgcactgg tcggtgctcg caggctcggc    60
a                                                                    61

<210> SEQ ID NO 133
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 133
agcccgccgc gcacgcgccc ctgcgcccgc gccgcccag gtggtcggtg ctcgcaggct     60
cggca                                                                65

<210> SEQ ID NO 134
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 134
ctgctcccgg ctgggcccac cgccaaagca gcggccccac aggagctggt cggtgctcgc    60
aggctcggca                                                           70

<210> SEQ ID NO 135
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 135
ctcctccggc ccgcgcgcc cactccgcgc ccggcctggc cgctggtcgg tgctcgcagg     60
ctcggca                                                              67

<210> SEQ ID NO 136
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 136
gccgccgccg ccgccgccgc cgccgccccg ctgccttctc agcctggtcg gtgctcgcag    60
gctcggca                                                             68

<210> SEQ ID NO 137
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 137
```

```
gcgggtgggc ggcccgcgtt ccttagccgc ggctccgcgg ctggtcggtg ctcgcaggct    60
cggca                                                                65
```

<210> SEQ ID NO 138
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 138

```
ccattcctgc cagacccccg gctatcccgg tggccaggct ggtcggtgct cgcaggctcg    60
gca                                                                  63
```

<210> SEQ ID NO 139
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 139

```
ggcctcgcgt gcctggacag ccccgcgggc cagcaagcct atggtcggtg ctcgcaggct    60
cggca                                                                65
```

<210> SEQ ID NO 140
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 140

```
ccatctcagg gtgaggggct tcggcagccc ctcatgctgt ggtcggtgct cgcaggctcg    60
gca                                                                  63
```

<210> SEQ ID NO 141
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 141

```
gcgaccaaag gccggcgcac ggcctggccg ctcagcgact cccggctggt cggtgctcgc    60
aggctcggca                                                           70
```

<210> SEQ ID NO 142
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 142

```
cgcggcctca aaaggcctcc taggccgcgg cgggcaaagc actggtcggt gctcgcaggc    60
tcggca                                                               66
```

<210> SEQ ID NO 143
<211> LENGTH: 66
<212> TYPE: DNA
<213> ORGANISM: Artificial sequence

```
<220> FEATURE:
<223> OTHER INFORMATION: Synthetic oligonucleotide

<400> SEQUENCE: 143
tacgctctcg cgcaccaggt acgcctggtg tttctttgtg gttggtcggt gctcgcaggc    60
tcggca                                                               66

<210> SEQ ID NO 144
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 144
ctctgcccaa tcccggctcc gggcgacccg ggccctggt cggtgctcgc aggctcggca    60

<210> SEQ ID NO 145
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 145
tcttgtagga ggcccattcc tcccaccacg gggccaccca ccccgtggtc ggtgctcgca    60
ggctcggca                                                            69

<210> SEQ ID NO 146
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 146
cagcccccaa acccgactgg tcgaagggg acatcaagtc ccctggtcg gtgctcgcag     60 gctcggca                                                             68

<210> SEQ ID NO 147
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 147
cgcagccgac gccggcgcga gagcaggggc ggggccggcg cggtggtcgg tgctcgcagg    60
ctcggca                                                              67

<210> SEQ ID NO 148
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 148
ggcccgctcg gcaggcccca actggccctc cccttggcg gcgatggtcg gtgctcgcag    60
gctcggca                                                             68

<210> SEQ ID NO 149
```

```
<210> SEQ ID NO 149
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 149
cgggccgaat gccagcccgc cgagctcagg gcagcgggga gctggttggt cggtgctcgc    60
aggctcggca                                                          70

<210> SEQ ID NO 150
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 150
acctccgctg cgtctctccg cgccgccgcc gctgctcgcc gttggtcggt gctcgcaggc    60
tcggca                                                              66

<210> SEQ ID NO 151
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 151
cggcccaggt ctcggtcagg gccagggccg ccgagagcag caggatggtc ggtgctcgca    60
ggctcggca                                                           69

<210> SEQ ID NO 152
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 152
ctgcctcacg catcacagca cccccacccg agcgcgggcg ggtggtcggt gctcgcaggc    60
tcggca                                                              66

<210> SEQ ID NO 153
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 153
ggccacgctg ccaccagcag caggcccatg gggtggcagg gtggtcggtg ctcgcaggct    60
cggca                                                               65

<210> SEQ ID NO 154
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 154
ccaggggtag cccccctggat tatggtctga ctcaggactg gtcggtgctc gcaggctcgg    60
``` ca                                                                62

<210> SEQ ID NO 155
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 155
cgaagttgcc cagggtggca gtgcagcccc gggctgagtg gtcggtgctc gcaggctcgg    60
ca                                                                62

<210> SEQ ID NO 156
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 156
gttacctccc cgcacacgga ctgtgtggat gcggcggggt ggtcggtgct cgcaggctcg    60
gca                                                               63

<210> SEQ ID NO 157
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 157
agagctcatg tatgggttaa tccgaccatg agctctgtgg tcggtgctcg caggctcggc    60
a                                                                 61

<210> SEQ ID NO 158
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 158
ggccgggcca cggccagcat ccggacccgg ggcagcggcg tggtcggtgc tcgcaggctc    60
ggca                                                              64

<210> SEQ ID NO 159
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 159
gccattacgg cttccccggc caatagacgc ccggctgccc ttacatggtc ggtgctcgca    60
ggctcggca                                                         69

<210> SEQ ID NO 160
<211> LENGTH: 69
<212> TYPE: DNA
<213> ORGANISM: Artificial sequence
<220> FEATURE:

<223> OTHER INFORMATION: Synthetic oligonucleotide

<400> SEQUENCE: 160
ttcagcattt ctgctgaaat ctagggtgga aatgcgttcc tagtgtggtc ggtgctcgca    60
ggctcggca    69

<210> SEQ ID NO 161
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 161
ctcagcggaa atccggcgat ctggccggaa gtgcggcaca ctctggtcgg tgctcgcagg    60
ctcggca    67

<210> SEQ ID NO 162
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 162
tggcaggaag ctgcagcctt tctcaagagc agccaggatc tcctgctggt cggtgctcgc    60
aggctcggca    70

<210> SEQ ID NO 163
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 163
ggtagcgagg agagcggctg aggctcagtg cgcctgcgcg gcgctggtcg gtgctcgcag    60
gctcggca    68

<210> SEQ ID NO 164
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 164
gccatggcag ctttcatggc gtctggggtt ttaccccact catctttggt cggtgctcgc    60
aggctcggca    70

<210> SEQ ID NO 165
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 165
tgcatcttca ggagacgctc gtagccctcg cgcttctcct tggtcggtgc tcgcaggctc    60
ggca    64

```
<210> SEQ ID NO 166
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 166
ccgttggcca cttgtggcca ttcctactcc catgccggct ggtcggtgct cgcaggctcg    60
gca                                                                 63

<210> SEQ ID NO 167
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 167
aactgggtcc tacggcttgg actttccaac cctgacagac ccgcatggtc ggtgctcgca    60
ggctcggca                                                           69

<210> SEQ ID NO 168
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 168
gccgctgctg cagcagctgc cttatccacc cggagcttgt ggtcggtgct cgcaggctcg    60
gca                                                                 63

<210> SEQ ID NO 169
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 169
acgcggcctc tcccggcccc ttccgtttag taggagccgc actggtcggt gctcgcaggc    60
tcggca                                                              66

<210> SEQ ID NO 170
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 170 tgagggctt gggcagaccc tcatgctgca catggcaggt gtattggtcg gtgctcgcag     60
gctcggca                                                            68

<210> SEQ ID NO 171
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 171
```

```
cccggcccaa caaactacct acgtccggga gtcgccaacc gacgtggtcg gtgctcgcag      60
gctcggca                                                              68

<210> SEQ ID NO 172
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 172
aggcagactg ctgcaggacg ggactgggcc gggaaccggc tggtcggtgc tcgcaggctc      60
ggca                                                                  64

<210> SEQ ID NO 173
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 173
tctaaaccgt ttatttctcc ccaccagaag gttggggtgg tcggtgctcg caggctcggc      60
a                                                                     61

<210> SEQ ID NO 174
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 174
aacactgcct tcttggcctt taaagccttc gctttggctt catggtcggt gctcgcaggc      60
tcggca                                                                66

<210> SEQ ID NO 175
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 175
cggtagccga aggagttcaa aagacctcta gtgcgcccac cgcatggtcg gtgctcgcag      60
gctcggca                                                              68

<210> SEQ ID NO 176
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 176
ggtgacaggg tggcccagga gcggccactg agatgagacc ttggtcggtg ctcgcaggct      60
cggca                                                                 65

<210> SEQ ID NO 177
<211> LENGTH: 63
<212> TYPE: DNA
<213> ORGANISM: Artificial sequence
```

<220> FEATURE:
<223> OTHER INFORMATION: Synthetic oligonucleotide

<400> SEQUENCE: 177
gatcactccc caggcgctga ggacgatgcc gcaggcggct ggtcggtgct cgcaggctcg    60
gca                                                                  63

<210> SEQ ID NO 178
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 178
cttaagacca gtcagtggtt gctcctaccc attcagtggc ctgagctggt cggtgctcgc    60
aggctcggca                                                           70

<210> SEQ ID NO 179
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 179
gaagctccta gaagcttcac aagttggggc acaactcctg ttggtcggtg ctcgcaggct    60
cggca                                                                65

<210> SEQ ID NO 180
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 180
tggcgcgcgg cactgggagc cgccgggccg agcctgtcaa tggtcggtgc tcgcaggctc    60
ggca                                                                 64

<210> SEQ ID NO 181
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 181
tcatagaaag agagggaagt tttggcgatc acaacagcgc caaatggtcg gtgctcgcag    60
gctcggca                                                             68

<210> SEQ ID NO 182
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 182
caaagaatgc aaacatcatg tttgagccct ggggatcagg gtggtcggtg ctcgcaggct    60
cggca                                                                65

```
<210> SEQ ID NO 183
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 183
gatagcgctc ctgtctattg gctgcgccat cgcccgtcag actggtcggt gctcgcaggc    60
tcggca                                                              66

<210> SEQ ID NO 184
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 184
catatgcagg tcccctgttg gccattccaa tgggtggcgg tggctggtcg gtgctcgcag    60
gctcggca                                                            68

<210> SEQ ID NO 185
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 185
actccctgct ccttgggaat acggaccacg cagtctataa tgccttggtc ggtgctcgca    60
ggctcggca                                                           69

<210> SEQ ID NO 186
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 186
cggggtaacc gtggagggcg acgcgcagag gctgcggcta tttatggtcg gtgctcgcag    60
gctcggca                                                            68

<210> SEQ ID NO 187
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 187
ggactggtcc catgaggcag aaggagcacc agcgcctgct gggtggtggt cggtgctcgc    60
aggctcggca                                                          70

<210> SEQ ID NO 188
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 188
```

```
cgagaaacag cgcccgacac ctggcccttc gcagctctcg ccttggtcgg tgctcgcagg    60
ctcggca                                                              67

<210> SEQ ID NO 189
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 189
ctgcatggcc ttcatgacat gaaggttggg cacattcttg tctggtcggt gctcgcaggc    60
tcggca                                                               66

<210> SEQ ID NO 190
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 190
ccgaaaccca tggtgtcggc tgtatccgag agctggggag cagctggtcg gtgctcgcag    60
gctcggca                                                             68

<210> SEQ ID NO 191
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 191
ttcatgcaga tcacctgcac cccgcttgtg ttcagtgggg ttggtcggtg ctcgcaggct    60
cggca                                                                65

<210> SEQ ID NO 192
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 192
agctgccggg gtccggttcc tcagctccag gtggatcctt ggtcggtgct cgcaggctcg    60
gca                                                                  63

<210> SEQ ID NO 193
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 193
ctcggaagta gccccgtag gtgccctgct tgtggtcaaa ctggtcggtg ctcgcaggct    60
cggca                                                                65

<210> SEQ ID NO 194
<211> LENGTH: 63
<212> TYPE: DNA
```

```
<213> ORGANISM: Artificial sequence
<220> FEATURE:
<223> OTHER INFORMATION: Synthetic oligonucleotide

<400> SEQUENCE: 194
cgggggtagc ggtcaattcc agccaccaga gcatggctgt ggtcggtgct cgcaggctcg    60
gca                                                                  63

<210> SEQ ID NO 195
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 195
gaaacatgat cgcttataag ccagcggtcc caattcggtc caccgtggtc ggtgctcgca    60
ggctcggca                                                            69

<210> SEQ ID NO 196
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 196
cccacacgtc catgactggt cgtcctagat tttaggtgtc tggtcggtgc tcgcaggctc    60
ggca                                                                 64

<210> SEQ ID NO 197
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 197
ctttagctcg agattgtccc tctctgtcca gcagataggt ggtcggtgct cgcaggctcg    60
gca                                                                  63

<210> SEQ ID NO 198
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 198
gccgtcctgc gcaagcgctt ttcaacccca ctcctttctt ggtcggtgct cgcaggctcg    60
gca                                                                  63

<210> SEQ ID NO 199
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 199
cagtctctgg gagaatgggc agttcccaat cttggcccct ggtcggtgct cgcaggctcg    60
gca                                                                  63
```

<210> SEQ ID NO 200
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 200
ggttggtgct tgccacactt cttacagaaa gtccggcggg ttttggtcgg tgctcgcagg    60
ctcggca                                                              67

<210> SEQ ID NO 201
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 201
catgtagttg aggtcaatga aggggtcatt gatggcaaca atattggtcg gtgctcgcag    60
gctcggca                                                             68

<210> SEQ ID NO 202
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 202
cggaactgga ggtttccttt tccgccatag tttgtcctgg tcggtgctcg caggctcggc    60
a                                                                    61

<210> SEQ ID NO 203
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 203
ttgtagtctg agagagtgcg gccatcctcc agctgtttgc cggtggtcgg tgctcgcagg    60
ctcggca                                                              67

<210> SEQ ID NO 204
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 204
ctgcagtggc tttaaaccca cagtagtaac ctgcaggatc acacttggtc ggtgctcgca    60
ggctcggca                                                            69

<210> SEQ ID NO 205
<211> LENGTH: 69
<212> TYPE: DNA
<213> ORGANISM: Artificial sequence
<220> FEATURE:
<223> OTHER INFORMATION: Synthetic oligonucleotide

```
<400> SEQUENCE: 205
cgaaggacag gtggtctctt cgttgggacg tcccctttgc cagcatggtc ggtgctcgca    60
ggctcggca                                                            69

<210> SEQ ID NO 206
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 206
agcttggctc ccttcttgcg gcccaggggc agcgcatggt cggtgctcgc aggctcggca    60

<210> SEQ ID NO 207
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 207
ttccgacatg tccgcatttt tgatcacggc ctttcggtgg tcggtgctcg caggctcggc    60
a                                                                     61

<210> SEQ ID NO 208
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 208
cttgggaaga ccaagtcctc aaggatggca tcgtgcacag ctgtggtcgg tgctcgcagg    60
ctcggca                                                               67

<210> SEQ ID NO 209
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 209
cggccgcctc caggaacgcc gaccactcca ctttaggtat catggtcggt gctcgcaggc    60
tcggca                                                                66

<210> SEQ ID NO 210
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 210
aggcgaagtt ccgtctacgg ctatttaatg gagcgcctgg tcggtgctcg caggctcggc    60
a                                                                     61

<210> SEQ ID NO 211
<211> LENGTH: 66
<212> TYPE: DNA
<213> ORGANISM: Artificial sequence
```

<220> FEATURE:
<223> OTHER INFORMATION: Synthetic oligonucleotide

<400> SEQUENCE: 211
tgtatgttcc atccatgtga gcagcaaatg tgtatttccc actggtcggt gctcgcaggc    60
tcggca    66

<210> SEQ ID NO 212
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 212
ggtctcatcc gaaccctgcg gatatatttt tcacccaaga aatttggtcg gtgctcgcag    60
gctcggca    68

<210> SEQ ID NO 213
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 213
ggccttcacg cggcccagga gtttcttatt gttgcggcag ttggtcggtg ctcgcaggct    60
cggca    65

<210> SEQ ID NO 214
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 214
ccttttccaa ggattttacg ttgcggcttg ttagggtgat ttggtcggtg ctcgcaggct    60
cggca    65

<210> SEQ ID NO 215
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 215
actgttctct cttggcaaag taatcaggat acattgcctg gtcggtgctc gcaggctcgg    60
ca    62

<210> SEQ ID NO 216
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 216
acagtagcat gcagtcccac aacttgtacc agcatcccca gcgtcttggt cggtgctcgc    60
aggctcggca    70

<210> SEQ ID NO 217
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 217
acttggctcc agcatgttgt caccattcca accagaaatt ggcatggtcg gtgctcgcag    60
gctcggca    68

<210> SEQ ID NO 218
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 218
acaatgcaaa gatggctttt cagagcagcc agtggggtg gtcggtgctc gcaggctcgg    60
ca    62

<210> SEQ ID NO 219
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 219
cgacgtagcc cggcctcttc gacctgcacc tccgcggctc cctctgtggt cggtgctcgc    60
aggctcggca    70

<210> SEQ ID NO 220
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 220
agtggaaaca ggattactat gatacaaaac ttccactact ggtcggtgct cgcaggctcg    60
gca    63

<210> SEQ ID NO 221
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 221
gcaaaggcaa tcttcaaata gaagctggca acacaagacc tggtcggtgc tcgcaggctc    60
ggca    64

<210> SEQ ID NO 222
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 222
aatcacgcac tgtccccaac agccccagtt aacacagggt ggtcggtgct cgcaggctcg    60
gca                                                                 63

<210> SEQ ID NO 223
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 223
cagggtttct ggtccaaata ggcttggtct tgtttatggt cggtgctcgc aggctcggca    60

<210> SEQ ID NO 224
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 224
cccgaatccg ccggcccttc tcaccaagaa cattctgttg gtcggtgctc gcaggctcgg    60
ca                                                                  62

<210> SEQ ID NO 225
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 225
ggagatccat catctctccc ttcaatttgt cttcgatgac attggtcggt gctcgcaggc    60
tcggca                                                              66

<210> SEQ ID NO 226
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 226
tggcattagc agtaggttct tgtatttgag tctgcttggt cggtgctcgc aggctcggca    60

<210> SEQ ID NO 227
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 227
gaaaactggt cagatgaata ttattgcttc ccattttcaa ccagttggtc ggtgctcgca    60
ggctcggca                                                           69

<210> SEQ ID NO 228
<211> LENGTH: 61
<212> TYPE: DNA
<213> ORGANISM: Artificial sequence
<220> FEATURE:
<223> OTHER INFORMATION: Synthetic oligonucleotide

```
<400> SEQUENCE: 228
tccagagggt ccggatcgct ctcttctgca ctgaggttgg tcggtgctcg caggctcggc    60
a                                                                    61

<210> SEQ ID NO 229
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 229
ccatcctggc aggcggctgt ggtggttttga agagtttgga ctggtcggtg ctcgcaggct    60
cggca                                                                65

<210> SEQ ID NO 230
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 230
gctggcaagg ctgagcaatt catgtttatc tgcaacagct ggtcggtgct cgcaggctcg    60
gca                                                                  63

<210> SEQ ID NO 231
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 231
agcatcagct actgccagcg gttcatgggc ttcttttact atggtcggtg ctcgcaggct    60
cggca                                                                65

<210> SEQ ID NO 232
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 232
tgagtgagcc ctcctgccac gtctccacgg tcaccacctc ctctggtcgg tgctcgcagg    60
ctcggca                                                              67

<210> SEQ ID NO 233
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 233
ctttgggtcc caaggtgctc tttaccaagt ctccaatggc gattggtcgg tgctcgcagg    60
ctcggca                                                              67

<210> SEQ ID NO 234
<211> LENGTH: 70
```

```
<212> TYPE: DNA
<213> ORGANISM: Artificial sequence
<220> FEATURE:
<223> OTHER INFORMATION: Synthetic oligonucleotide

<400> SEQUENCE: 234
aacccaatta gttcccagaa gtcacaactc agctcatggc cacctgtggt cggtgctcgc      60
aggctcggca                                                            70

<210> SEQ ID NO 235
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 235
ctccttggtt ccatctcccg tggcatcgct tccctctcgg tggtcggtgc tcgcaggctc      60
ggca                                                                  64

<210> SEQ ID NO 236
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 236
tatttcacca ggccggcaaa gaatggacgg tccttcaggt caacgtggtc ggtgctcgca      60
ggctcggca                                                             69

<210> SEQ ID NO 237
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 237
ccctcagagg acagggcgcg gttgctgggt catgagcacc tggtcggtgc tcgcaggctc      60
ggca                                                                  64

<210> SEQ ID NO 238
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 238
caggcaccag accaaagacc tcctgcccca cagcaaatgg tcggtgctcg caggctcggc      60
a                                                                     61

<210> SEQ ID NO 239
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 239
agtttcctct tcactcagca gcatgttggg gatcccgcgg tggtcggtgc tcgcaggctc      60
```

```
ggca                                                                 64

<210> SEQ ID NO 240
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 240
tctgtgagaa aaccttggag aatcaataat ggtggattca ttgattggtc ggtgctcgca    60
ggctcggca                                                            69

<210> SEQ ID NO 241
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 241
gctgtatctg gtcctggcgg ccggctgtga tgtttgacat tgtccatggt cggtgctcgc    60
aggctcggca                                                           70

<210> SEQ ID NO 242
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 242
gatggcggcg gggggcaggg ggcgcacgta gcctggccat ggtcggtgct cgcaggctcg    60
gca                                                                  63

<210> SEQ ID NO 243
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 243
ctctctcttc agcaatggtg aggcggatac cctttcctcg ggtggtcggt gctcgcaggc    60
tcggca                                                               66

<210> SEQ ID NO 244
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 244
tctgggacaa gacagtcgag ggagcttctt cctcagggaa cttggtcggt gctcgcaggc    60
tcggca                                                               66

<210> SEQ ID NO 245
<211> LENGTH: 63
<212> TYPE: DNA
<213> ORGANISM: Artificial sequence
<220> FEATURE:
<223> OTHER INFORMATION: Synthetic oligonucleotide
```

<400> SEQUENCE: 245
gctgccaaag ctgggtccat gacaacttct ggtggggcgt ggtcggtgct cgcaggctcg    60
gca    63

<210> SEQ ID NO 246
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 246
agactgccag cgaagcccct cttatgagca aaagagcaac cctggtcggt gctcgcaggc    60
tcggca    66

<210> SEQ ID NO 247
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 247
cttcaggtgt ccttgaagca ataatttctg tcagtacttt ttcatttggt cggtgctcgc    60
aggctcggca    70

<210> SEQ ID NO 248
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 248
aacgatcaaa attagacatg tcttcatctg aatcatcttc ccagtggtcg gtgctcgcag    60
gctcggca    68

<210> SEQ ID NO 249
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 249
cggccacacc atctttgtca gcagtcacat tgcccaagtc tccaactggt cggtgctcgc    60
aggctcggca    70

<210> SEQ ID NO 250
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 250
tgacctctca ctttttccagc acgggccagg gaaccatgga cttttggtcg gtgctcgcag    60
gctcggca    68

<210> SEQ ID NO 251

```
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 251
cactctgaac gcat                                                          14

<210> SEQ ID NO 252
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 252
gtcagcataa tctttatttc aaaataacat ttttattatg gtcggtgctc gcaggctcgg         60
ca                                                                       62

<210> SEQ ID NO 253
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 253
agccacagga tgttctcgtc acactttttcc atgtaggcgt tattggtcgg tgctcgcagg        60
ctcggca                                                                  67

<210> SEQ ID NO 254
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 254
tatccgttcc ttacattgaa ccattttact gttcccaaaa ccttcgtggt cggtgctcgc        60
aggctcggca                                                               70

<210> SEQ ID NO 255
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 255 gactttaca atcgattccc caaaccccctt tatggcagca acactgtggt cggtgctcgc         60
aggctcggca                                                               70

<210> SEQ ID NO 256
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 256
ttcttgtaat ttgcataatc ctcaagaatg gaatccactg gtcggtgctc gcaggctcgg         60
ca                                                                       62
```

<210> SEQ ID NO 257
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 257
tggtcccagg ggaaaggaag aggccagttg gtccagtttt gattggtcgg tgctcgcagg    60
ctcggca                                                             67

<210> SEQ ID NO 258
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 258
caggggacgg tactccacat cctctctgag caggcggtgg tcggtgctcg caggctcggc    60
a                                                                   61

<210> SEQ ID NO 259
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 259
cttctacatc atcagctgcc atacgaagaa gggactccgt tggtcggtgc tcgcaggctc    60
ggca                                                                64

<210> SEQ ID NO 260
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 260
gccaccagca tcaaccttct tggcttcggg tttcttctgg tcggtgctcg caggctcggc    60
a                                                                   61

<210> SEQ ID NO 261
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 261
ccccaccggt gctcttggta cgaagatcca tgctaaattc cccatggtcg gtgctcgcag    60
gctcggca                                                            68

<210> SEQ ID NO 262
<211> LENGTH: 70
<212> TYPE: DNA
<213> ORGANISM: Artificial sequence
<220> FEATURE:
<223> OTHER INFORMATION: Synthetic oligonucleotide -continued

<400> SEQUENCE: 262
ttgtatataa gattacttta ttcctgcatc ttctcaatgg tttctttggt cggtgctcgc    60
aggctcggca                                                          70

<210> SEQ ID NO 263
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 263
cattttcatg gttttgtaga gcttcaattt tgtctaagcc tccatggtcg gtgctcgcag    60
gctcggca                                                            68

<210> SEQ ID NO 264
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 264
catagttgtc aacaagcaca gtgaaagcgc cattctcttt acatggtcgg tgctcgcagg    60
ctcggca                                                             67

<210> SEQ ID NO 265
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 265
gccaacagca tgctgggtaa cattgtagac tcttcctggt cggtgctcgc aggctcggca    60

<210> SEQ ID NO 266
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 266
aggagatctc cacaggggct ggacggttca ttatggcaaa ttggtcggtg ctcgcaggct    60
cggca                                                               65

<210> SEQ ID NO 267
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 267
ttgagcatct cgtagttggg aggctggccg ctgttgacag gagagtggtc ggtgctcgca    60
ggctcggca                                                           69

<210> SEQ ID NO 268
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 268 ctcccttcc ccagtagttt cggtttctca acagtttcct tggtcggtgc tcgcaggctc    60
ggca    64

<210> SEQ ID NO 269
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 269
tggtttttaa caggtttaac caatcatcta ctatctgatt ggtcggtgct cgcaggctcg    60
gca    63

<210> SEQ ID NO 270
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 270
ccttctgtcc tcatgttggc agagatatct actctgtggt cggtgctcgc aggctcggca    60

<210> SEQ ID NO 271
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 271
ggattccagt agccaggttg gtacgggacg gcatcataac atggtcggtg ctcgcaggct    60
cggca    65

<210> SEQ ID NO 272
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 272
cttcagcgga ggcatttcca ccaatgagcg agtcattggt cggtgctcgc aggctcggca    60

<210> SEQ ID NO 273
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 273
gtttatggta aagcttagcc ttcagaccaa tcattttctt tgctggtcgg tgctcgcagg    60
ctcggca    67

<210> SEQ ID NO 274
<211> LENGTH: 65
<212> TYPE: DNA

<213> ORGANISM: Artificial sequence
<220> FEATURE:
<223> OTHER INFORMATION: Synthetic oligonucleotide

<400> SEQUENCE: 274

```
ggccgcaaaa gggaagagaa ctacacgctg cttccggttc ttggtcggtg ctcgcaggct    60
cggca                                                                65
```

<210> SEQ ID NO 275
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 275

```
ttgttcactg ggtctttgtc tttcttggcc gactttccag cgtctggtcg gtgctcgcag    60
gctcggca                                                             68
```

<210> SEQ ID NO 276
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 276

```
cttcccagtt aaggctcttt attttatttt gaacactttt ttgcattggt cggtgctcgc    60
aggctcggca                                                           70
```

<210> SEQ ID NO 277
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 277

```
atcaacaagc cacggtttta gctcttcagg aatctttact ttaactggtc ggtgctcgca    60
ggctcggca                                                            69
```

<210> SEQ ID NO 278
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 278

```
ggtggttcct tgagggcttt gatgatcagg gcagaggcag aaggctggtc ggtgctcgca    60
ggctcggca                                                            69
```

<210> SEQ ID NO 279
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 279

```
aattcacaca cctcacagta aacatcagac tttgctggga cctctggtcg gtgctcgcag    60
gctcggca                                                             68
```

<210> SEQ ID NO 280
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 280
tgtcatcctt cttgccacct ccaggaccat gaccaccact ctgactggtc ggtgctcgca    60
ggctcggca                                                            69

<210> SEQ ID NO 281
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 281
gagcaaggag ggctggaagc tgttagtcag agtgttgaag ctggtcggtg ctcgcaggct    60
cggca                                                                65

<210> SEQ ID NO 282
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 282
aaaattgtgc ggatgtggct tctggaagac cttcattcta aagctggtcg gtgctcgcag    60
gctcggca                                                             68

<210> SEQ ID NO 283
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 283
gcagttttct aattgagaat gtaatcttgg tctttaaaga acatggtcgg tgctcgcagg    60
ctcggca                                                              67

<210> SEQ ID NO 284
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 284
gtttctgcat cagcccgctc atcaaatcca gggaagttgg tcggtgctcg caggctcggc    60
a                                                                    61

<210> SEQ ID NO 285
<211> LENGTH: 63
<212> TYPE: DNA
<213> ORGANISM: Artificial sequence
<220> FEATURE:
<223> OTHER INFORMATION: Synthetic oligonucleotide

```
<400> SEQUENCE: 285
ccagcggcaa cctcagccaa gtaacggtag taatctcctt ggtcggtgct cgcaggctcg    60
gca                                                                 63

<210> SEQ ID NO 286
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 286
gtgatcgggg tttcttgata ccatttctgt gccattttcg ggtggtcggt gctcgcaggc    60
tcggca                                                              66

<210> SEQ ID NO 287
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 287
aggaggtcct gctgagttgg tgaatctctg gtaacggtgg tggtcggtgc tcgcaggctc    60
ggca                                                                64

<210> SEQ ID NO 288
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 288
cctggttttc taaaattctt caggtcaata gtcaagcctt tggtcggtgc tcgcaggctc    60
ggca                                                                64

<210> SEQ ID NO 289
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 289
acaatatcac ctttcttata gattcgcata tatgtggcca aaggatggtc ggtgctcgca    60
ggctcggca                                                           69

<210> SEQ ID NO 290
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 290
aaacaaaaca agaaaaagta atctgctaaa aactataggg tccctggtc ggtgctcgca     60 ggctcggca                                                           69

<210> SEQ ID NO 291
<211> LENGTH: 65
```

```
<212> TYPE: DNA
<213> ORGANISM: Artificial sequence
<220> FEATURE:
<223> OTHER INFORMATION: Synthetic oligonucleotide

<400> SEQUENCE: 291
tagaatcttt tttattcaga aaaaaaaac cccaaaaaac atggtcggtg ctcgcaggct    60
cggca                                                              65

<210> SEQ ID NO 292
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 292
agtttaataa atacaaatac tcgtttcttt ttgattagtg tggtcggtgc tcgcaggctc    60
ggca                                                                64

<210> SEQ ID NO 293
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 293
actttgagat tcttttcttt tgcgcctctt atcaagtcag ctggtcggtg ctcgcaggct    60
cggca                                                               65

<210> SEQ ID NO 294
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 294
agcctggttg gaggattcct agtttttatac atgagaaata gtggtcggtg ctcgcaggct   60
cggca                                                               65

<210> SEQ ID NO 295
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 295
gttcccaaga tagaagagta ggtatgaagc aattctgact ctggtcggtg ctcgcaggct    60
cggca                                                               65

<210> SEQ ID NO 296
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 296
tctttgtatg agtcttcatt cagtgtatca agttcatggt cggtgctcgc aggctcggca    60
```

<210> SEQ ID NO 297
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 297
acagatgaat gtaggattga tgcaagtcac ttccaggaat ggtcggtgct cgcaggctcg    60
gca                                                                 63

<210> SEQ ID NO 298
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 298
tcgcttttag ctcctcgagt ttcttctgct cctcttttg ttttggtcgg tgctcgcagg     60
ctcggca                                                             67

<210> SEQ ID NO 299
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 299
tacttctggg ccgtcacagg ggagggcagg tggatggtga tcatggtcgg tgctcgcagg    60
ctcggca                                                             67

<210> SEQ ID NO 300
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 300
tggtgccgga tgaacttctt ggttctcttt ttgacgatct tgtggtcggt gctcgcaggc    60
tcggca                                                              66

<210> SEQ ID NO 301
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 301
tatgcctaga actttcacgc caattatttc acctcttgca catatggtcg gtgctcgcag    60
gctcggca                                                            68

<210> SEQ ID NO 302
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 302

```
cccaggtcct gtgatgttta ttgaaggaag caagggcagg gtggtcggtg ctcgcaggct    60
cggca                                                                65

<210> SEQ ID NO 303
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 303
gtccctttgt tttcttcttc tttttcccca ctctagttgg tacaggtggt cggtgctcgc    60
aggctcggca                                                           70

<210> SEQ ID NO 304
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 304
ccatcgatgt tggtgttgag tactcgcaaa atatgctggt cggtgctcgc aggctcggca    60

<210> SEQ ID NO 305
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 305
gataccacag aatcagcagg gtgagaaaca attgcacaaa agacttggtc ggtgctcgca    60
ggctcggca                                                            69

<210> SEQ ID NO 306
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 306
aaagcttgag atcacttgag gccagagttt tcagacctgg tcggtgctcg caggctcggc    60
a                                                                    61

<210> SEQ ID NO 307
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 307
cgggtgtgga cgggcggcgg atcggcaaag gcgaggctct tggtcggtgc tcgcaggctc    60
ggca                                                                 64

<210> SEQ ID NO 308
<211> LENGTH: 69
<212> TYPE: DNA
<213> ORGANISM: Artificial sequence
<220> FEATURE:
```

<223> OTHER INFORMATION: Synthetic oligonucleotide

<400> SEQUENCE: 308

```
cagcgcgagt gcagagcatg gtggtagatg tggcagagga tggcatggtc ggtgctcgca    60
ggctcggca                                                            69
```

<210> SEQ ID NO 309
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 309

```
gaccctcata gacagcagac agaagaggag taatatgatg tttattggtc ggtgctcgca    60
ggctcggca                                                            69
```

<210> SEQ ID NO 310
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 310

```
aaatacactt ttaattgatt tcagataaaa actacttggt cggtgctcgc aggctcggca    60
```

<210> SEQ ID NO 311
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 311

```
gccgcgcgaa gccggagagg agaagaagag aaggagggtt aggctggtcg gtgctcgcag    60
gctcggca                                                             68
```

<210> SEQ ID NO 312
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 312

```
caaatctcag ggaagcagtg atggaggaca caatctggct ggtcggtgct cgcaggctcg    60
gca                                                                  63
```

<210> SEQ ID NO 313
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 313

```
ggtcatagtg gagggtaaga gcttttacat cccgcagtgg tcggtgctcg caggctcggc    60
a                                                                    61
```

<210> SEQ ID NO 314
<211> LENGTH: 60

<212> TYPE: DNA
<213> ORGANISM: Artificial sequence
<220> FEATURE:
<223> OTHER INFORMATION: Synthetic oligonucleotide

<400> SEQUENCE: 314
gatccatcat ttctccttta agcttatctt ccaaaatggt cggtgctcgc aggctcggca    60

<210> SEQ ID NO 315
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 315
tgtttactga tttctgtctg gttaaacatc caatactggt cggtgctcgc aggctcggca    60

<210> SEQ ID NO 316
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 316
gcctatctct ttccatcaga ctccagtgat acccaatggt cggtgctcgc aggctcggca    60

<210> SEQ ID NO 317
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 317
cctgtaatct cagcacgttg ggaggcgagg tgggtggatg tggtcggtgc tcgcaggctc    60
ggca                                                                64

<210> SEQ ID NO 318
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 318
cttaaatacc agatacattt ttagtcctct acataatggt cggtgctcgc aggctcggca    60

<210> SEQ ID NO 319
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 319 gtttttgga agattcgggt tcagcacagg attccatttg gtcggtgctc gcaggctcgg    60
ca                                                                  62

<210> SEQ ID NO 320
<211> LENGTH: 65
<212> TYPE: DNA
<213> ORGANISM: Artificial sequence
<220> FEATURE:

<223> OTHER INFORMATION: Synthetic oligonucleotide

<400> SEQUENCE: 320

```
tgatatcctt gttttaact gttgtggctt gctgaatcaa atggtcggtg ctcgcaggct    60
cggca                                                              65
```

<210> SEQ ID NO 321
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 321

```
aagacggagt agttaagagc caggcctaat cggatggtgg tcggtgctcg caggctcggc    60
a                                                                    61
```

<210> SEQ ID NO 322
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 322

```
cgagttccag agacaatatc aaaattaccc tccttttggt cggtgctcgc aggctcggca    60
```

<210> SEQ ID NO 323
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 323

```
ggtgagagaa ctaatagcaa ccaggcaact gaggacgaag ttggtcggtg ctcgcaggct    60
cggca                                                                65
```

<210> SEQ ID NO 324
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 324

```
ttggggtgct ttatcttctt tgagttttcg cacaagatgg tcggtgctcg caggctcggc    60
a                                                                    61
```

<210> SEQ ID NO 325
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 325

```
gggcatgggc tcacattcac ttcctttata actccatcct ggtcggtgct cgcaggctcg    60
gca                                                                  63
```

<210> SEQ ID NO 326
<211> LENGTH: 65

```
<212> TYPE: DNA
<213> ORGANISM: Artificial sequence
<220> FEATURE:
<223> OTHER INFORMATION: Synthetic oligonucleotide

<400> SEQUENCE: 326
gcctgttttc cctttgctcc ccttttccct tttgtttgca ctggtcggtg ctcgcaggct    60
cggca                                                                65

<210> SEQ ID NO 327
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 327 cattttccg atagttaata gtaatggagt aataatgttg gtcggtgctc gcaggctcgg    60
ca                                                                   62

<210> SEQ ID NO 328
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 328
cacttggccc tttctcttct tatctcctcc cagttctggt cggtgctcgc aggctcggca    60

<210> SEQ ID NO 329
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 329
tcgtcctcct cctcttcatc cacaccatcc acctcggtgg tcggtgctcg caggctcggc    60
a                                                                    61

<210> SEQ ID NO 330
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 330
cctcctcttc ctccccacct tcttcctctt cttcgtctac tggtcggtgc tcgcaggctc    60
ggca                                                                 64

<210> SEQ ID NO 331
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 331
acgatggcgg agaaaggaag aggagggaag ctggcggaat ggtcggtgct cgcaggctcg    60
gca                                                                  63
```

<210> SEQ ID NO 332
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 332
tataatacaa aaaagacca aaaaacaaaa caaaacaaaa catcaatggt cggtgctcgc    60
aggctcggca                                                         70

<210> SEQ ID NO 333
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 333
aacacaagtg tgttgttgtc ttctatcttc ttcatggcat ggtcggtgct cgcaggctcg    60
gca                                                                 63

<210> SEQ ID NO 334
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 334
accaaaacca caatttctgc agtttaaaat gtttcacttg gtcggtgctc gcaggctcgg    60
ca                                                                  62

<210> SEQ ID NO 335
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 335
ccgctgctcg gtcccccagg ccccgccgtc cttgctgttt ggtcggtgct cgcaggctcg    60
gca                                                                 63

<210> SEQ ID NO 336
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 336
cgagatcctg gtgctcccac tcgcgttgct gcagcaagaa atggtcggtg ctcgcaggct    60
cggca                                                               65

<210> SEQ ID NO 337
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 337

```
gccggccggg gtggggaacg agcgccgggt tccgtcctgg tcggtgctcg caggctcggc    60
a                                                                    61

<210> SEQ ID NO 338
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 338
tctctgccac cgctggtgct gctgtctccc actcggtggt cggtgctcgc aggctcggca    60

<210> SEQ ID NO 339
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 339
catcgaagac gctcgcttca gaaatgtccc tgactgctgc gtggtcggtg ctcgcaggct    60
cggca                                                                65

<210> SEQ ID NO 340
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 340
gtctttcagg tcaatgtagt gctgcttcag gtgttcttca gagtggtcgg tgctcgcagg    60
ctcggca                                                              67

<210> SEQ ID NO 341
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 341
catcagcata gcctccgatg accatggtgt tccacaaagg gttggtcggt gctcgcaggc    60
tcggca                                                               66

<210> SEQ ID NO 342
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 342
gatgcccaga atcagggccc agatgttcag gcacttggcg gtggtggtcg gtgctcgcag    60
gctcggca                                                             68

<210> SEQ ID NO 343
<211> LENGTH: 70
<212> TYPE: DNA
<213> ORGANISM: Artificial sequence
<220> FEATURE:
```

<223> OTHER INFORMATION: Synthetic oligonucleotide

<400> SEQUENCE: 343

```
agaaccggaa gagaaagggg ctgcggtgca gcacgggaaa tagggttggt cggtgctcgc      60
aggctcggca                                                            70
```

<210> SEQ ID NO 344
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 344

```
cccccaacc ctcactgttt cccgttgcca ttgatggtgg tcggtgctcg caggctcggc      60
a                                                                     61
```

<210> SEQ ID NO 345
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 345

```
acctcatagg tgcctgcgtg ggcgctcttg tggtccaggc tctggtcggt gctcgcaggc      60
tcggca                                                                66
```

<210> SEQ ID NO 346
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 346

```
acaggagtct tgcccaagcc ctgtcatgtc agtgtgtgtg tggtcggtgc tcgcaggctc      60
ggca                                                                  64
```

<210> SEQ ID NO 347
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 347

```
cttcttcaag gtgatataga cgctgcccga cgtccggtgg tcggtgctcg caggctcggc      60
a                                                                     61
```

<210> SEQ ID NO 348
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 348

```
gccatctggg ccatcagacc tggctgccgg ggcgcatggt cggtgctcgc aggctcggca      60
```

<210> SEQ ID NO 349
<211> LENGTH: 62

```
<212> TYPE: DNA
<213> ORGANISM: Artificial sequence
<220> FEATURE:
<223> OTHER INFORMATION: Synthetic oligonucleotide

<400> SEQUENCE: 349
gcttcttggg aaatgaagcc acagccagct catatatgtg gtcggtgctc gcaggctcgg    60
ca                                                                   62

<210> SEQ ID NO 350
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 350
ctcatccacg atggctgcta tcggtaaaca gttaaaacag tctgttggtc ggtgctcgca    60
ggctcggca                                                            69

<210> SEQ ID NO 351
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 351
tgacccgctc gatcggagcc acggccgtct tggagatggt ggtcggtgct cgcaggctcg    60
gca                                                                  63

<210> SEQ ID NO 352
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 352
gggtgatcag ctgtgaggca ttgaacttgg ccaccacact cttggtcggt gctcgcaggc    60
tcggca                                                               66

<210> SEQ ID NO 353
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 353
acagcacagt aacaaagtta ttaggaaaac aggactacca caaagatggt cggtgctcgc    60
aggctcggca                                                           70

<210> SEQ ID NO 354
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 354
accaatgttt tttagaatag tggcaccatc attggttggt cggtgctcgc aggctcggca    60
```

<210> SEQ ID NO 355
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 355
gcagtttacg ctgtctagcc agagtttcac cgtaaatatg attggtcggt gctcgcaggc    60
tcggca    66

<210> SEQ ID NO 356
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 356
cactctttca cttaaagaga tatagctaga aggattcaca gtggtcggtg ctcgcaggct    60
cggca    65

<210> SEQ ID NO 357
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 357
accttcaggt cgtccagctg tttcagcagc tcctcctggt cggtgctcgc aggctcggca    60

<210> SEQ ID NO 358
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 358
gccgtcaact tgcgtcggaa catggtcccc gcttctcgct ctggtctggt cggtgctcgc    60
aggctcggca    70

<210> SEQ ID NO 359
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 359
cgatccaaaa agtgcgcgat gcgagtagtc aagtcgtact ggtcggtgct cgcaggctcg    60
gca    63

<210> SEQ ID NO 360
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 360
agacaatggt ccctctattt caacaccttt ttcggtgaca gtgtggtcgg tgctcgcagg    60
ctcggca 67

<210> SEQ ID NO 361
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 361
ggtgatcttg ctcttgctcc tttcgatggt caccaccct ccatggtcgg tgctcgcagg    60
ctcggca                                                              67

<210> SEQ ID NO 362
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 362
aacagccttt agttctacag gaaatggcac tgatggacag aagtggtcgg tgctcgcagg    60
ctcggca                                                              67

<210> SEQ ID NO 363
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 363
ccggctgtct gtcttggtgc tctccacctt ccgcaccacc tctggtcggt gctcgcaggc    60
tcggca                                                               66

<210> SEQ ID NO 364
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 364
gggaggtgaa cccagaacca gttcccccac caaagctgtg gaaatggtcg gtgctcgcag    60
gctcggca                                                             68

<210> SEQ ID NO 365
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 365
tcacaacagg ggaggccttg gtgaaagctg ggtggaaaac cctggtcggt gctcgcaggc    60
tcggca                                                               66

<210> SEQ ID NO 366
<211> LENGTH: 64
<212> TYPE: DNA
<213> ORGANISM: Artificial sequence
<220> FEATURE:

<223> OTHER INFORMATION: Synthetic oligonucleotide

<400> SEQUENCE: 366
gtggagtcta gaggatccac agctggatag atgcccagct tggtcggtgc tcgcaggctc    60
ggca    64

<210> SEQ ID NO 367
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 367
aggtaaaggc ctgcagcgat gaaacagttg tagctgactt gcttggtcgg tgctcgcagg    60
ctcggca    67

<210> SEQ ID NO 368
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 368
tcattgattg gttgcccgtc aaatcggaat ctgatctgct ggtcggtgct cgcaggctcg    60
gca    63

<210> SEQ ID NO 369
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 369
gctgaaactt tcacaggctt cacaatcttt tgcttaggtg ctgccttggt cggtgctcgc    60
aggctcggca    70

<210> SEQ ID NO 370
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 370
cacatagaag tccaggccgt agataccaat gcttggtggt cggtgctcgc aggctcggca    60

<210> SEQ ID NO 371
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 371
accatgccca gcacatcctg cacatgctgg cccaggttgg agccctggtc ggtgctcgca    60
ggctcggca    69

<210> SEQ ID NO 372
<211> LENGTH: 60

```
<212> TYPE: DNA
<213> ORGANISM: Artificial sequence
<220> FEATURE:
<223> OTHER INFORMATION: Synthetic oligonucleotide

<400> SEQUENCE: 372
ggtgatggta gcctttctgc ccagcgcgtg ccacagtggt cggtgctcgc aggctcggca      60

<210> SEQ ID NO 373
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 373
gccgcatccg cgtcagattc ccaaactcgc ggcccattgt ggctggtcgg tgctcgcagg      60
ctcggca                                                               67

<210> SEQ ID NO 374
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 374
ttgctgtcac cagcaacgtt gccacgacga acatccttga cagacatggt cggtgctcgc      60
aggctcggca                                                            70

<210> SEQ ID NO 375
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 375
gctggtataa ggtggtctgg ttgacttctg gtgtccccac gtggtcggtg ctcgcaggct      60
cggca                                                                 65

<210> SEQ ID NO 376
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 376
cggcatcctc tcaggagggc cggtccgggt ctcagcgcgc tggtcggtg ctcgcaggct       60 cggca                                                                 65

<210> SEQ ID NO 377
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 377
aggttaacca tgtgcccgtc gatgtccttg gcggaaaact cgtgcatggt cggtgctcgc      60
aggctcggca                                                            70
```

<210> SEQ ID NO 378
<211> LENGTH: 70
<212> TYPE: DNA
<213> ORGANISM: Artificial sequence
<220> FEATURE:
<223> OTHER INFORMATION: Synthetic oligonucleotide

<400> SEQUENCE: 378
accacaaact cttccaccag ccagcatggc aaatttgagg tgcttgtggt cggtgctcgc    60
aggctcggca                                                          70

<210> SEQ ID NO 379
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 379
tggagattgc agtgagctga gatcacacca ctgggctcca gccttggtcg gtgctcgcag    60
gctcggca                                                            68

<210> SEQ ID NO 380
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 380
ggccagtggt cttggtgtgc tggcctcgga cacgaatggt cggtgctcgc aggctcggca    60

<210> SEQ ID NO 381
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 381
gcagctggag catctccacc cttggtattt ctggtgtaat ggtcggtgct cgcaggctcg    60
gca                                                                 63

<210> SEQ ID NO 382
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 382
gtagctgggg gtgctggggt tcattctcgg cacggctgct ggtcggtgct cgcaggctcg    60
gca                                                                 63

<210> SEQ ID NO 383
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 383
gctgtaacca caccgacgcg cgagctctgc gcgggcttca ctggtcggtg ctcgcaggct    60
cggca 65

<210> SEQ ID NO 384
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 384
tccaggtcga tctccaagga ctggactgta cgtctcagct cttggtcggt gctcgcaggc 60
tcggca 66

<210> SEQ ID NO 385
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 385
ttaacctacc actgttttgt ttagagcgaa cacagtgtgg tcggtgctcg caggctcggc 60
a 61

<210> SEQ ID NO 386
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 386
tctcctccag ggtggctgtc actgcctggt acttccatgg tcggtgctcg caggctcggc 60
a 61

<210> SEQ ID NO 387
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 387
cacgacagca aatagcacgg gtcagatgcc cttggctgaa aagtggtcgg tgctcgcagg 60
ctcggca 67

<210> SEQ ID NO 388
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 388
gggaccagcc gtccttatca aagtgctccc agaaattggt cggtgctcgc aggctcggca 60

<210> SEQ ID NO 389
<211> LENGTH: 28
<212> TYPE: DNA
<213> ORGANISM: Artificial sequence
<220> FEATURE:
<223> OTHER INFORMATION: Synthetic oligonucleotide

```
<400> SEQUENCE: 389
acaaccgaat tcgcgattt tttttttt                                            28

<210> SEQ ID NO 390
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 390
tagcgcctgc ggcctgt                                                       17

<210> SEQ ID NO 391
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 391
ctctctctgu                                                               10

<210> SEQ ID NO 392
<211> LENGTH: 97
<212> TYPE: DNA
<213> ORGANISM: Artificial sequence
<220> FEATURE:
<223> OTHER INFORMATION: Synthetic oligonucleotide

<400> SEQUENCE: 392
tagcgcctgc ggcctgtctc tctctguaaa cgcatcggtc gaattatctc ctgctaggca        60
ctcgctgtgc cctggactat cgtaacccat gctgttt                                 97

<210> SEQ ID NO 393
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 393
gtgtgactgu                                                               10

<210> SEQ ID NO 394
<211> LENGTH: 55
<212> TYPE: DNA
<213> ORGANISM: Artificial sequence
<220> FEATURE:
<223> OTHER INFORMATION: Synthetic oligonucleotide

<400> SEQUENCE: 394
cttgcggaac acgaatcgac cactgacaca attcgtaatc tcattgcaag cgttt             55

<210> SEQ ID NO 395
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 395
cagagactgu                                                               10
```

```
<210> SEQ ID NO 396
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 396
atgcccattc agcctcacgt ggtgctgatt tggggtgttt                              40

<210> SEQ ID NO 397
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 397
acaggccgca ggcgctattt tttttttttt t                                      31

<210> SEQ ID NO 398
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 398
gtggatgatc aacgc                                                        15

<210> SEQ ID NO 399
<211> LENGTH: 77
<212> TYPE: DNA
<213> ORGANISM: Artificial sequence
<220> FEATURE:
<223> OTHER INFORMATION: Synthetic oligonucleotide

<400> SEQUENCE: 399
ucgcttccat accgggcgat ggacacaatt aagatcgcat ttagagtgaa gtatcaatcg        60
gaaatcgtgc agcgacc                                                      77

<210> SEQ ID NO 400
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 400
ucaatcaacc agattaggac tcggttcccg tgagaaatag aagtccgtat aaacgttcaa        60
cggggtc                                                                 67

<210> SEQ ID NO 401
<211> LENGTH: 47
<212> TYPE: DNA
<213> ORGANISM: Artificial sequence
<220> FEATURE:
<223> OTHER INFORMATION: Synthetic oligonucleotide

<400> SEQUENCE: 401
ucgcttccat accgggcgat ggacacaatt aagatcgcat ttagagt                     47

<210> SEQ ID NO 402
<211> LENGTH: 15
<212> TYPE: DNA
```

```
<213> ORGANISM: Artificial sequence
<220> FEATURE:
<223> OTHER INFORMATION: Synthetic oligonucleotide

<400> SEQUENCE: 402
gcgttgatca tccac                                                    15

<210> SEQ ID NO 403
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 403
atagactcgt tttttttttt ttt                                           23

<210> SEQ ID NO 404
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 404
gtggatgatc aacgcacact ctctcgcttc                                    30

<210> SEQ ID NO 405
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 405
gagagtgtgc gttgatcatc cac                                           23

<210> SEQ ID NO 406
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 406
gatcaacgca cactctctcg cttc                                          24

<210> SEQ ID NO 407
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 407
gtggatgatc aacgcactca gtctcaatca                                    30

<210> SEQ ID NO 408
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 408
gactgagtgc gttgatcatc cac                                           23
```

<210> SEQ ID NO 409
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n = degenerative nucleotide A or T
<220> FEATURE:
<221> NAME/KEY: misc_feature
<222> LOCATION: (3)..(3)
<223> OTHER INFORMATION: n = degenerative nucleotide G or C
<220> FEATURE:
<221> NAME/KEY: misc_feature
<222> LOCATION: (4)..(4)
<223> OTHER INFORMATION: n = degenerative nucleotide A or T
<220> FEATURE:
<221> NAME/KEY: misc_feature
<222> LOCATION: (5)..(5)
<223> OTHER INFORMATION: n = degenerative nucleotide G or C
<220> FEATURE:
<221> NAME/KEY: misc_feature
<222> LOCATION: (6)..(6)
<223> OTHER INFORMATION: n = degenerative nucleotide A or T
<220> FEATURE:
<221> NAME/KEY: misc_feature
<222> LOCATION: (7)..(7)
<223> OTHER INFORMATION: n = degenerative nucleotide G or C

<400> SEQUENCE: 409
gnnnnnntgc gttgatcatc cac                                      23

<210> SEQ ID NO 410
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 410
gtcgacaatc aacgcacact ctguaacgca                               30

<210> SEQ ID NO 411
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n = degenerative nucleotide A or T
<220> FEATURE:
<221> NAME/KEY: misc_feature
<222> LOCATION: (3)..(3)
<223> OTHER INFORMATION: n = degenerative nucleotide G or C
<220> FEATURE:
<221> NAME/KEY: misc_feature
<222> LOCATION: (4)..(4)
<223> OTHER INFORMATION: n = degenerative nucleotide A or T
<220> FEATURE:
<221> NAME/KEY: misc_feature
<222> LOCATION: (5)..(5)
<223> OTHER INFORMATION: n = degenerative nucleotide G or C
<220> FEATURE:
<221> NAME/KEY: misc_feature
<222> LOCATION: (6)..(6)
<223> OTHER INFORMATION: n = degenerative nucleotide A or T
<220> FEATURE:
<221> NAME/KEY: misc_feature
<222> LOCATION: (7)..(7)

<223> OTHER INFORMATION: n = degenerative nucleotide G or C

<400> SEQUENCE: 411
cnnnnnntgc gttgattgtc gac                                               23

<210> SEQ ID NO 412
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 412
gtcgacaatc aacgcacact ctg                                               23

<210> SEQ ID NO 413
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 413
gtcgacaatc aacgcacact ctgaacgcat                                        30

<210> SEQ ID NO 414
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 414
gtcgacaatc aacgcacact ct                                                22

<210> SEQ ID NO 415
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 415
gtggatgatc aacgcacact ctgaacgcat                                        30

<210> SEQ ID NO 416
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n = degenerative nucleotide A or T
<220> FEATURE:
<221> NAME/KEY: misc_feature
<222> LOCATION: (3)..(3)
<223> OTHER INFORMATION: n = degenerative nucleotide G or C
<220> FEATURE:
<221> NAME/KEY: misc_feature
<222> LOCATION: (4)..(4)
<223> OTHER INFORMATION: n = degenerative nucleotide A or T
<220> FEATURE:
<221> NAME/KEY: misc_feature
<222> LOCATION: (5)..(5)
<223> OTHER INFORMATION: n = degenerative nucleotide G or C
<220> FEATURE:
<221> NAME/KEY: misc_feature

```
<222> LOCATION: (6)..(6)
<223> OTHER INFORMATION: n = degenerative nucleotide A or T
<220> FEATURE:
<221> NAME/KEY: misc_feature
<222> LOCATION: (7)..(7)
<223> OTHER INFORMATION: n = degenerative nucleotide G or C

<400> SEQUENCE: 416
cnnnnnntgc gttgatcatc cac                                              23

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 417
gtggatgatc aacgca                                                      16

<210> SEQ ID NO 418
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 418
gtcgacaatc aacgcacact ctcaacgcat                                       30

<210> SEQ ID NO 419
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: n = degenerative nucleotide A or T

<400> SEQUENCE: 419
gtcgacaatc aacgcactgn gtctgggaag                                       30

<210> SEQ ID NO 420
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: n = degenerative nucleotide A or T

<400> SEQUENCE: 420
gtcgacaatc aacgcagtga gnccaagtac                                       30

<210> SEQ ID NO 421
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n = degenerative nucleotide G or C
<220> FEATURE:
```

```
<221> NAME/KEY: misc_feature
<222> LOCATION: (22)..(22)
<223> OTHER INFORMATION: n = degenerative nucleotide A or T

<400> SEQUENCE: 421
gtcgacaatc aacgcagact nnccaagtac                                          30
```